United States Patent
Shiratori et al.

(10) Patent No.: US 10,900,045 B2
(45) Date of Patent: Jan. 26, 2021

(54) PROTEIN, NOVEL GENE, EXPRESSION VECTOR, TRANSFORMANT, METHOD FOR PRODUCING TRANSFORMANT, AND METHOD FOR SCREENING FOR NOVEL FLUORESCENT PROTEIN

(71) Applicant: NEC Solution Innovators, Ltd., Tokyo (JP)

(72) Inventors: Ikuo Shiratori, Koto-ku (JP); Akihisa Shimizu, Koto-ku (JP); Katsunori Horii, Koto-ku (JP); Hiroshi Mishima, Koto-ku (JP); Iwao Waga, Koto-ku (JP)

(73) Assignee: NEC Solution Innovators. Ltd., Tokyo (JP)

( * ) Notice: Subject to any disclaimer, the term of this patent is extended or adjusted under 35 U.S.C. 154(b) by 337 days.

(21) Appl. No.: 15/737,517

(22) PCT Filed: Jun. 13, 2016

(86) PCT No.: PCT/JP2016/067586
§ 371 (c)(1),
(2) Date: Dec. 18, 2017

(87) PCT Pub. No.: WO2016/204123
PCT Pub. Date: Dec. 22, 2016

(65) Prior Publication Data
US 2018/0187206 A1    Jul. 5, 2018

(30) Foreign Application Priority Data

Jun. 19, 2015 (JP) ................................. 2015-124229
Apr. 28, 2016 (JP) ................................. 2016-092095

(51) Int. Cl.
| | | |
|---|---|---|
| C12N 15/82 | (2006.01) | |
| C12N 15/09 | (2006.01) | |
| C12N 5/10 | (2006.01) | |
| C07K 14/435 | (2006.01) | |
| A01H 1/04 | (2006.01) | |

(52) U.S. Cl.
CPC .......... *C12N 15/8212* (2013.01); *A01H 1/04* (2013.01); *C07K 14/435* (2013.01); *C07K 14/43595* (2013.01); *C12N 5/10* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 7,442,768 B2 * | 10/2008 | Tsuji ................ | C07K 14/43509 |
| | | | 435/183 |
| 2002/0099170 A1 | 7/2002 | Osumi et al. | |
| 2005/0014223 A1 | 1/2005 | Gurtu | |
| 2005/0221338 A1 | 10/2005 | Tsuji et al. | |
| 2009/0318673 A1 | 12/2009 | Suto et al. | |
| 2010/0043104 A1 | 2/2010 | Waga et al. | |

FOREIGN PATENT DOCUMENTS

| | | |
|---|---|---|
| JP | 11-266883 A | 10/1999 |
| JP | 2008-22817 A | 2/2008 |
| JP | 4741994 B2 | 8/2011 |
| JP | 4863280 B2 | 1/2012 |
| WO | 2004/090115 A2 | 10/2004 |
| WO | 2005/095599 A1 | 10/2005 |
| WO | 2007/086473 A1 | 8/2007 |
| WO | 2008/013202 A1 | 1/2008 |

OTHER PUBLICATIONS

Sokalingam et al. In silico study on the effect of surface lysines and arginines on the electrostatic interactions and protein stability. Biotechnology and Bioprocesse Engineering 18: 18-26, 2013.*
Chalfie et al., "Green Fluorescent Protein as a Marker for Gene Expression", Science, Feb. 11, 1994, pp. 802-805, vol. 263, No. 5148.
Steven R. Kain, "Enhanced Variant of the Green Fluorescent Protein for Greater Sensitivity, Different Colours and Detection of Apoptosis", Fluorescent and Luminescent Probes, 2nd Edition, Chapter 19, 1999, pp. 284 -292.
International Search Report for PCT/JP2016/067586 dated Sep. 20, 2016.
Communication dated Oct. 16, 2018 from the Japanese Patent Office in counterpart Application No. 2017-525229.
Roger Heim et al., "Wavelength mutations and posttranslational autoxidation of green fluorescent protein", Proc. Natl. Acad. Sci. USA, vol. 91, Dec. 1994, pp. 2501-12504 (4 pages total).
Communication dated Apr. 2, 2019, from Japanese Patent Office in counterpart application No. 2017-525229.
Communication dated Dec. 7, 2018 from the Taiwanese Patent Office in application No. 105119073.

* cited by examiner

*Primary Examiner* — Iqbal H Chowdhury
(74) *Attorney, Agent, or Firm* — Sughrue Mion, PLLC

(57) ABSTRACT

The present invention provides a novel fluorescent protein. A novel protein includes the following protein (F1):
(F1) a protein consisting of an amino acid sequence of SEQ ID NO: 1, wherein
in the amino acid sequence of SEQ ID NO: 1,
a 52nd amino acid $Xaa_{52}$ is an arbitrary amino acid,
a 133rd amino acid $Xaa_{133}$ is an arbitrary amino acid, and
a 154th amino acid $Xaa_{154}$ is an arbitrary amino acid.

6 Claims, 11 Drawing Sheets

Specification includes a Sequence Listing.

V500 channel (F1-27) Protein expression cancer cell

Fluorescence intensity (F1-42) Protein expression cancer cell

Fluorescence intensity

FITC channel (F1-2) Protein expression cancer cell

Fluorescence intensity (F1-42) Protein expression cancer cell

Fluorescence intensity

PROTEIN, NOVEL GENE, EXPRESSION VECTOR, TRANSFORMANT, METHOD FOR PRODUCING TRANSFORMANT, AND METHOD FOR SCREENING FOR NOVEL FLUORESCENT PROTEIN

CROSS REFERENCE TO RELATED APPLICATIONS

This application is a National Stage of International Application No. PCT/JP2016/067586 filed Jun. 13, 2016, claiming priority based on Japanese Patent Application Nos. 2015-124229 filed Jun. 19, 2015 and 2016-092095 filed Apr. 28, 2016, the contents of all of which are incorporated herein by reference in their entirety.

TECHNICAL FIELD

The present invention relates to a novel protein, a novel gene, an expression vector, a transformant, a method for producing a transformant, and a method for screening a novel fluorescent protein.

BACKGROUND ART

Green fluorescent proteins (GFPs), yellow fluorescent proteins (YFPs), and the like are commonly used as fluorescent proteins (Non-Patent Document 1). The fluorescent proteins are used for various purposes such as researches, however, there is not always a suitable fluorescent protein for each purpose. Thus, there is a demand for a novel fluorescent protein.

CITATION LIST

Non-Patent Document(s)

Non-Patent Document 1: Chalfie M et al., "Green fluorescent protein as a marker for gene expression", Science, February 1994, Vol. 263, no. 5148, p 802-805.

DISCLOSURE OF THE INVENTION

Problem to be Solved by the Invention

Hence, the present invention is intended to provide a novel fluorescent protein.

Means for Solving Problem

The present invention provides a novel protein including the following protein (F1):
(F1) a protein consisting of an amino acid sequence of SEQ ID NO: 1, wherein
in the amino acid sequence of SEQ ID NO: 1,
a 52nd amino acid $Xaa_{52}$ is an arbitrary amino acid,
a 133rd amino acid $Xaa_{133}$ is an arbitrary amino acid, and
a 154th amino acid $Xaa_{154}$ is an arbitrary amino acid.
The present invention provides a novel gene including the following polynucleotide (f1):
(f1) a polynucleotide consisting of a base sequence of SEQ ID NO: 14, wherein
in the base sequence of SEQ ID NO: 14,
a 154th base $N_{154}$, a 155th base $N_{155}$, and a 156th base $N_{156}$ form a codon encoding an arbitrary amino acid,
a 397th base $N_{397}$, a 398th base $N_{398}$, and a 399th base $N_{399}$ form a codon encoding an arbitrary amino acid, and
a 460th base $N_{460}$, a 461st base $N_{461}$, and a 462nd base $N_{462}$ form a codon encoding an arbitrary amino acid.

The present invention provides an expression vector including the novel gene according to the present invention.

The present invention provides a transformant including the novel gene according to the present invention.

The present invention provides a method for producing a transformant, including a step of:
transfecting the novel gene according to the present invention to a host.

The present invention provides a method for screening a novel fluorescent protein, including a step of:
selecting a protein having a fluorescence activity in which each of an amino acid corresponding to the 52nd amino acid $Xaa_{52}$, an amino acid corresponding to the 133rd amino acid $Xaa_{133}$, and an amino acid corresponding to the 154th amino acid $Xaa_{154}$ in the amino acid sequence of SEQ ID NO: 1 is an arbitrary amino acid from a candidate protein obtained by introducing a mutation to the novel protein according to the present invention.

Effects of the Invention

According to the present invention, a fluorescent protein can be provided.

DESCRIPTION OF EXEMPLARY EMBODIMENT

<Novel Protein>

Figure 1A:
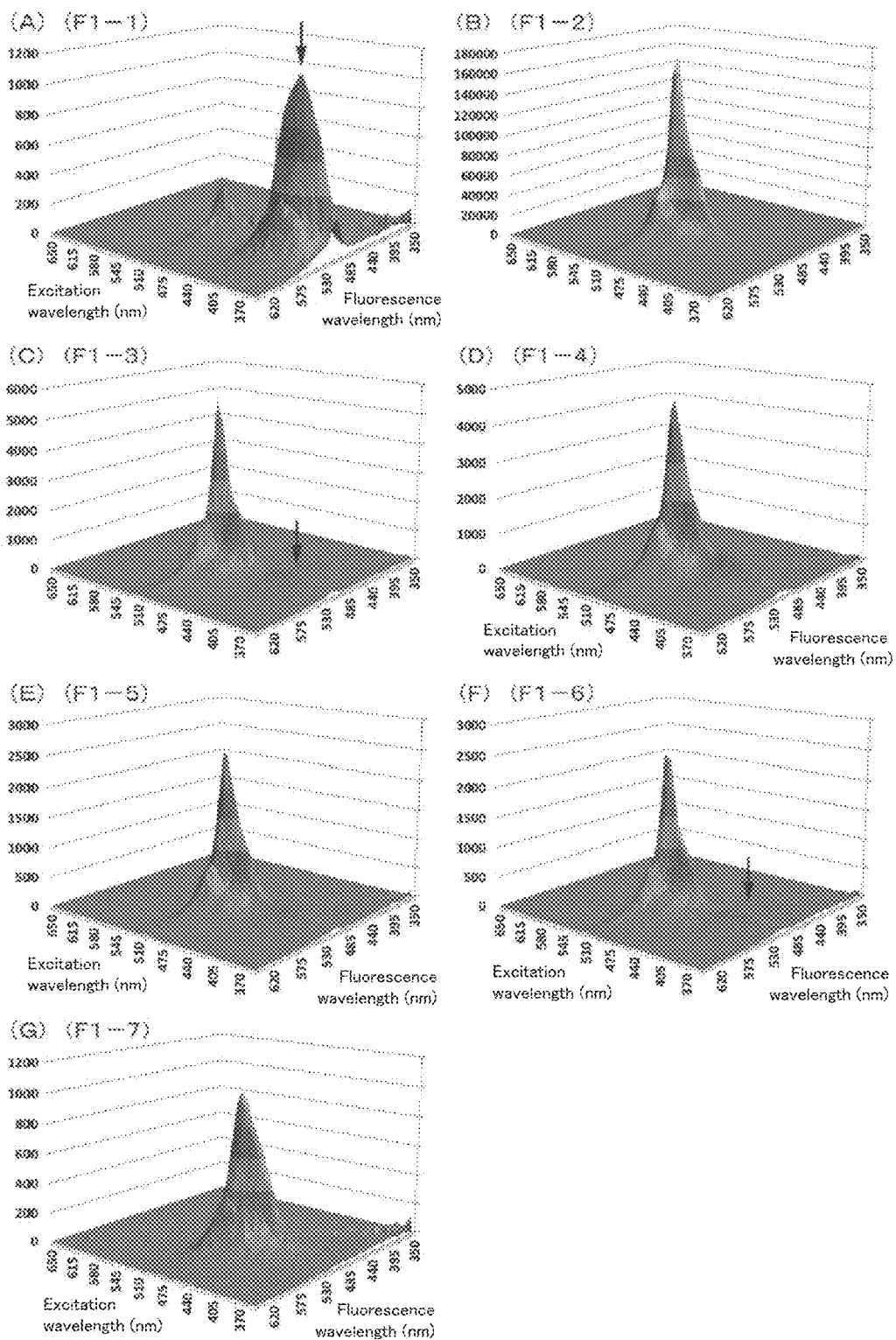
FIG. 1A shows graphs showing the fluorescence intensities at different excitation wavelengths and fluorescence wavelengths in Example 1.

The novel protein of the present invention is, as described above, at least one selected from the group consisting of the following proteins (F1) to (F3):

(F1) a protein consisting of an amino acid sequence of SEQ ID NO: 1, in the amino acid sequence of SEQ ID NO: 1, the 52nd amino acid $Xaa_{52}$ is an arbitrary amino acid, the 133rd amino acid $Xaa_{133}$ is an arbitrary amino acid, and the 154th amino acid $Xaa_{154}$ is an arbitrary amino acid;

(F2) a protein having a fluorescence activity and consisting of an amino acid sequence obtained by deletion, substitution, insertion, and/or addition of one to several amino acids in an amino acid sequence excluding the 52nd amino acid $Xaa_{52}$, the 133rd amino acid $Xaa_{133}$, and the 154th amino acid $Xaa_{154}$ of the protein (F1); and (F3) a protein having a fluorescence activity and consisting of an amino acid sequence having at least 80% identity to the amino acid sequence of the protein (F1) excluding the 52nd amino acid $Xaa_{52}$, the 133rd amino acid $Xaa_{133}$, and the 154th amino acid $Xaa_{154}$, The inventors of the present invention conducted earnest studies and found out that, in a protein including the amino acid sequence of SEQ ID NO: 1, the 52nd amino acid, the 133rd amino acid, and the 154th amino acid related to the fluorescence activity of the protein. Specifically, it is estimated that the 52nd amino acid, the 133rd amino acid, and the 154th amino acid in the protein interact with the chromophore of the protein, for example.

Thus, the novel protein of the present invention having the 52nd amino acid, the 133rd amino acid, and the 154th amino acid being arbitrary amino acids can adjust its fluorescence activity. For example, a protein that shows stronger fluorescence even with excitation light (e.g., ultraviolet (hereinafter, the same applies)) having a relatively low wavelength and a protein that shows stronger fluorescence under excitation with excitation light at the same intensity can be obtained. The above-described estimation, however, does not limit the present invention by any means.

Hereinafter, the novel protein may be also called a novel fluorescent protein. The novel fluorescent protein is a protein newly produced by the inventors of the present invention. In the present invention, for example, the novel fluorescent protein may include one type of protein or two or more types of proteins (hereinafter, the same applies).

The amino acid sequence of SEQ ID NO: 1 in the protein (F1) is as follows. In the following amino acid sequence, the first amino acid (X) of three boxed amino acids is an amino acid corresponding to the $Xaa_{52}$, the second amino acid (X) of three boxed amino acids is an amino acid corresponding the $Xaa_{133}$, and the third amino acid (X) of three boxed amino acids is an amino acid corresponding to the $Xaa_{154}$. Moreover, in the following amino acid sequence, the first amino acid of two underlined amino acids is an amino acid corresponding to the $Xaa_{198}$ and the second amino acid of two underlined amino acids is an amino acid corresponding to the $Xaa_{205}$.

Amino acid sequence of (F1)
(SEQ ID NO: 1)
MTTFKIESRIHGNLNGEKFELVGGGVGEEGRLEIEMKTKDKPLAFSPF

LLS☒CMGYGFYHFASFPKGTKNIYLHAATNGGYTNTRKEIYEDGGIL

EVNFRYTYEFNKIIGDVECIGHGFPSQSPIFKDTIVK☒CPTVDLMLPM

SGNIIASSYA☒AFQLKDGSFYTAEVKNNIDFKNPIHESFSKSGPMFTH

RRVEET<u>H</u>TKENLA<u>M</u>VEYQQVFNSAPRDM

In the protein (F1), the $Xaa_{52}$ is an arbitrary amino acid. The arbitrary amino acid is A, C, D, E, F, G, H, I, K, L, M, N, P, Q, R, S, T, V, W, or Y, is preferably C, F, H, K, M, or T, and is more preferably C, M, or T as it shows stronger fluorescence even with excitation light having a relatively low wavelength, for example. In the protein (F1), the $Xaa_{52}$ is more preferably H as it shows stronger fluorescence under excitation with excitation light at the same intensity, for example.

In the protein (F1), the $Xaa_{133}$ is an arbitrary amino acid. The arbitrary amino acid is A, C, D, E, F, G, H, I, K, L, M, N, P, Q, R, S, T, V, W, or Y and is preferably L, Q, S, or T. In the protein (F1), the $Xaa_{133}$ is more preferably T as it shows stronger fluorescence under excitation with excitation light at the same intensity, for example.

In the protein (F1), the $Xaa_{154}$ is an arbitrary amino acid. The arbitrary amino acid is A, C, D, E, F, G, H, I, K, L, M, N, P, Q, R, S, T, V, W, or Y, is preferably A, H, I, K, L, Q, V, or Y, and more preferably A, I, L, V, or Y as it shows stronger fluorescence even with excitation light having a relatively low wavelength, for example. In the protein (F1), the $Xaa_{154}$ is more preferably K as it shows stronger fluorescence under excitation with excitation light at the same intensity, for example.

In the protein (F1), the combination of $Xaa_{52}$, $Xaa_{133}$, and $Xaa_{154}$ is not limited to particular combinations, and can be, for example, as follows:
$Xaa_{52}$ is, for example, C, F, H, K, M, or T,
$Xaa_{133}$ is, for example, L, Q, S, or T, and
$Xaa_{154}$ is, for example, A, H, I, K, L, Q, V, or Y.

In the protein (F1), the combination of $Xaa_{52}$, $Xaa_{133}$, and $Xaa_{154}$ is preferably as follows, for example, as it shows stronger fluorescence even with excitation light having a relatively low wavelength:
$Xaa_{52}$ is, for example, C, M, or T,
$Xaa_{133}$ is, for example, L, Q, S, or T, and
$Xaa_{154}$ is, for example, A, I, L, V, or Y.

In the description below, in the case where the protein (F1) includes the $Xaa_{52}$, the $Xaa_{133}$, and the $Xaa_{154}$ in such a combination, the protein (F1) is also referred to as protein (B1), and the proteins (F2) and (F3) are also referred to as proteins (B2) and (B3) when the protein (F1) is the protein (B1). Also in the description below, regarding the proteins (B2) and (B3), for example, reference can be made to the description as to the proteins (F2) and (F3) by replacing (F1) with (B1), (F2) with (B2), and (F3) with (B3), respectively.

As a specific example, in the novel protein of the present invention, the combination of the $Xaa_{52}$, the $Xaa_{133}$, and the $Xaa_{154}$ is for example, one of the following combinations (aa1) to (aa12). In the novel protein of the present invention, the combination of the $Xaa_{52}$, the $Xaa_{133}$, and the $Xaa_{154}$ is preferably the combination (aa1), (aa3), (aa6), (aa9), (aa10), or (aa12) and is more preferably the combination (aa1) or (aa9), for example, as it shows stronger fluorescence even with excitation light having a relatively low wavelength. In the novel protein of the present invention, the combination of the $Xaa_{52}$, the $Xaa_{133}$, and the $Xaa_{154}$ is preferably the combination (aa2), for example, as it shows stronger fluorescence under excitation with excitation light at the same intensity. The novel protein of the present invention is a protein except for the protein in which the $Xaa_{52}$, the $Xaa_{133}$, and the $Xaa_{154}$ are H, S, and R, respectively, and the protein in which the $Xaa_{52}$, the $Xaa_{133}$, and the $Xaa_{154}$ are D, S, and R, respectively, for example.

TABLE 1

|  | $Xaa_{52}$ | $Xaa_{133}$ | $Xaa_{154}$ |
|---|---|---|---|
| (aa1) | T | S | Y |
| (aa2) | H | T | K |
| (aa3) | C | L | L |
| (aa4) | C | S | H |
| (aa5) | T | S | H |
| (aa6) | M | L | V |
| (aa7) | F | S | Q |
| (aa8) | K | T | A |
| (aa9) | C | Q | L |
| (aa10) | T | T | I |
| (aa11) | K | S | Q |
| (aa12) | M | L | A |

In the novel protein of the present invention, the $Xaa_{205}$ is preferably substituted with I as it shows stronger fluorescence even with excitation light having a relatively low wavelength, for example. In the novel protein of the present invention, the $Xaa_{198}$ is preferably substituted with L or H as it shows stronger fluorescence even with excitation light having a relatively low wavelength, for example. In the novel protein, it is estimated that the 198th and the 205th amino acids interact with the chromophore of the protein, for example. Thus, it is estimated that, by conducting the above-described substitution of one of the 198th and the 205th amino acids, a protein that shows stronger fluorescence even with excitation light having a relatively low wavelength is obtained. The above-described estimation, however, does not limit the present invention by any means. In the novel protein of the present invention, the $Xaa_{198}$ and the $Xaa_{205}$ are more preferably L and I, respectively, or H and I, respectively, as it shows further stronger fluorescence even with excitation light having a relatively low wavelength, for example.

The protein (F1) can be, for example, a protein consisting of at least one amino acid sequence selected from the group consisting of SEQ ID NOs: 2 to 13, 34 to 67, for example. In the case where the protein (F1) is a protein consisting of at least one amino acid sequence selected from the group consisting of SEQ ID NOs: 2 to 13 and 34 to 67, the protein (F1) is also referred to as one of proteins (F1-1) to (F1-46), the protein (F2) is also referred to as one of proteins (F2-1) to (F2-46), and the protein (F3) is also referred to as one of proteins (F3-1) to (F3-46).

The protein (B1) can be a protein consisting of at least one amino acid sequence selected from the group consisting of SEQ ID NOs: 2, 4, 7, 10, 11, 13, and 34 to 67, for example. Regarding the protein (B1) consisting of at least one of the above-described amino acid sequences, reference can be made to the description as to the protein (F1) consisting of at least one of the above-described amino acid sequences.

The amino acid sequences of SEQ ID NOs: 2 to 13 and 34 to 67 of the protein (F1) are as follows. The amino acid sequences of SEQ ID NOs: 2 to 13 respectively correspond to the combinations (aa1) to (aa12) of the $Xaa_{52}$, the $Xaa_{133}$, and the $Xaa_{154}$ in the amino acid sequence of SEQ ID NO: 1. The amino acid sequences of SEQ ID NOs: 34 to 48 correspond to the combination (aa1) of the $Xaa_{52}$, the $Xaa_{133}$, and the $Xaa_{154}$ in the amino acid sequence of SEQ ID NO: 1. The amino acid sequences of SEQ ID NOs: 49 to 67 correspond to the combination (aa9) of the $Xaa_{52}$, the $Xaa_{133}$, and the $Xaa_{154}$ in the amino acid sequence of SEQ ID NO: 1.

```
Amino acid sequence of (F1-1)
                                                      (SEQ ID NO: 2)
MTTFKIESRIHGNLNGEKFELVGGGVGEEGRLEIEMKTKDKPLAFSPFLLSTCMGYGFYH

FASFPKGTKNIYLHAATNGGYTNTRKEIYEDGGILEVNFRYTYEFNKIIGDVECIGHGFPS

QSPIFKDTIVKSCPTVDLMLPMSGNIIASSYAYAFQLKDGSFYTAEVKNNIDFKNPIHESFS

KSGPMFTHRRVEETHTKENLAMVEYQQVFNSAPRDM

Amino acid sequence of (F1-2)
                                                      (SEQ ID NO: 3)
MTTFKIESRIHGNLNGEKFELVGGGVGEEGRLEIEMKTKDKPLAFSPFLLSHCMGYGFY

HFASFPKGTKNIYLHAATNGGYTNTRKEIYEDGGILEVNFRYTYEFNKIIGDVECIGHGFP

SQSPIFKDTIVKTCPTVDLMLPMSGNIIASSYAKAFQLKDGSFYTAEVKNNIDFKNPIHES

FSKSGPMFTHRRVEETHTKENLAMVEYQQVFNSAPRDM

Amino acid sequence of (F1-3)
                                                      (SEQ ID NO: 4)
MTTFKIESRIHGNLNGEKFELVGGGVGEEGRLEIEMKTKDKPLAFSPFLLSCCMGYGFY

HFASFPKGTKNIYLHAATNGGYTNTRKEIYEDGGILEVNFRYTYEFNKIIGDVECIGHGFP
```

SQSPIFKDTIVKLCPTVDLMLPMSGNIIASSYALAFQLKDGSFYTAEVKNNIDFKNPIHESF

SKSGPMFTHRRVEETHTKENLAMVEYQQVFNSAPRDM

Amino acid sequence of (F1-4)
(SEQ ID NO: 5)
MTTFKIESRIHGNLNGEKFELVGGGVGEEGRLEIEMKTKDKPLAFSPFLLSCCMGYGFY

HFASFPKGTKNIYLHAATNGGYTNTRKEIYEDGGILEVNFRYTYEFNKIIGDVECIGHGFP

SQSPIFKDTIVKSCPTVDLMLPMSGNIIASSYAHAFQLKDGSFYTAEVKNNIDFKNPIHES

FSKSGPMFTHRRVEETHTKENLAMVEYQQVFNSAPRDM

Amino acid sequence of (F1-5)
(SEQ ID NO: 6)
MTTFKIESRIHGNLNGEKFELVGGGVGEEGRLEIEMKTKDKPLAFSPFLLSTCMGYGFYH

FASFPKGTKNIYLHAATNGGYTNTRKEIYEDGGILEVNFRYTYEFNKIIGDVECIGHGFPS

QSPIFKDTIVKSCPTVDLMLPMSGNIIASSYAHAFQLKDGSFYTAEVKNNIDFKNPIHESF

SKSGPMFTHRRVEETHTKENLAMVEYQQVFNSAPRDM

Amino acid sequence of (F1-6)
(SEQ ID NO: 7)
MTTFKIESRIHGNLNGEKFELVGGGVGEEGRLEIEMKTKDKPLAFSPFLLSMCMGYGFY

HFASFPKGTKNIYLHAATNGGYTNTRKEIYEDGGILEVNFRYTYEFNKIIGDVECIGHGFP

SQSPIFKDTIVKLCPTVDLMLPMSGNIIASSYAVAFQLKDGSFYTAEVKNNIDFKNPIHESF

SKSGPMFTHRRVEETHTKENLAMVEYQQVFNSAPRDM

Amino acid sequence of (F1-7)of
(SEQ ID NO: 8)
MTTFKIESRIHGNLNGEKFELVGGGVGEEGRLEIEMKTKDKPLAFSPFLLSFCMGYGFYH

FASFPKGTKNIYLHAATNGGYTNTRKEIYEDGGILEVNFRYTYEFNKIIGDVECIGHGFPS

QSPIFKDTIVKSCPTVDLMLPMSGNIIASSYAQAFQLKDGSFYTAEVKNNIDFKNPIHESF

SKSGPMFTHRRVEETHTKENLAMVEYQQVFNSAPRDM

Amino acid sequence of (F1-8)
(SEQ ID NO: 9)
MTTFKIESRIHGNLNGEKFELVGGGVGEEGRLEIEMKTKDKPLAFSPFLLSKCMGYGFY

HFASFPKGTKNIYLHAATNGGYTNTRKEIYEDGGILEVNFRYTYEFNKIIGDVECIGHGFP

SQSPIFKDTIVKTCPTVDLMLPMSGNIIASSYAAAFQLKDGSFYTAEVKNNIDFKNPIHES

FSKSGPMFTHRRVEETHTKENLAMVEYQQVFNSAPRDM

Amino acid sequence of (F1-9)
(SEQ ID NO: 10)
MTTFKIESRIHGNLNGEKFELVGGGVGEEGRLEIEMKTKDKPLAFSPFLLSCCMGYGFY

HFASFPKGTKNIYLHAATNGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETHTKENLAMVEYQQVFNSAPRDM

Amino acid sequence of (F1-10)
(SEQ ID NO: 11)
MTTFKIESRIHGNLNGEKFELVGGGVGEEGRLEIEMKTKDKPLAFSPFLLSTCMGYGFYH

FASFPKGTKNIYLHAATNGGYTNTRKEIYEDGGILEVNFRYTYEFNKIIGDVECIGHGFPS

QSPIFKDTIVKLCPTVDLMLPMSGNIIASSYAIAFQLKDGSFYTAEVKNNIDFKNPIHESFS

KSGPMFTHRRVEETHTKENLAMVEYQQVFNSAPRDM

Amino acid sequence of (F1-11)
(SEQ ID NO: 12)
MTTFKIESRIHGNLNGEKFELVGGGVGEEGRLEIEMKTKDKPLAFSPFLLSKCMGYGFY

HFASFPKGTKNIYLHAATNGGYTNTRKEIYEDGGILEVNFRYTYEFNKIIGDVECIGHGFP

SQSPIFKDTIVKSCPTVDLMLPMSGNIIASSYAQAFQLKDGSFYTAEVKNNIDFKNPIHES

FSKSGPMFTHRRVEETHTKENLAMVEYQQVFNSAPRDM

Amino acid sequence of (F1-12)
(SEQ ID NO: 13)
MTTFKIESRIHGNLNGEKFELVGGGVGEEGRLEIEMKTKDKPLAFSPFLLSMCMGYGFY

HFASFPKGTKNIYLHAATNGGYTNTRKEIYEDGGILEVNFRYTYEFNKIIGDVECIGHGFP

SQSPIFKDTIVKLCPTVDLMLPMSGNIIASSYAAAFQLKDGSFYTAEVKNNIDFKNPIHES

FSKSGPMFTHRRVEETHTKENLAMVEYQQVFNSAPRDM

Amino acid sequence of (F1-13)
(SEQ ID NO: 34)
MTTFKIESRIHGNLNGEKFELVGGGVGEEGRLEIEMKTKDKPLAFSPFLLSTCMGYGFY

FASFPKGTKNIYLHAATNGGYTNTRKEIYEDGGILEVNFRYTYEFNKIIGDVECIGHGFPS

SQSPIFKDTIVKSCPTVDLMLPMSGNIIASSYAVAFQLKDGSFYTAEVKNNIDFKNPIHES

KSGPMFTHRRVEETHTKENLAIVEYQQVFNSAPRDM

Amino acid sequence of (F1-14)
(SEQ ID NO: 35)
MTTFKIESRIHGNLNGEKFELVGGGVGEEGRLEIEMKTKDKPLAFSPFLLSTCMGYGFYH

FASFPKGTKNIYLHAATNGGYTNTRKEIYEDGGILEVNFRYTYEFNKIIGDVECIGHGFPS

QSPIFKDTIVKSCPTVDLMLPMSGNIIASSYAVAFQLKDGSFYTAEVKNNIDFKNPIHESFS

KSGPMFTHRRVEETLTKENLAIVEYQQVFNSAPRDM

Amino acid sequence of (F1-15)
(SEQ ID NO: 36)
MTTFKIESRIHGNLNGEKFELVGGGVGEEGRLEIEMKTKDKPLAFSPFLLSTCMGYGFYH

FASFPKGTKNIYLHAATNGGYTNTRKEIYEDGGILEVNFRYTYEFNKIIGDVECIGHGFPS

QSPIFKDTIVKSCPTVDLMLPMSGNIIASSYAVAFQLKDGSFYTAEVKNNIDFKNPIHESFL

KSGPMFTHRRVEETLTKENLAIVEYQQVFNSAPRDM

Amino acid sequence of (F1-16)
(SEQ ID NO: 37)
MTTFKIESRIHGNLNGEKFELVGGGVGEEGRLEIEMKTKDKPLAFSPFLLSTCMGYGFYH

FASFPKGTKNIYLHAATNGGYTNTRKEIYEDGGILEVNFRYTYEFNKIIGDVECIGHGFPS

QSPIFKDTIVK[S]CPTVDLMLPMPGNIIASSYA[V]AFQLKDGSFYTAEVKNNIDFKNPIHESFS

KSGPMFTHRRVEET[L]TKENLA[I]VEYQQVFNSAPRDM

Amino acid sequence of (F1-17)

(SEQ ID NO: 38)

MTTFKIESRIHGNLNGEKFELVGGGVGEEGRLEIEMKTKDKPLAFSPPFLLS[T]CMGYGFYH

FASFPKGIKNIYLHAATNGGYTNTRKEIYEDGGILEVNFRYTYEFNKIIGDVECIGHGFPSQ

SPIFKDTIVK[S]CPTVDLMLPMSGNIIASSYA[V]AFQLKDGSFYTAEVKNNIDFKNPIHESFSK

SGPMFTHRRVEET[L]TKENLA[I]VEYQQVFNSAPRDM

Amino acid sequence of (F1-18)

(SEQ ID NO: 39)

MTTFKIESRIHGNLNGEKFELVGGGVGEEGRLEIEMKTKDKPLAFSPPFLLT[T]CMGYGFYH

FASFPKGTKNIYLHAATNGGYTNTRKEIYEDGGILEVNFRYTYEFNKIIGDVECIGHGFPS

QSPIFKDTIVK[S]CPTVDLMLPMSGNIIASSYA[V]AFQLKDGSFYTAEVKNNIDFKNPIHESFS

KSGPMFTHRRVEET[L]TKENLA[I]VEYQQVFNSAPRDM

Amino acid sequence of (F1-19)

(SEQ ID NO: 40)

MTTFKIESRIHGNLNGEKFELVGGGVGEEGRLEIEMKTKDKPLAFSPPFLLS[T]CMGYGFYH

FASFPKGTKNIYLHAATNGGYTNTRKEIYEDGGILEVNFRYTYEFNKIIGDVECIGHGFPS

QSPIFKDTIVK[S]CPTVDLMLPMSGNIIVSSYA[V]AFQLKDGSFYTAEVKNNIDFKNPIHESFS

KSGPMFTHRRVEET[L]TKENLA[I]VEYQQVFNSAPRDM

Amino acid sequence of (F1-20)

(SEQ ID NO: 41)

MTTFKIESRIHGNLNGEKFELVGGGVGEEGRLEIEMKTKDKPLAFSPPFLLS[T]CMGYGFYH

FASFPKGTKNIYLHAATNGGYTNTRKEIYEDGGILEVNFRYTYEFNKIIGDVECIGHGFPS

QSPIFKDTIVK[S]CPTVDLMLPMTGNIITSSYA[V]AFQLKDGSFYTAEVKNNIDFKNPIHESFS

KSGPMFTHRRVEET[L]TKENLA[I]VEYQQVFNSAPRDM

Amino acid sequence of (F1-21)

(SEQ ID NO: 42)

MTTFKIESRIHGNLNGEKFELVGGGVGEEGRLEIEMRTKDKPLAFSPPFLLS[T]CMGYGFYH

FASFPKGTKNIYLHAATNGGYTNTRKEIYEDGGILEVNFRYTYEFNKIIGDVECIGHGFPS

QSPIFKDTIVK[S]CPTVDLMLPMSGNIIVSSYA[V]AFQLKDGTFYTAEVKNNIDFKNPIHESFS

KSGPMFTHRRVEET[L]TKENLA[I]VEYQQVFNSAPRDM

Amino acid sequence of (F1-22)

(SEQ ID NO: 43)

MTTFKIESRIHGNLNGEEFELVGGGVGEEGRLEIEMKTKDKPLAFSPPFLLS[T]CMGYGFYH

FASFPKGTKNIYLHAATNGGYTNTRKEIYEDGGILEVNFRYTYEFNKIIGDVECIGHGFPS

QSPIFKDTIVK[S]CPTVDLMLPMPGNIIASSYA[V]AFQLKDGSFYTAEVKNNIDFKNPIHESFS

KSGPMFTHRRVEET[L]TKENLA[I]VEYQQVFNSAPRDM

-continued

Amino acid sequence of (F1-23)
(SEQ ID NO: 44)
MTTFKIESRIHGNLNGEEFELVGGGVGEEGRLEIEMKTKDKPLAFSPFLLST̲CMGYGFYH

FASFPKGIKNIYLHAATNGGYTNTRKEIYEDGGILEVNFRYTYEFNKIIGDVECIGHGFPSQ

SPIFKDTIVKS̲CPTVDLMLPMSGNIIASSYAV̲AFQLKDGSFYTAEVKNNIDFRNPIHESFSK

SGPMFTHRRVEETL̲TKENLAI̲VEYQQVFNSAPRDM

Amino acid sequence of (F1-24)
(SEQ ID NO: 45)
MTTFKIESRIHGNLNGEKFELVGGGVGEEGRLEIEMKTKDKPLAFSPFLLST̲CMGYGFYH

FASFPKGIKNIYLHAATNGGYTNTRKEIYEDGGVLEVNFRYTYEFDKIIGDVECIGHGFPS

QSPIFKDTIVKS̲CPTVDLMLPMSGNIIASSYAV̲AFQLKDGSFYTAEVKNNIDFKNPIHESFS

KSGPMFTHRRVEETL̲TKENLAI̲VEYQQVFNSAPRDM

Amino acid sequence of (F1-25)
(SEQ ID NO: 46)
MTTFKIESRIHGNLNGEKFELVGGGVGEEGRLEIEMKTKDKPLAFSPFLLST̲CMGYGFYH

FASFPKGTKNIYLHAATNGGYTNTRKEIYEDGGILEVNFRYTYEFDKIIGDVECIGHGFPS

QSPIFKDTIVKS̲CPTVDLMLPMSGNIIASSYAV̲AFQLKDGSFYTAEVKNNIDFKNPIHESFL

KSGPMFTHRRVEETL̲TKENLAI̲VEYQQVFNSAPRDM

Amino acid sequence of (F1-26)
(SEQ ID NO: 47)
MTTFKIESRIHGNLNGEKFELVGGGVGEEGRLEIEMKTKDKPLAFSPFLLST̲SMGYGFYH

FASFPKGTKNIYLHAATNGGYTNTRKEIYEDGGILEVNFRYTYEFNKIIGDVECIGHGFPS

QSPIFKDTIVKS̲CPTVDLMLPMSGNIIASSYAV̲AFQLKDGSFYTADVKNNIDFKNPIHESFS

KSGPMFTHRRVEETL̲TKENLAI̲VEYQQVFNSAPRDM

Amino acid sequence of (F1-27)
(SEQ ID NO: 48)
MTTFKIESRIHGNLNGEKFELVGGGVGEEGRLEIEMKTKDKPLAFSPFLLTT̲CMGYGFYH

FASFPKGIKNIYLHAATNGGYTNTRKEIYEDGGILEVNFRYTYEFNKIIGDVECIGHGFPSQ

SPIFKDTIVKS̲CPTVDLMLPMSGNIIASSYAV̲AFQLKDGSFYTAEVKNNIDFKNPIHESFSK

SGPMFTHRRVEETL̲TKENLAI̲VEYQQVFNSAPRDM

Amino acid sequence of (F1-28)
(SEQ ID NO: 49)
MTTFKIESRIHGNLNGEKFELVGGGVGEEGRLEIEMKTKDKPLAFSPFLLSC̲CMGYGFY

HFASFPKGTKNIYLHAATNGGYTNTRKEIYEDGGILEVNFRYTYEFNKIIGDVECIGHGFP

SQSPIFKDTIVKQ̲CPTVDLMLPMSGNIIASSYAL̲AFQLKDGSFYTAEVKNNIDFKNPIHES

FSKSGPMFTHRRVEETY̲TKENLAM̲VEYQQVFNSAPRDM

Amino acid sequence of (F1-29)
(SEQ ID NO: 50)
MTTFKIESRIRGNLNGEKFELVGGGVGEEGRLEIEMKTKDKPLAFSPFLLSC̲CMGYGFYH

FASFPKGTKNIYLHAATNGGYTNTRKEIYEDGGILEVNFRYTYELNKIIGDVECIGHGFPS

QSPIFKDTIVKQCPTVDLMLPMSGNIIASSYALAFRLKDGSFYTAEVKNNIDFKNPIHESF

SKSGPMFTHRRVEETYTKENLAMVEYQQVFNSAPRDM

Amino acid sequence of (F1-30)

(SEQ ID NO: 51)
MTTFKIESRIHGNLNGEKFELVGGGVGEEGRLEIEMKTKDKPLAFSPFLLSCCMGYGFY

HFASFPKGTKNIYLHAATNGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTYRRVEETYTKENLAMVEYQQVFNSAPRDM

Amino acid sequence of (F1-31)

(SEQ ID NO: 52)
MTTFKIESRIHGNLNGEKFELVGGGVGEEGRLEIEMKTKDKPLAFSPFLLSCCMGYGFY

HFASFPKGTKNIYLHAATNGGYTNTRKEIYEDGGILEVNFRYTYEFNKIIGDVECIGHGFP

SQSPIFKDTIVKQCPTVDLMLPVSGNIIASSYALAFQLKDGSFYTAEVKNNIDFKNPIHESF

SKSGPMFTHRRVEETYTKENLAMVEYQQVFNSAPRDM

Amino acid sequence of (F1-32)

(SEQ ID NO: 53)
MTTFKIESRIHGNLNGEKFELVGGGVGEEGRLEIEMKTKDKPLAFSPFLLSCCMGYGFY

HFASFPKGTENIYLHAATHGGYTNTRKEIYEDGGILEVNFRYTYEFNKIIGDVECIGHGFP

SQSPIFKDTIVRQCPTVDLMLPVSGNIIASSYALAFQLKDGSFYTAEVKNNIDFKNPIHESF

SKSGPMFTHRRVEETYTKENLAMVEYQQVFNSAPRDM

Amino acid sequence of (F1-33)

(SEQ ID NO: 54)
MTTFKIESRIHGNLNGEKFELVGGGVGEEGRLEIEMKTKDKPLAFSPFLLSCCMGYGFY

HFASFPKGAKNIYLHAATNGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETHTKENLAIVEYQQVFNSAPRDM

Amino acid sequence of (F1-34)

(SEQ ID NO: 55)
MTTFKIESRIHGNLNGEKFELVGGGVGEEGRLEIEMKTKDKPLAFSPFLLSCCMGYGFY

HFASFPKGTKNIYLHAATNGGYTNTRKEIYEDGGILEVNFRYTYEFNKIIGDVECIGHGFP

SQSPIFKDTIVKQCPTVDLMLPMSGNIIASSYALAFQLRDGSFYTAEVKNNIDFKNPIHES

FSKSGPMFTHRRVEETYTKENLAMVEYQQVFNSAPRDM

Amino acid sequence of (F1-35)

(SEQ ID NO: 56)
MTTFKIESRIHGNLNGEKFELVGGGVGEEGRLEIEMKTKDKPLAFSPFLLSCCMGYGFY

HFASFPKGTKNIYLHAATNGGYTNTRKEIYEDGGILEVNFRYTYEFNKIIGDVECIGHGFP

SQSPIFKDTIVKQCPTVDLMLPVSRNIIASSYALAFQLKDGSFYTAEVKNNIDFKNPIHESF

SKSGPMFTHRRVEETYTKENLAMVEYQQVFNSAPRDM

-continued

Amino acid sequence of (F1-36)
(SEQ ID NO: 57)
MTTFKIESRIHGNLNGEKFELVGGGVGEEGRLEIEMKTKDKPLAFSPFFLLSCCMGYGFY

HFASFPKGTKNIYLHAATNGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETYTKENLAMVEYQQVFNSAPRDV

Amino acid sequence of (F1-37)
(SEQ ID NO: 58)
MTTFKIESRIHGNLNGEKFELVGGGVGEEGRLEIEMKTKDKPLAFSPFFLLSCCMGYGFY

HFASFPKGTENIYLHAATHGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETYTKENLAMVEYQQVFNSAPRDM

Amino acid sequence of (F1-38)
(SEQ ID NO: 59)
MTTFKIESRIHGNLNGEKFELVGGGVGEEGRLEIEMKTKDKPLAFSPFFLLSCCMGYGFY

HFASFPKGTKNIYLHAATNGGYTNTRKEIYEDGGILEVNFRYTYEFNKIIGDVECIGHGFP

SQSPIFKDTIVKQYPTVDLMLPMSGNIIASSYALAFQLKDGSFYTAEVKNNIDFKNPIHES

FSKSGPMFTHRRVEETHTKENLAIVEYQQVFNSAPRDM

Amino acid sequence of (F1-39)
(SEQ ID NO: 60)
MTTFKIESRIHGNLNGEKFELVGGGVGEEGRLEIEMKTKDKPLAFSPFFLLSCCMGYGFY

HFASFPKGTENIYLHAATNGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETYTKENLAMVEYQQVFNSAPRDM

Amino acid sequence of (F1-40)
(SEQ ID NO: 61)
MTTFKIESRIQGNLNGEKFELVGGGVGEEGRLEIEMKTKDKPLAFSPFFLLSCCMGYGFY

HFASFPKGTENIYLHAATNGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETYTKENLAMVEYQQVFNSAPRDM

Acid sequence of (F1-41)
(SEQ ID NO: 62)
MTTFKIESRIQGNLNGEKFELVGGGVGEEGRLEIEMKTKDKPLAFSPFFLLSCCMGYGFY

HFASFPKGTENIYLHAATNGGYTNTRKEIYEDGGILEVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETHTKENLAIVEYQQVFNSAPRDI

Amino acid sequence of (F1-42)
(SEQ ID NO: 63)
MTTFKIESRIHGNLNGEKFELVGGGVGEEGRLEIEMKTKDKPLAFSPFFLLSCCMGYGFY

HFASFPKGTENIYLHAATNGGYTNTRKEIYEDGGILEVNFRYTYEFNKIIGDVECIGHGFP

```
SQSPIFKDTIVKQWPTVDLMLPMSGNIIASSYALAFQLKDGSFYTAEVKNNIDFKNPIHES

FSKSGPMFTHRRVEETHTKENLAIVEYQQVFNSAPRDM

Amino acid sequence of (F1-43)
                                                     (SEQ ID NO: 64)
MTTFKIESRIHGNLNGEKFELVGGGVGEEGRLEIEMKTKDKPLAFSPFLLSCCMGYGFY

HFASFPKGTENIYLHAATNGGYTNTRKEIYEDGGILEVNFRYTYEFNKIIGDVECIGHGFP

SQSPIFKDTIVKQWPTVDLMLPMSGNIIASSYALAFQLKDGSFYTAEVKNNIDFKNPIHES

FSKSGPMFTHRRVEETHTKENLAMVEYQQVFNSAPRDM

Amino acid sequence of (F1-44)
                                                     (SEQ ID NO: 65)
MTTFKIESRIQGNLNGEKFELVGGGVGEEGRLEIEMKTKDKPLAFSPFLLSCCMGYGFY

HFASFPKGTENIYLHAATNGGYTNTRKEIYEDGGILKVNFRYTYEFNKIIGDVECIGHGFP

SQSPIFKDTIVKQCPTVDLMLPMSGNIIASSYALAFQLKDGSFYTAEVKNNIDFKNPIHES

FSKSGPMFTHRRVEETYTKENLAMVEYQQVFNSAPRDM

Amino acid sequence of (F1-45)
                                                     (SEQ ID NO: 66)
MTTFKIESRIQGNLNGEKFELVGGGVGEEGRLEIEMKTKDKPLAFSPFLLSCCMGYGFY

HFASFPKGTENIYLHAATNGGYTNTRKEIYEDGGILEVNFRYTYEFNKIIGDVECIGHGFP

SQSPIFKDTIVKQCPTVDLMLPMSGNIIASSYALAFQLEDGSFYTAEVKNNIDFKNPIHESF

SKSGPMFTHRRVEETYTKENLAMVEYQQVFNSAPRDM

Amino acid sequence of (F1-46)
                                                     (SEQ ID NO: 67)
MTTFKIESRIRGNLNGEKFELVGGGVGEEGRLEIEMKTKDKPLAFSPFLLSCCMGYGFYH

FASFPKGTENIYLHAATNGGYTNTRKEIYEDGGILEVNFRYTYEFNKIIGDVECIGHGFPS

QSPIFKDTIVKQCPTVDLMLPMSGNIIASSYALAFQLKDGSFYTAEVKNNIDFKNPIHESF

SKSGPMFTHRRVEETYTKENLAMVEYQQVFNSAPRDM
```

It can be said that the protein (F2) is, for example, a protein having a fluorescence activity and consisting of an amino acid sequence obtained by deletion, substitution, insertion, and/or addition of one to several amino acids in the amino acid sequence of the protein (F1) in which the $Xaa_{52}$, the $Xaa_{133}$, and the $Xaa_{154}$ are preserved. In the protein (F2), "one to several" can be a range in which the protein (F2) has the fluorescence activity, for example. In the amino acid sequence of the protein (F2), "one to several" is, for example, 1 to 43, 1 to 33, 1 to 22, 1 to 11, 1 to 9, 1 to 7, 1 to 5, 1 to 3, 1, or 2. In the present invention, for example, the numerical range regarding the number of bases discloses all the positive integers falling within that range. That is, for example, the description "1 to 5 bases" discloses all of "1, 2, 3, 4, and 5 bases" (hereinafter, the same applies). When the $Xaa_{205}$ is substituted with I in the protein (F1), the protein (F2) is preferably a protein in which the $Xaa_{205}$ of the protein (F1) is preserved. In this case, the protein (F2) can be, for example, a protein having a fluorescence activity and consisting of an amino acid sequence obtained by deletion, substitution, insertion, and/or addition of one to several amino acids in the amino acid sequence of the protein (F1) in which the $Xaa_{52}$, the $Xaa_{133}$, the $Xaa_{154}$, and the $Xaa_{205}$ are preserved. When the $Xaa_{198}$ is substituted with L or H in the protein (F1), the protein (F2) is preferably a protein in which the $Xaa_{198}$ of the protein (F1) is preserved. In this case, the protein (F2) can be, for example, a protein having a fluorescence activity and consisting of an amino acid sequence obtained by deletion, substitution, insertion, and/or addition of one to several amino acids in the amino acid sequence of the protein (F1) in which the $Xaa_{52}$, the $Xaa_{133}$, the $Xaa_{154}$, and the $Xaa_{198}$ are preserved. When the $Xaa_{198}$ and the $Xaa_{205}$ are substituted with L and I or H and I, respectively in the protein (F1), the protein (F2) is preferably a protein in which the $Xaa_{198}$ and the $Xaa_{205}$ of the protein (F1) are preserved. In this case, the protein (F2) can be, for example, a protein having a fluorescence activity and consisting of an amino acid sequence obtained by deletion, substitution, insertion, and/or addition of one to several amino acids in the amino acid sequence of the protein (F1) in which the $Xaa_{52}$, the $Xaa_{133}$, the $Xaa_{154}$, the $Xaa_{198}$, and the $Xaa_{205}$ are preserved. Regarding the "one to several", reference can be made to the above description.

It can be said that the protein (F3) can be a protein having a fluorescence activity and consisting of an amino acid sequence having at least 80% identity to the protein (F1) in which the $Xaa_{52}$, the $Xaa_{133}$, and the $Xaa_{154}$ are preserved. In the protein (F3), "identity" can be a range in which the protein (F3) has the fluorescence activity, for example. In the amino acid sequence of the protein (F3), "identity" is, for example, at least 80%, at least 85%, at least 90%, at least 95%, at least 96%, at least 97%, at least 98%, or at least 99%. The "identity" can be calculated with analysis software such as BLAST or FASTA using default parameters, for example (hereinafter, the same applies). When the $Xaa_{205}$ is substituted with I in the protein (F1), the protein (F3) is preferably a protein in which the $Xaa_{205}$ of the protein (F1) is preserved. In this case, the protein (F3) can be, for example, a protein having a fluorescence activity and consisting of an amino acid sequence having at least 80% identity to the amino acid sequence of the protein (F1) in which the $Xaa_{52}$, the $Xaa_{133}$, the $Xaa_{154}$, and the $Xaa_{205}$ are preserved. When the $Xaa_{198}$ is substituted with L or H in the protein (F1), the protein (F3) is preferably a protein in which the $Xaa_{198}$ of the protein (F1) is preserved. In this case, the protein (F3) can be, for example, a protein having a fluorescence activity and consisting of an amino acid sequence having at least 80% identity to the amino acid sequence of the protein (F1) in which the $Xaa_{52}$, the $Xaa_{133}$, the $Xaa_{154}$, and the $Xaa_{198}$ are preserved. When the $Xaa_{198}$ and the $Xaa_{205}$ are substituted with L and I or H and I, respectively in the protein (F1), the protein (F3) is preferably a protein in which the $Xaa_{198}$ and the $Xaa_{205}$ of the protein (F1) are preserved. In this case, the protein (F3) can be, for example, a protein having a fluorescence activity and consisting of an amino acid sequence having at least 80% identity to the amino acid sequence of the protein (F1) in which the $Xaa_{52}$, the $Xaa_{133}$, the $Xaa_{154}$, the $Xaa_{198}$, and the $Xaa_{205}$ are preserved. Regarding the "identity", reference can be made to the above description.

The novel fluorescent protein of the present invention has, for example, the chemical properties described below. The excitation wavelength, excitation maximum wavelength, fluorescence wavelength, and fluorescence maximum wavelength described below are, for example, chemical properties in the wavelength range from 350 to 650 nm.
Excitation wavelength: 350 to 650 nm
Excitation maximum wavelength: 386 to 514 nm
Fluorescence wavelength: 350 to 650 nm
Fluorescence maximum wavelength: 506 to 524 nm When the novel fluorescent protein of the present invention is one of the proteins (F1-1) to (F1-46), the proteins (F1-1) to (F1-46) have, for example, the following chemical properties. When there are two or more maximum values for the fluorescence intensity in the excitation wavelength or the fluorescence wavelength in the proteins (F1-1) to (F1-46), two or more numerical ranges of the excitation maximum wavelength and the fluorescence maximum wavelength are described.

(F1-1)
Excitation wavelength: 350 to 560 nm
Excitation maximum wavelength: 396 to 404 nm
Fluorescence wavelength: 350 to 650 nm
Fluorescence maximum wavelength: 511 to 519 nm
(F1-2)
Excitation wavelength: 350 to 600 nm
Excitation maximum wavelength: 501 to 509 nm
Fluorescence wavelength: 350 to 650 nm
Fluorescence maximum wavelength: 511 to 519 nm
(F1-3)
Excitation wavelength: 350 to 620 nm
Excitation maximum wavelength: 396 to 404 nm, 506 to 514 nm
Fluorescence wavelength: 350 to 650 nm
Fluorescence maximum wavelength: 516 to 524 nm
(F1-4)
Excitation wavelength: 350 to 625 nm
Excitation maximum wavelength: 496 to 504 nm
Fluorescence wavelength: 350 to 650 nm
Fluorescence maximum wavelength: 511 to 519 nm
(F1-5)
Excitation wavelength: 350 to 615 nm
Excitation maximum wavelength: 501 to 509 nm
Fluorescence wavelength: 350 to 650 nm
Fluorescence maximum wavelength: 511 to 519 nm
(F1-6)
Excitation wavelength: 350 to 625 nm
Excitation maximum wavelength: 391 to 399 nm, 506 to 514 nm
Fluorescence wavelength: 350 to 650 nm
Fluorescence maximum wavelength: 516 to 524 nm
(F1-7)
Excitation wavelength: 350 to 625 nm
Excitation maximum wavelength: 476 to 484 nm
Fluorescence wavelength: 350 to 650 nm
Fluorescence maximum wavelength: 506 to 514 nm
(F1-8)
Excitation wavelength: 350 to 605 nm
Excitation maximum wavelength: 496 to 504 nm
Fluorescence wavelength: 350 to 650 nm
Fluorescence maximum wavelength: 511 to 519 nm
(F1-9)
Excitation wavelength: 350 to 615 nm
Excitation maximum wavelength: 401 to 409 nm, 496 to 504 nm
Fluorescence wavelength: 350 to 650 nm
Fluorescence maximum wavelength: 511 to 519 nm
(F1-10)
Excitation wavelength: 350 to 590 nm
Excitation maximum wavelength: 391 to 399 nm, 506 to 514 nm
Fluorescence wavelength: 350 to 650 nm
Fluorescence maximum wavelength: 516 to 524 nm
(F1-11)
Excitation wavelength: 350 to 575 nm
Excitation maximum wavelength: 476 to 484 nm
Fluorescence wavelength: 350 to 650 nm
Fluorescence maximum wavelength: 506 to 514 nm
(F1-12)
Excitation wavelength: 350 to 595 nm
Excitation maximum wavelength: 386 to 394 nm, 506 to 514 nm
Fluorescence wavelength: 350 to 650 nm
Fluorescence maximum wavelength: 516 to 524 nm
(F1-13)
Excitation wavelength: 350 to 650 nm
Excitation maximum wavelength: 396 to 404 nm
Fluorescence wavelength: 350 to 650 nm
Fluorescence maximum wavelength: 511 to 519 nm
(F1-14)
Excitation wavelength: 350 to 650 nm
Excitation maximum wavelength: 401 to 409 nm
Fluorescence wavelength: 350 to 650 nm
Fluorescence maximum wavelength: 511 to 519 nm (F1-15)
Excitation wavelength: 350 to 650 nm
Excitation maximum wavelength: 396 to 404 nm
Fluorescence wavelength: 350 to 650 nm
Fluorescence maximum wavelength: 511 to 519 nm
(F1-16)
Excitation wavelength: 350 to 650 nm
Excitation maximum wavelength: 391 to 399 nm
Fluorescence wavelength: 350 to 650 nm
Fluorescence maximum wavelength: 511 to 519 nm
(F1-17)
Excitation wavelength: 350 to 650 nm
Excitation maximum wavelength: 396 to 404 nm
Fluorescence wavelength: 350 to 650 nm
Fluorescence maximum wavelength: 511 to 519 nm
(F1-18)
Excitation wavelength: 350 to 650 nm
Excitation maximum wavelength: 396 to 404 nm
Fluorescence wavelength: 350 to 650 nm
Fluorescence maximum wavelength: 511 to 519 nm
(F1-19)
Excitation wavelength: 350 to 650 nm
Excitation maximum wavelength: 396 to 404 nm
Fluorescence wavelength: 350 to 650 nm
Fluorescence maximum wavelength: 511 to 519 nm
(F1-20)
Excitation wavelength: 350 to 650 nm
Excitation maximum wavelength: 391 to 399 nm
Fluorescence wavelength: 350 to 650 nm
Fluorescence maximum wavelength: 511 to 519 nm
(F1-21)
Excitation wavelength: 350 to 650 nm
Excitation maximum wavelength: 391 to 399 nm
Fluorescence wavelength: 350 to 650 nm
Fluorescence maximum wavelength: 511 to 519 nm
(F1-22)
Excitation wavelength: 350 to 650 nm
Excitation maximum wavelength: 396 to 404 nm
Fluorescence wavelength: 350 to 650 nm
Fluorescence maximum wavelength: 511 to 519 nm
(F1-23)
Excitation wavelength: 350 to 650 nm
Excitation maximum wavelength: 391 to 399 nm
Fluorescence wavelength: 350 to 650 nm
Fluorescence maximum wavelength: 511 to 519 nm
(F1-24)
Excitation wavelength: 350 to 645 nm
Excitation maximum wavelength: 396 to 404 nm
Fluorescence wavelength: 350 to 650 nm
Fluorescence maximum wavelength: 511 to 519 nm
(F1-25)
Excitation wavelength: 350 to 580 nm
Excitation maximum wavelength: 396 to 404 nm
Fluorescence wavelength: 350 to 650 nm
Fluorescence maximum wavelength: 511 to 519 nm
(F1-26)
Excitation wavelength: 350 to 560 nm
Excitation maximum wavelength: 396 to 404 nm
Fluorescence wavelength: 350 to 650 nm
Fluorescence maximum wavelength: 511 to 519 nm
(F1-27)
Excitation wavelength: 350 to 650 nm
Excitation maximum wavelength: 391 to 399 nm
Fluorescence wavelength: 350 to 650 nm
Fluorescence maximum wavelength: 511 to 519 nm
(F1-28)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-29)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-30)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-31)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-32)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-33)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-34)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-35)
Excitation wavelength: 350 to 650 nm
Excitation maximum wavelength: 406 to 414 nm, 496 to 504 nm
Fluorescence wavelength: 350 to 650 nm
Fluorescence maximum wavelength: 511 to 519 nm
(F1-36)
Excitation wavelength: 350 to 650 nm
Excitation maximum wavelength: 401 to 409 nm, 501 to 509 nm
Fluorescence wavelength: 350 to 650 nm
Fluorescence maximum wavelength: 511 to 519 nm
(F1-37)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-38)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm (F1-39)
Excitation wavelength: 350 to 650 nm
Excitation maximum wavelength: 416 to 424 nm, 496 to 504 nm
Fluorescence wavelength: 350 to 650 nm
Fluorescence maximum wavelength: 511 to 519 nm
(F1-40)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-41)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-42)
Excitation wavelength: 350 to 650 nm
Excitation maximum wavelength: 416 to 424 nm, 496 to 504 nm
Fluorescence wavelength: 350 to 650 nm
Fluorescence maximum wavelength: 511 to 519 nm
(F1-43)
Excitation wavelength: 350 to 650 nm
Excitation maximum wavelength: 421 to 429 nm, 501 to 509 nm
Fluorescence wavelength: 350 to 650 nm
Fluorescence maximum wavelength: 511 to 519 nm
(F1-44)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-45)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm
(F1-46)
Excitation wavelength: 350 to 650 nm
Excitation maximum wavelength: 401 to 409 nm, 496 to 504 nm
Fluorescence wavelength: 350 to 650 nm
Fluorescence maximum wavelength: 511 to 519 nm The methods for measuring the excitation wavelength, the excitation maximum wavelength, the fluorescence wavelength, and the fluorescence maximum wavelength are not limited to particular methods, and each wavelength can be measured according to JIS K0120, for example. For example, the excitation wavelength, the excitation maximum wavelength, the fluorescence wavelength, and the fluorescence maximum wavelength may be measured according to the methods described in Example 1.

The novel fluorescent protein only requires a fluorescence activity. For example, the novel fluorescent protein may also have other activities besides the fluorescence activity.

<Novel Gene>

The novel gene of the present invention has at least one polynucleotide selected from the group consisting of the following (f1) to (f7) as described below:
(f1) a polynucleotide consisting of a base sequence of SEQ ID NO: 14, wherein in the base sequence of SEQ ID NO: 14, a 154th base $N_{154}$, a 155th base $N_{155}$, and a 156th base $N_{156}$ form a codon (hereinafter, also referred to as a "$N_{154}N_{155}N_{156}$ codon") encoding an arbitrary amino acid, a 397th base $N_{397}$, a 398th base $N_{398}$, and a 399th base $N_{399}$ form a codon (hereinafter, also referred to as a "$N_{397}N_{398}N_{399}$ codon") encoding an arbitrary amino acid, and
a 460th base $N_{460}$, a 461st base $N_{461}$, and a 462nd base $N_{462}$ form a codon (hereinafter, also referred to as a "$N_{460}N_{461}N_{462}$ codon") encoding an arbitrary amino acid;
(f2) a polynucleotide encoding a protein having a fluorescence activity and consisting of a base sequence obtained by deletion, substitution, insertion, and/or addition of one to several bases in the base sequence of the polynucleotide (f1) excluding the 154th base $N_{154}$, the 155th base $N_{155}$, the 156th base $N_{156}$, the 397th base $N_{397}$, the 398th base $N_{398}$, the 399th base $N_{399}$, the 460th base $N_{460}$, the 461st base $N_{461}$, and the 462nd base $N_{462}$;
(f3) a polynucleotide encoding a protein having a fluorescence activity and consisting of a base sequence having at least 80% identity to the base sequence of the polynucleotide (f1) excluding the 154th base $N_{154}$, the 155th base $N_{155}$, the 156th base $N_{156}$, the 397th base $N_{397}$, the 398th base $N_{398}$, the 399th base $N_{399}$, the 460th base $N_{460}$, the 461st base $N_{461}$, and the 462nd base $N_{462}$;
(f4) a polynucleotide encoding a protein having a fluorescence activity and consisting of a base sequence complementary to a polynucleotide that hybridizes to a polynucleotide consisting of the base sequence of the polynucleotide (f1) under a stringent condition, wherein in the complementary sequence, the bases corresponding to the 154th base $N_{154}$, the 155th base $N_{155}$, the 156th base $N_{156}$, the 397th base $N_{397}$, the 398th base $N_{398}$, the 399th base $N_{399}$, the 460th base $N_{460}$, the 461st base $N_{461}$, and the 462nd base $N_{462}$ of the polynucleotide (f1) are preserved;
(f5) a polynucleotide encoding a protein consisting of an amino acid sequence of SEQ ID NO: 1, wherein
in the amino acid sequence of SEQ ID NO: 1,
the 52nd amino acid $Xaa_{52}$ is an arbitrary amino acid,
the 133rd amino acid $Xaa_{133}$ is an arbitrary amino acid, and
the 154th amino acid $Xaa_{154}$ is an arbitrary amino acid;
(f6) a polynucleotide encoding a protein having a fluorescence activity and consisting of an amino acid sequence obtained by deletion, substitution, insertion, and/or addition of one to several amino acids in the amino acid sequence of the polynucleotide (f5) excluding the 52nd amino acid $Xaa_{52}$, the 133rd amino acid $Xaa_{133}$, and the 154th amino acid $Xaa_{154}$; and
(f7) a polynucleotide encoding a protein having a fluorescence activity and consisting of an amino acid sequence having at least 80% identity to the base sequence of the polynucleotide (f5) excluding the 52nd amino acid $Xaa_{52}$, the 133rd amino acid $Xaa_{133}$, and the 154th amino acid $Xaa_{154}$.

Since the novel gene is a gene encoding the novel fluorescent protein of the present invention, hereinafter, it is also referred to as a novel fluorescent protein gene. The novel fluorescent protein gene may contain, for example, one type of polynucleotide or two or more types of polynucleotides (hereinafter, the same applies).

The base sequence of SEQ ID NO: 14 of the polynucleotide (f1) is described below. In the base sequence described below, the first base sequence (NNN) of three boxed base sequences is a base sequence corresponding to the $N_{154}N_{155}N_{156}$ codon, the second base sequence of three boxed base sequences is a base sequence corresponding to the $N_{397}N_{398}N_{399}$ codon, and the third base sequence of three boxed base sequences is a base sequence corresponding to the $N_{460}N_{461}N_{462}$ codon. In the base sequence described below, the first codon of two underlined codons is a codon corresponding to the 592nd base $N_{592}$, the 593rd base $N_{593}$, and the 594th base $N_{594}$ and the second codon of two underlined codons is a codon corresponding to the 613rd base $N_{613}$, the 614th base $N_{614}$, and the 615th base $N_{615}$.

```
Polynucleotide (f1)
                                           (SEQ ID NO: 14)
5'-ATGACAACCTTCAAAATCGAGTCCCGGATCCATGGCAACCTCAAC

GGGGAGAAGTTCGAGTTGGTTGGAGGTGGAGTAGGTGAGGAGGGTCGC

CTCGAGATTGAGATGAAGACTAAAGATAAACCACTGGCATTCTCTCCC

TTCCTGCTGTCCNNNTGCATGGGTTACGGGTTCTACCACTTCGCCAGC

TTCCCAAAGGGGACTAAGAACATCTATCTTCATGCTGCAACAAACGGA

GGTTACACCAACACCAGGAAGGAGATCTATGAAGACGGCGGCATCTTG

GAGGTCAACTTCCGTTACACTTACGAGTTCAACAAGATCATCGGTGAC

GTCGAGTGCATTGGACATGGATTCCCAAGTCAGAGTCCGATCTTCAAG

GACACGATCGTGAAGNNNTGTCCCACGGTGGACCTGATGTTGCCGATG

TCCGGGAACATCATCGCCAGCTCCTACGCTNNNGCCTTCCAACTGAAG

GACGGCTCTTTCTACACGGCAGAAGTCAAGAACAACATAGACTTCAAG

AATCCAATCCACGAGTCCTTCTCGAAGTCGGGGCCCATGTTCACCCAC

AGACGTGTCGAGGAGACTCACACCAAGGAGAACCTTGCCATGGTGGAG

TACCAGCAGGTTTTCAACAGCGCCCCAAGAGACATGTAG-3'
```

In the polynucleotide (f1), the $N_{154}N_{155}N_{156}$ codon is a codon encoding an arbitrary amino acid. The codon encoding an arbitrary amino acid is a codon encoding A, C, D, E, F, G, H, I, K, L, M, N, P, Q, R, S, T, V, W, or Y, is preferably a codon encoding C, F, H, K, M, or T, and is more preferably a codon encoding C, M, or T as it shows stronger fluorescence even with excitation light having a relatively low wavelength, for example. In the polynucleotide (f1), the $N_{154}N_{155}N_{156}$ codon is more preferably a codon encoding H as it shows stronger fluorescence under excitation with excitation light at the same intensity, for example.

In the polynucleotide (f1), the $N_{397}N_{398}N_{399}$ codon is a codon encoding an arbitrary amino acid. The codon encoding an arbitrary amino acid is a codon encoding A, C, D, E, F, G, H, I, K, L, M, N, P, Q, R, S, T, V, W, or Y and is preferably a codon encoding L, Q, S, or T. In the polynucleotide (f1), the $N_{397}N_{398}N_{399}$ codon is more preferably a codon encoding T as it shows stronger fluorescence under excitation with excitation light at the same intensity, for example.

In the polynucleotide (f1), the $N_{460}N_{461}N_{462}$ codon is a codon encoding an arbitrary amino acid. The codon encoding an arbitrary amino acid is a codon encoding A, C, D, E, F, G, H, I, K, L, M, N, P, Q, R, S, T, V, W, or Y, is preferably a codon encoding A, H, I, K, L, Q, V, or Y, and is more preferably a codon encoding A, I, L, V, or Y as it shows stronger fluorescence even with excitation light having a relatively low wavelength, for example. In the polynucleotide (f1), the $N_{460}N_{461}N_{462}$ codon is more preferably a codon encoding K as it shows stronger fluorescence under excitation with excitation light at the same intensity, for example.

In the polynucleotide (f1), the combination of the $N_{154}N_{155}N_{156}$ codon, the $N_{397}N_{398}N_{399}$ codon, and the $N_{460}N_{461}N_{462}$ codon is not limited to particular combinations, and is for example, as follows:
the $N_{154}N_{155}N_{156}$ codon is a codon encoding C, F, H, K, M, or T;
the $N_{397}N_{398}N_{399}$ codon is a codon encoding L, Q, S, or T; and
the $N_{460}N_{461}N_{462}$ codon is a codon encoding A, H, I, K, L, Q, V, or Y.

In the polynucleotide (f1), the combination of the $N_{154}N_{155}N_{156}$ codon, the $N_{397}N_{398}N_{399}$ codon, and the $N_{460}N_{461}N_{462}$ codon is preferably as follows, for example, as the novel fluorescent protein encoded by the novel fluorescent protein gene shows stronger fluorescence even with excitation light having a relatively low wavelength:
the $N_{154}N_{155}N_{156}$ codon is a codon encoding C, M, or T;
the $N_{397}N_{398}N_{399}$ codon is a codon encoding L, Q, S, or T; and
the $N_{460}N_{461}N_{462}$ codon is a codon encoding A, I, L, V, or Y.

In the description below, in the case where the polynucleotide (f1) includes the $Xaa_{52}$, the $Xaa_{133}$, and the $Xaa_{154}$ in such a combination, the polynucleotide (f1) is also referred to as polynucleotide (b1), and the polynucleotides (f2) to (f4) are also referred to as polynucleotides (b2) to (b4) when the polynucleotide (f1) is the polynucleotide (b1). Also in the description below, regarding the polynucleotides (b2) to (b4), for example, reference can be made to the description as to the polynucleotides (f2) to (f4) by replacing (f1) with (b1), (f2) with (b2), (f3) with (b3), and (f4) with (b4), respectively.

As a specific example, in the novel fluorescent protein gene of the present invention, the combination of the $N_{154}N_{155}N_{156}$ codon, the $N_{397}N_{398}N_{399}$ codon, and the $N_{460}N_{461}N_{462}$ codon is, for example, the combination of codons encoding one of the following amino acid combinations (aa1') to (aa12'). In the novel fluorescent protein gene of the present invention, the combination of the $N_{154}N_{155}N_{156}$ codon, the $N_{397}N_{398}N_{399}$ codon, and the $N_{460}N_{461}N_{462}$ codon is preferably the combination of codons encoding the following amino acid combination (aa1'), (aa3'), (aa6'), (aa9'), (aa10'), or (aa12') and is more preferably the combination of codons encoding the following amino acid combination (aa1') or (aa9'), for example, as the novel fluorescent protein encoded by the novel fluorescent protein gene shows stronger fluorescence even with excitation light having a relatively low wavelength. Furthermore, in the novel fluorescent protein gene of the present invention, the combination of the $N_{154}N_{155}N_{156}$ codon, the $N_{397}N_{398}N_{399}$ codon, and the $N_{460}N_{461}N_{462}$ codon is preferably the combination of codons encoding the following amino acid combination (aa2') as the novel fluorescent protein encoded by the novel fluorescent protein gene shows stronger fluorescence under excitation with excitation light at the same intensity, for example. The novel gene of the present invention excludes genes in which the combination of the $N_{154}N_{155}N_{156}$ codon, the $N_{397}N_{398}N_{399}$ codon, and the $N_{460}N_{461}N_{462}$ codon is the combination of the codons encoding H, S, and R and the combination of the codons encoding D, S, and R, for example.

TABLE 2

|  | $N_{154}N_{155}N_{156}$ | $N_{397}N_{398}N_{399}$ | $N_{460}N_{461}N_{462}$ |
| --- | --- | --- | --- |
| (aa1') | T | S | Y |
| (aa2') | H | T | K |
| (aa3') | C | L | L |
| (aa4') | C | S | H |
| (aa5') | T | S | H |
| (aa6') | M | L | V |
| (aa7') | F | S | Q |
| (aa8') | K | T | A |
| (aa9') | C | Q | L |
| (aa10') | T | T | I |
| (aa11') | K | S | Q |
| (aa12') | M | L | A |

In the novel fluorescent protein gene of the present invention, the combination of amino acids of the $N_{154}N_{155}N_{156}$ codon, the $N_{397}N_{398}N_{399}$ codon, and the $N_{460}N_{461}N_{462}$ codon is, for example, one of the following combinations (n1) to (n18). In the novel fluorescent protein gene of the present invention, for example, the combination of amino acids of the $N_{154}N_{155}N_{156}$ codon, the $N_{397}N_{398}N_{399}$ codon, and the $N_{460}N_{461}N_{462}$ codon is preferably one of the following combinations (n1), (n2), (n3), (n6), (n10), (n11), (n14), (n15), (n16), and (n18) as the novel fluorescent protein encoded by the novel fluorescent protein gene shows stronger fluorescence even with excitation light having a relatively low wavelength and is more preferably one of the following combinations (n1), (n2), (n3), (n14), and (n15) as the novel fluorescent protein encoded by the novel fluorescent protein gene shows further stronger fluorescence even with excitation light having a relatively low wavelength. In the novel fluorescent protein gene of the present invention, the combination of amino acids of the $N_{154}N_{155}N_{156}$ codon, the $N_{397}N_{398}N_{399}$ codon, and the $N_{460}N_{461}N_{462}$ codon is preferably the following combination (n4) or (n5) as the novel fluorescent protein encoded by the novel fluorescent protein gene shows stronger fluorescence under excitation with excitation light at the same intensity, for example.

TABLE 3

|  | $N_{154}N_{155}N_{156}$ | $N_{397}N_{398}N_{399}$ | $N_{460}N_{461}N_{462}$ |
| --- | --- | --- | --- |
| (n1) | ACA | TCT | TAC |
| (n2) | ACC | AGC | TAT |
| (n3) | ACT | AGT | TAC |
| (n4) | CAC | ACT | AAG |
| (n5) | CAC | ACA | AAG |
| (n6) | TGC | TTA | CTT |
| (n7) | TGC | AGC | CAT |
| (n8) | TGT | AGC | CAC |
| (n9) | ACG | AGC | CAC |
| (n10) | ATG | CTG | GTA |
| (n11) | ATG | CTC | GTG |
| (n12) | AAA | AGC | CAA |
| (n13) | AAA | ACT | GCT |
| (n14) | TGT | CAA | CTT |
| (n15) | TGC | CAA | TTG |
| (n16) | ACT | ACA | ATT |
| (n17) | AAA | AGC | CAA |
| (n18) | ATG | CTC | GCC |

In the novel fluorescent protein gene of the present invention, the $N_{613}N_{614}N_{615}$ codon is preferably substituted with a codon encoding I as the novel fluorescent protein encoded by the novel fluorescent protein gene shows stronger fluorescence even with excitation light having a relatively low wavelength, for example. In this case, the codon encoding I is preferably ATA. Also in the novel fluorescent protein gene of the present invention, the $N_{592}N_{593}N_{594}$ codon is preferably substituted with a codon encoding L or H as the novel fluorescent protein encoded by the novel fluorescent protein gene shows stronger fluorescence even with excitation light having a relatively low wavelength, for example. In this case, the codon encoding L is preferably CTC and the codon encoding H is preferably CAC. In the novel fluorescent protein gene of the present invention, the $N_{592}N_{593}N_{594}$ codon and the $N_{613}N_{614}N_{615}$ codon are preferably substituted with the combination of codons encoding L and I or the combination of codons encoding H and I as the novel fluorescent protein encoded by the novel fluorescent protein gene shows further stronger fluorescence even with excitation light having a relatively low wavelength, for example. In this case, the codons encoding L and I are preferably CTC and ATA, respectively, and the codons encoding H and I are CAC and ATA, respectively.

The polynucleotide (f1) can be, for example, a polynucleotide consisting of at least one base sequence selected from the group consisting of SEQ ID NOs: 15 to 32, 68 to 100, and 101. In the case where the polynucleotide (f1) is a polynucleotide consisting of at least one base sequence selected from the group consisting of SEQ ID NOs: 15 to 32, and 68 to 101, the polynucleotide (f1) is also referred to as one of polynucleotides (f1-1) to (f1-52), the polynucleotide (f2) is also referred to as one of polynucleotides (f2-1) to (f2-52), the polynucleotides (f3) is also referred to as one of polynucleotides (f3-1) to (f3-52), the polynucleotide (f4) is also referred to as one of polynucleotides (f4-1) to (f4-52), the polynucleotide (f5) is also referred to as one of polynucleotides (f5-1) to (f5-52), the polynucleotide (f6) is also referred to as one of polynucleotides (f6-1) to (f6-52), and the polynucleotide (f7) is also referred to as one of polynucleotides (f7-1) to (f7-52).

The polynucleotide (b1) can be a polynucleotide consisting of at least one base sequence selected from the group consisting of SEQ ID NOs: 15 to 17, 20, 24, 25, 28 to 30, 32, and 68 to 101, for example. Regarding the polynucleotide (b1) consisting of at least one of the above-described base sequences, reference can be made to the description as to the polynucleotide (f1) consisting of at least one of the above-described base sequences.

The base sequences of SEQ ID NOs: 15 to 32 and 68 to 101 of the polynucleotide (f1) are as follows. The base sequences of SEQ ID NOs: 15 to 32 correspond to the cases where the combinations of amino acids of the $N_{154}N_{155}N_{156}$ codon, the $N_{397}N_{398}N_{399}$ codon, and the $N_{460}N_{461}N_{462}$ codon are the combinations (n1) to (n18), respectively, in the base sequence of SEQ ID NO: 14. Each of the polynucleotides (f1-1) to (f1-3) is a polynucleotide encoding the amino acid sequence of the protein (F1-1), each of the polynucleotides (f1-4) and (f1-5) is a polynucleotide encoding the amino acid sequence of the protein (F1-2), the polynucleotide (f1-6) is a polynucleotide encoding the amino acid sequence of the protein (F1-3), each of the polynucleotides (f1-7) and (f1-8) is a polynucleotide encoding the amino acid sequence of the protein (F1-4), the polynucleotide (f1-9) is a polynucleotide encoding the amino acid sequence of the protein (F1-5), each of the polynucleotides (f1-10) and (f1-11) is a polynucleotide encoding the amino acid sequence of the protein (F1-6), the polynucleotide (f1-12) is a polynucleotide encoding the amino acid sequence of the protein (F1-7), the polynucleotide (f1-13) is a polynucleotide encoding the amino acid sequence of the protein (F1-8), each of the polynucleotides (f1-14) and (f1-15) is a polynucleotide encoding the amino acid sequence of the protein (F1-9), the polynucleotide (f1-16) is a polynucleotide encoding the amino acid sequence of the protein (F1-10), the polynucleotide (f1-17) is a polynucleotide encoding the amino acid sequence of the protein (F1-11), and the polynucleotide (f1-18) is a polynucleotide encoding the amino acid sequence of the protein (F1-12). The base sequences of SEQ ID NOs: 68 to 82 correspond to the case where the combination of amino acids of the $N_{154}N_{155}N_{156}$ codon, the $N_{397}N_{398}N_{399}$ codon, and the $N_{460}N_{461}N_{462}$ codon corresponds to the combination (n3) in the base sequence of SEQ ID NO: 14. The polynucleotides (f1-19) to (f1-33) are polynucleotides encoding the amino acid sequences of the proteins (F1-13) to (F1-27), respectively. The base sequences of SEQ ID NOs: 83 to 101 correspond to the case where the combination of amino acids of the $N_{154}N_{155}N_{156}$ codon, the $N_{397}N_{398}N_{399}$ codon, and the $N_{460}N_{461}N_{462}$ codon corresponds to the combination (n15) in the base sequence of SEQ ID NO: 14. The polynucleotides (f1-34) to (f1-52) are polynucleotides encoding the amino acid sequences of the proteins (F1-28) to (F1-46), respectively.

```
Polynucleotide (f1-1)
                                            (SEQ ID NO: 15)
5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACATGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGT

CTTGTCCCACGGTGGACCTGATGTTGCCGATGTCCGGGAACATCATCGCC

AGCTCCTACGCTTACGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC
```

```
AAGGAGAACCTTGCCATGGTGGAGTACCAGCAGGTTTTCAACAGCGCCCC

AAGAGACATGTAG-3'

Polynucleotide (f1-2)
                                            (SEQ ID NO: 16)
5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACCTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GGTGTCCCACGGTGGACCTGATGTTGCCGATGTCCGGGAACATCATCGCC

AGCTCCTACGCTTATGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC

AAGGAGAACCTTGCCATGGTGGAGTACCAGCAGGTTTTCAACAGCGCCCC

AAGAGACATGTAG-3'

Polynucleotide (f1-3)
                                            (SEQ ID NO: 17)
5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACTTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GTTGTCCCACGGTGGACCTGATGTTGCCGATGTCCGGGAACATCATCGCC

AGCTCCTACGCTTACGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC

AAGGAGAACCTTGCCATGGTGGAGTACCAGCAGGTTTTCAACAGCGCCCC

AAGAGACATGTAG-3'

Polynucleotide (f1-4)
                                            (SEQ ID NO: 18)
5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG
```

AGATTGAGATGAAGACTAAAGATAAACCACTGGCATTCTCTCCCTTCCTG
CTGTCC[CAC]TGCATGGGTTACGGGTTCTACCACTTCGCCAGCTTCCCAAA

GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG[A]
[CT]TGTCCCACGGTGGACCTGATGTTGCCGATGTCCGGGAACATCATCGCC
AGCTCCTACGCT[AAG]GCCTTCCAACTGAAGGACGGCTCTTTCTACACGGC

AGAAGTCAAGAACAACATAGACTTCAAGAATCCAATCCACGAGTCCTTCT
CGAAGTCGGGGCCCATGTTCACCCACAGACGTGTCGAGGAGACT<u>CAC</u>ACC
AAGGAGAACCTTGCC<u>AT</u>GGTGGAGTACCAGCAGGTTTTCAACAGCGCCCC
AAGAGACATGTAG-3'

Polynucleotide (f1-5)
(SEQ ID NO: 19)
5'-ATGACAACCTTCAAAATCGAGTCCCGGATCCATGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC[CAC]TGCATGGGTTACGGGTTCTACCACTTCGCCAGCTTCCCAAA GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG[A]
[CA]TGTCCCACGGTGGACCTGATGTTGCCGATGTCCGGGAACATCATCGCC
AGCTCCTACGCT[AAG]GCCTTCCAACTGAAGGACGGCTCTTTCTACACGGC AGAAGTCAAGAACAACATAGACTTCAAGAATCCAATCCACGAGTCCTTCT
CGAAGTCGGGGCCCATGTTCACCCACAGACGTGTCGAGGAGACT<u>CAC</u>ACC
AAGGAGAACCTTGCC<u>AT</u>GGTGGAGTACCAGCAGGTTTTCAACAGCGCCCC
AAGAGACATGTAG-3'

Polynucleotide (f1-6)
(SEQ ID NO: 20)
5'-ATGACAACCTTCAAAATCGAGTCCCGGATCCATGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC[TGC]TGCATGGGTTACGGGTTCTACCACTTCGCCAGCTTCCCAAA GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG[T]
[TA]TGTCCCACGGTGGACCTGATGTTGCCGATGTCCGGGAACATCATCGCC
AGCTCCTACGCT[CTT]GCCTTCCAACTGAAGGACGGCTCTTTCTACACGGC AGAAGTCAAGAACAACATAGACTTCAAGAATCCAATCCACGAGTCCTTCT
CGAAGTCGGGGCCCATGTTCACCCACAGACGTGTCGAGGAGACT<u>CAC</u>ACC
AAGGAGAACCTTGCC<u>AT</u>GGTGGAGTACCAGCAGGTTTTCAACAGCGCCCC
AAGAGACATGTAG-3'

Polynucleotide (f1-7)
(SEQ ID NO: 21)
5'-ATGACAACCTTCAAAATCGAGTCCCGGATCCATGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC[TGC]TGCATGGGTTACGGGTTCTACCACTTCGCCAGCTTCCCAAA GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG[A]
[GC]TGTCCCACGGTGGACCTGATGTTGCCGATGTCCGGGAACATCATCGCC
AGCTCCTACGCT[CAT]GCCTTCCAACTGAAGGACGGCTCTTTCTACACGGC AGAAGTCAAGAACAACATAGACTTCAAGAATCCAATCCACGAGTCCTTCT
CGAAGTCGGGGCCCATGTTCACCCACAGACGTGTCGAGGAGACT<u>CAC</u>ACC
AAGGAGAACCTTGCC<u>AT</u>GGTGGAGTACCAGCAGGTTTTCAACAGCGCCCC
AAGAGACATGTAG-3'

Polynucleotide (f1-8)
(SEQ ID NO: 22)
5'-ATGACAACCTTCAAAATCGAGTCCCGGATCCATGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC[TGT]TGCATGGGTTACGGGTTCTACCACTTCGCCAGCTTCCCAAA GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG[A]
[GC]TGTCCCACGGTGGACCTGATGTTGCCGATGTCCGGGAACATCATCGCC
AGCTCCTACGCT[CAC]GCCTTCCAACTGAAGGACGGCTCTTTCTACACGGC AGAAGTCAAGAACAACATAGACTTCAAGAATCCAATCCACGAGTCCTTCT
CGAAGTCGGGGCCCATGTTCACCCACAGACGTGTCGAGGAGACT<u>CAC</u>ACC

AAGGAGAACCTTGCCATGGTGGAGTACCAGCAGGTTTTCAACAGCGCCCC

AAGAGACATGTAG-3'

Polynucleotide (f1-9)

(SEQ ID NO: 23)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACGTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GCTGTCCCACGGTGGACCTGATGTTGCCGATGTCCGGGAACATCATCGCC

AGCTCCTACGCTCACGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC

AAGGAGAACCTTGCCATGGTGGAGTACCAGCAGGTTTTCAACAGCGCCCC

AAGAGACATGTAG-3'

Polynucleotide (f1-10)

(SEQ ID NO: 24)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCATGTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGC

TGTGTCCCACGGTGGACCTGATGTTGCCGATGTCCGGGAACATCATCGCC

AGCTCCTACGCTGTAGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC

AAGGAGAACCTTGCCATGGTGGAGTACCAGCAGGTTTTCAACAGCGCCCC

AAGAGACATGTAG-3'

Polynucleotide (f1-11)

(SEQ ID NO: 25)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCATGTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGC

TGTGTCCCACGGTGGACCTGATGTTGCCGATGTCCGGGAACATCATCGCC

AGCTCCTACGCTGTGGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC

AAGGAGAACCTTGCCATGGTGGAGTACCAGCAGGTTTTCAACAGCGCCCC

AAGAGACATGTAG-3'

Polynucleotide (f1-12)

(SEQ ID NO: 26)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCAAATGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GCTGTCCCACGGTGGACCTGATGTTGCCGATGTCCGGGAACATCATCGCC

AGCTCCTACGCTCAAGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC

AAGGAGAACCTTGCCATGGTGGAGTACCAGCAGGTTTTCAACAGCGCCCC

AAGAGACATGTAG-3'

Polynucleotide (f1-13)

(SEQ ID NO: 27)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCAAATGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

CTTGTCCCACGGTGGACCTGATGTTGCCGATGTCCGGGAACATCATCGCC

AGCTCCTACGCTGCTGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CAC</u>ACC

AAGGAGAACCTTGCC<u>ATG</u>GTGGAGTACCAGCAGGTTTTCAACAGCGCCCC

AAGAGACATGTAG-3'

Polynucleotide (f1-14)

(SEQ ID NO: 28)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCTGTTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGC

AATGTCCCACGGTGGACCTGATGTTGCCGATGTCCGGGAACATCATCGCC

AGCTCCTACGCTCTTGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CAC</u>ACC

AAGGAGAACCTTGCC<u>ATG</u>GTGGAGTACCAGCAGGTTTTCAACAGCGCCCC

AAGAGACATGTAG-3'

Polynucleotide (f1-15)

(SEQ ID NO: 29)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCTGCTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGC

AATGTCCCACGGTGGACCTGATGTTGCCGATGTCCGGGAACATCATCGCC

AGCTCCTACGCTTTCGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CAC</u>ACC

AAGGAGAACCTTGCC<u>ATG</u>GTGGAGTACCAGCAGGTTTTCAACAGCGCCCC

AAGAGACATGTAG-3'

Polynucleotide (f1-16)

(SEQ ID NO: 30)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACTTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

CATGTCCCACGGTGGACCTGATGTTGCCGATGTCCGGGAACATCATCGCC

AGCTCCTACGCTATTGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CAC</u>ACC

AAGGAGAACCTTGCC<u>ATG</u>GTGGAGTACCAGCAGGTTTTCAACAGCGCCCC

AAGAGACATGTAG-3'

Polynucleotide (f1-17)

(SEQ ID NO: 31)

5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCAAATGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GCTGTCCCACGGTGGACCTGATGTTGCCGATGTCCGGGAACATCATCGCC

AGCTCCTACGCTCAAGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CAC</u>ACC

AAGGAGAACCTTGCC<u>ATG</u>GTGGAGTACCAGCAGGTTTTCAACAGCGCCCC

AAGAGACATGTAG-3'

Polynucleotide (f1-18)
(SEQ ID NO: 32)
5'-ATGACAACCTTCAAAATCGAGTCCCGGATCCATGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC<u>ATG</u>TGCATGGGTTACGGGTTCTACCACTTCGCCAGCTTCCCAAA GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG<u>C</u>
<u>TC</u>TGTCCCACGGTGGACCTGATGTTGCCGATGTCCGGGAACATCATCGCC
AGCTCCTACGCT<u>GCC</u>GCCTTCCAACTGAAGGACGGCTCTTTCTACACGGC AGAAGTCAAGAACAACATAGACTTCAAGAATCCAATCCACGAGTCCTTCT
CGAAGTCGGGGCCCATGTTCACCCACAGACGTGTCGAGGAGACT<u>CAC</u>ACC
AAGGAGAACCTTGCC<u>ATG</u>GTGGAGTACCAGCAGGTTTTCAACAGCGCCCC
AAGAGACATGTAG-3'

Polynucleotide (f1-19)
(SEQ ID NO: 68)
5'-ATGACAACCTTCAAAATCGAGTCCCGGATCCATGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC<u>ACT</u>TGCATGGGTTACGGGTTCTACCACTTCGCCAGCTTCCCAAA GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG<u>A</u>
<u>GT</u>TGTCCCACGGTGGACCTGATGTTGCCGATGTCCGGGAACATCATCGCC
AGCTCCTACGCT<u>TAC</u>GCCTTCCAACTGAAGGACGGCTCTTTCTACACGGC AGAAGTCAAGAACAACATAGACTTCAAGAATCCAATCCACGAGTCCTTCT
CGAAGTCGGGGCCCATGTTCACCCACAGACGTGTCGAGGAGACT<u>CAC</u>ACC
AAGGAGAACCTTGCC<u>ATA</u>GTGGAGTACCAGCAGGTTTTCAACAGCGCCCC
AAGAGACATGTAG-3'

Polynucleotide (f1-20)
(SEQ ID NO: 69)
5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC<u>ACT</u>TGCATGGGTTACGGGTTCTACCACTTCGCCAGCTTCCCAAA GGGGACTAAGAACATCTATCTTCATGCTGCAACGAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG<u>A</u>
<u>GT</u>TGTCCCACGGTGGACCTGATGTTGCCGATGTCCGGGAACATCATCGCC
AGCTCCTACGCT<u>TAC</u>GCCTTCCAACTGAAGGACGGCTCTTTCTACACGGC AGAAGTCAAGAACAACATAGACTTCAAGAATCCAATCCACGAGTCCTTCT
CGAAGTCGGGGCCCATGTTCACCCACAGACGTGTCGAGGAGACT<u>CTC</u>ACC
AAGGAGAACCTTGCC<u>ATA</u>GTGGAGTACCAGCAGGTTTTCAACAGCGCCCC
AAGAGACATGTAG-3'

Polynucleotide (f1-21)
(SEQ ID NO: 70)
5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC<u>ACT</u>TGCATGGGTTACGGGTTCTACCACTTCGCCAGCTTCCCAAA GGGGACTAAGAACATCTATCTTCATGCTGCAACGAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG<u>A</u>
<u>GT</u>TGTCCCACGGTGGACCTGATGTTGCCGATGTCCGGGAACATCATCGCC
AGCTCCTACGCT<u>TAC</u>GCCTTCCAACTGAAGGACGGCTCTTTCTACACGGC AGAAGTCAAGAACAACATAGACTTCAAGAATCCAATCCACGAGTCCTTCT
TGAAGTCGGGGCCCATGTTCACCCACAGACGTGTCGAGGAGACT<u>CTC</u>ACC
AAGGAGAACCTTGCC<u>ATA</u>GTGGAGTACCAGCAGGTTTTCAACAGCGCCCC
AAGAGACATGTAG-3'

Polynucleotide (f1-22)
(SEQ ID NO: 71)
5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCC<u>ACT</u>TGCATGGGTTACGGGTTCTACCACTTCGCCAGCTTCCCAAA GGGGACTAAGAACATCTATCTTCATGCTGCAACGAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAG<u>A</u>
<u>GT</u>TGTCCCACGGTGGACCTGATGCCCGGGAACATCATCGCC
AGCTCCTACGCT<u>TAC</u>GCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCTCACC

AAGGAGAACCTTGCCATAGTGGAGTACCAGCAGGTTTTCAACAGCGCCCC

AAGAGACATGTAG-3'

Polynucleotide (f1-23)

(SEQ ID NO: 72)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACTTGCATGGGTTACGGGTTCTACCACTTCGCCAGCTTCCCAAA

GGGGATTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GTTGTCCCACGGTGGACCTGATGTTGCCAATGTCCGGGAACATCATCGCC

AGCTCCTACGCTTACGCCTTCCAACTGAAGGACGGCTCTTTCTACACGGC

AGAAGTCAAGAACAACATAGACTTCAAGAATCCAATCCACGAGTCCTTCT

CGAAGTCAGGGCCCATGTTCACCCACAGACGTGTCGAGGAGACTCTCACC

AAGGAGAACCTTGCCATAGTGGAGTACCAGCAGGTTTTCAACAGCGCCCC

AAGAGACATGTAG-3'

Polynucleotide (f1-24)

(SEQ ID NO: 73)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGACCACTTGCATGGGTTACGGGTTCTACCACTTCGCCAGCTTCCCAAA

GGGGACTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GTTGTCCCACGGTGGACCTGATGTTGCCGATGTCCGGGAACATCATCGCC

AGCTCCTACGCTTACGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCTCACC

AAGGAGAACCTTGCCATAGTGGAGTACCAGCAGGTTTTCAACAGCGCCCC

AAGAGACATGTAG-3'

Polynucleotide (f1-25)

(SEQ ID NO: 74)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACTTGCATGGGTTACGGGTTCTACCACTTCGCCAGCTTCCCAAA

GGGGACTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGA

GTTGTCCCACGGTGGACCTGATGTTGCCGATGTCCGGGAACATCATCGTC

AGCTCCTACGCTTACGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCTCACC

AAGGAGAACCTTGCCATAGTGGAGTACCAGCAGGTTTTCAACAGCGCCCC

AAGAGACATGTAG-3'

Polynucleotide (f1-26)

(SEQ ID NO: 75)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCACTTGCATGGGTTACGGGTTCTACCACTTCGCCAGCTTCCCAAA

GGGGACTAAGAACATCTATCTTCATGCTGCAACGAACGGAGGTTACACCA

ACACCCGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCGAGTCAGAGTCCGATCTTCAAGGACACGATCGTGAAGA

GTTGTCCCACGGTGGACCTGATGTTGCCGATGACCGGGAACATCATCACC

AGCTCCTACGCTTACGCCTTCCAACTGAAGGACGGCTCTTTCTACACGGC

GGAAGTCAAGAACAACATAGACTTCAAGAATCCAATCCACGAGTCCTTCT

CGAAGTCGGGGCCCATGTTCACCCACAGACGTGTCGAGGAGACTCTCACC

AAGGAGAACCTTGCCATAGTGGAGTACCAGCAGGTTTTCAACAGCGCCCC

AAGAGACATGTAG-3'

Polynucleotide (f1-27)

(SEQ ID NO: 76)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAGGACTAAAGATAAACCACTGGCATTCTCTCCCTTCCTG

CTGTCCACTTGCATGGGTTACGGGTTCTACCACTTCGCCAGCTTCCCAAA

GGGGACTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG[A]

[GT]TGTCCCACGGTGGACCTGATGTTGCCGATGTCCGGGAACATCATCGTC

AGCTCCTACGCT[TAC]GCCTTCCAACTGAAGGACGGCACTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CTC</u>ACC

AAGGAGAACCTTGCC<u>ATA</u>GTGGAGTACCAGCAGGTTTTCAACAGCGCCCC

AAGAGACATGTAG-3'

Polynucleotide (f1-28)

(SEQ ID NO: 77)

5'-ATGACAACCTTCAAAATCGAGTCCCGGATCCACGGCAACCTCAACGG

GGAGGAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC[ACT]TGCATGGGTTACGGGTTCTACCACTTCGCCAGCTTCCCAAA

GGGGACTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG[A]

[GT]TGTCCCACGGTGGACCTGATGTTGCCGATGCCCGGGAACATCATCGCC

AGCTCCTACGCT[TAC]GCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CTC</u>ACC

AAGGAGAACCTTGCC<u>ATA</u>GTGGAGTACCAGCAGGTTTTCAACAGCGCCCC

AAGAGACATGTAG-3'

Polynucleotide (f1-29)

(SEQ ID NO: 78)

5'-ATGACAACCTTCAAAATCGAGTCCCGGATCCACGGCAACCTCAACGG

GGAGGAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC[ACT]TGCATGGGTTACGGGTTCTACCACTTCGCCAGCTTCCCAAA

GGGGATTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACAATCGTGAAG[A]

[GT]TGTCCCACGGTGGACCTGATGTTGCCGATGTCCGGGAACATCATCGCC

AGCTCCTACGCT[TAC]GCCTTCCAACTGAAGGACGGCTCTTTCTACACGGC

AGAAGTCAAGAACAACATAGACTTCAGGAATCCAATCCACGAGTCCTTCT

CGAAGTCGGGGCCCATGTTCACCCACAGACGTGTCGAGGAGACT<u>CTC</u>ACC

AAGGAGAACCTTGCC<u>ATA</u>GTGGAGTACCAGCAGGTTTTCAACAGCGCCCC

AAGAGACATGTAG-3'

Polynucleotide (f1-30)

(SEQ ID NO: 79)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC[ACT]TGCATGGGTTACGGGTTCTACCACTTCGCCAGCTTCCCAAA

GGGGACTAAGAACATCTATCTTCATGCTGCAACGAACGGAGGTTACACCA

ACACCAGGAAGGAGATCTATGAAGACGGCGGCGTCTTGGAGGTCAACTTC

CGTTACACTTACGAGTTCGACAAGATCATCGGTGACGTCGAGTGCATTGG

ACATGGATTCCCAAGTCAGAGTCCGATCTTCAAGGACACGATCGTGAAG[A]

[GT]TGTCCCACGGTGGACCTGATGTTGCCGATGTCCGGGAACATCATCGCC

AGCTCCTACGCT[TAC]GCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>CTC</u>ACC

AAGGAGAACCTTGCC<u>ATA</u>GTGGAGTACCAGCAGGTTTTCAACAGCGCCCC

AAGGGACATGTAG-3'

Polynucleotide (f1-31)

(SEQ ID NO: 80)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC[ACT]TGCATGGGTTACGGGTTCTACCACTTCGCCAGCTTCCCAAA

GGGGACTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG[A]

[GT]TGTCCCACGGTGGACCTGATGTTGCCGATGTCCGGGAACATCATCGCC

AGCTCCTACGCT[TAC]GCCTTCCAACTGAAGGACGGCTCTTTCTACACGGC

AGAAGTCAAGAACAACATAGACTTCAAGAATCCAATCCACGAGTCCTTCT

TGAAGTCGGGGCCCATGTTCACCCACAGACGTGTCGAGGAGACT<u>CTC</u>ACC

AAGGAGAACCTTGCC<u>ATA</u>GTGGAGTACCAGCAGGTTTTCAACAGCGCCCC

AAGAGACATGTAG-3'

Polynucleotide (f1-32)

(SEQ ID NO: 81)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATAGAGATGAAGACTAAAGATAAACCACTGGCATTCTCTCCCTTCCTG

TTGTCC<span style="border:1px solid">ACT</span>AGCATGGGTTACGGGTTCTACCACTTCGCCAGCTTCCCAAA

GGGGACTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGATGTCGAGTGCATTGG

ACATGGATTCCCAAGTCAGAGTCCGATCTTCAAGGACACGATCGTGAAG<span style="border:1px solid">A</span>

<span style="border:1px solid">GT</span>TGTCCCACGGTGGACCTGATGTTGCCGATGTCCGGGAACATCATCGCC AGCTCCTACGCT<span style="border:1px solid">TAC</span>GCCTTCCAACTGAAGGACGGCTCTTTCTACACGGC

AGATGTCAAGAACAACATAGACTTCAAGAATCCAATCCACGAGTCCTTCT

CGAAGTCGGGGCCCATGTTCACCCACAGACGTGTCGAGGAGACT<u>CTC</u>ACC

AAGGAGAACCTTGCC<u>ATA</u>GTGGAGTACCAGCAGGTTTTCAACAGCGCCCC

AAGAGACATGTAG-3'

Polynucleotide (f1-33)

(SEQ ID NO: 82)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGACC<span style="border:1px solid">ACT</span>TGCATGGGTTACGGGTTCTACCACTTCGCCAGCTTCCCAAA

GGGGATTAAGAACATCTATCTTCATGCTGCAACGAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG<span style="border:1px solid">A</span>

<span style="border:1px solid">GT</span>TGTCCCACGGTGGACCTGATGTTGCCAATGTCCGGGAACATCATCGCC AGCTCCTACGCT<span style="border:1px solid">TAC</span>GCCTTCCAACTGAAGGACGGCTCTTTCTACACGGC

AGAAGTCAAGAACAACATAGACTTCAAGAATCCAATCCACGAGTCCTTCT

CGAAGTCAGGGCCCATGTTCACCCACAGACGTGTCGAGGAGACT<u>CTC</u>ACC

AAGGAGAACCTTGCC<u>ATA</u>GTGGAGTACCAGCAGGTTTTCAACAGCGCCCC

AAGAGACATGTAG-3'

Polynucleotide (f1-34)

(SEQ ID NO: 83)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC<span style="border:1px solid">TGC</span>TGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG<span style="border:1px solid">C</span>

<span style="border:1px solid">AA</span>TGTCCCACGGTGGACCTGATGTTGCCGATGTCCGGGAACATCATCGCC AGCTCCTACGCT<span style="border:1px solid">TTG</span>GCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>TAC</u>ACC

AAGGAGAACCTTGCC<u>ATG</u>GTGGAGTACCAGCAGGTTTTCAACAGCGCCCC

AAGAGACATGTAG-3'

Polynucleotide (f1-35)

(SEQ ID NO: 84)

5'-ATGACAACCTTCAAAATCGAGTCCCGGATCCGTGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC<span style="border:1px solid">TGC</span>TGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGCTCAACAAGATCATCGGTGACGTCGAGTGCATTGG

ACATGGATTCCCAAGTCAGAGTCCGATCTTCAAGGACACGATCGTGAAG<span style="border:1px solid">C</span>

<span style="border:1px solid">AA</span>TGTCCCACGGTGGACCTGATGTTGCCGATGTCCGGGAACATCATCGCC AGCTCCTACGCT<span style="border:1px solid">TTG</span>GCCTTCCGACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>TAC</u>ACC

AAGGAGAACCTTGCC<u>ATG</u>GTGGAGTACCAGCAGGTTTTCAACAGCGCCCC

AAGAGACATGTAG-3'

Polynucleotide (f1-36)

(SEQ ID NO: 85)

5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC<span style="border:1px solid">TGC</span>TGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGC

AATGTCCCACGGTGGACCTGATGTTGCCGATGTCCGGGAACATCATCGCC

AGCTCCTACGCTTTGGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCTACAGACGTGTCGAGGAGACTTACACC

AAGGAGAACCTTGCCATGGTGGAGTACCAGCAGGTTTTCAACAGCGCCCC

AAGAGACATGTAG-3'

Polynucleotide (f1-37)

(SEQ ID NO: 86)
5'-ATGACAACCTTCAAAATCGAGTCCCGGATCCATGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCTGCTGCATGGGTTACGGGTTCTACCACTTCGCCAGCTTCCCAAA

GGGGACTAAGAACATCTATCTTCATGCTGCAACAAACGGAGGTTACACTA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

GCATGGATTCCCAAGTCAGAGTCCGATCTTCAAGGACACGATCGTGAAGC

AATGTCCCACGGTGGACCTGATGTTGCCGGTGTCCGGGAACATCATCGCC

AGCTCCTACGCTTTGGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTTACACC

AAGGAGAACCTTGCCATGGTGGAGTACCAGCAGGTTTTCAACAGCGCCCC

AAGAGACATGTAG-3'

Polynucleotide (f1-38)

(SEQ ID NO: 87)
5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCTGCTGCATGGGTTACGGGTTCTACCACTTCGCCAGCTTCCCAAA

GGGGACTGAGAACATCTATCTTCATGCTGCAACACACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

GCATGGATTCCCAAGTCAGAGTCCGATCTTCAAGGACACGATCGTGAGGC

AATGTCCCACGGTGGACCTGATGTTGCCGGTGTCCGGGAACATCATCGCC

AGCTCCTACGCTTTGGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTTACACC

AAGGAGAACCTTGCCATGGTGGAGTACCAGCAGGTCTTCAACAGCGCCCC

AAGAGACATGTAG-3'

Polynucleotide (f1-39)

(SEQ ID NO: 88)
5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCTGCTGCATGGGTTACGGGTTCTACCACTTCGCCAGCTTCCCAAA

GGGGCTAAGAACATCTATCTCCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGC

AATGTCCCACGGTGGACCTGATGTTGCCGATGTCCGGGAACATCATCGCC

AGCTCCTACGCTTTGGCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTCACACC

AAGGAGAACCTTGCCATAGTGGAGTACCAGCAGGTTTTCAACAGCGCCCC

AAGAGACATGTAG-3'

Polynucleotide (f1-40)

(SEQ ID NO: 89)
5'-ATGACAACCTTCAAAATCGAGTCCCGGATCCACGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCCTGCTGCATGGGTTACGGGTTCTACCACTTCGCCAGCTTCCCAAA

GGGGACTAAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAGC

AATGTCCCACGGTGGACCTGATGTTGCCGATGTCCGGGAACATCATCGCC

AGCTCCTACGCTTTGGCCTTCCAACTGAGGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACTTACACC

AAGGAGAACCTTGCCATGGTGGAGTACCAGCAGGTTTTCAACAGCGCCCC

AAGAGACATGTAG-3'

Polynucleotide (f1-41)

(SEQ ID NO: 90)

5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATGTCCCACGGTGGACCTGATGTTGCCGGTGTCCAGGAACATCATCGCC
AGCTCCTACGCTTTGGCCTTCCAACTGAAGGACGGCTCTTTCTACACGGC
AGAAGTCAAGAACAACATAGACTTCAAGAATCCAATCCACGAGTCCTTCT
CGAAGTCGGGGCCCATGTTCACCCACAGACGTGTCGAGGAGACTTACACC
AAGGAGAACCTTGCCATGGTGGAGTACCAGCAGGTTTTCAACAGCGCCCC
AAGAGACATGTAG-3'

Polynucleotide (f1-42)

(SEQ ID NO: 91)

5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATGTCCCACGGTGGACCTGATGTTGCCGATGTCCGGGAACATCATCGCC
AGCTCCTACGCTTTGGCCTTCCAACTGAAGGACGGCTCTTTCTACACGGC
AGAAGTCAAGAACAACATAGACTTCAAGAATCCAATCCACGAGTCCTTCT
CGAAGTCGGGGCCCATGTTCACCCACAGACGTGTCGAGGAGACTTACACC
AAGGAGAACCTTGCCATGGTGGAGTACCAGCAGGTTTTCAACAGCGCCCC
AAGAGACGTGTAG-3'

Polynucleotide (f1-43)

(SEQ ID NO: 92)

5'-ATGACAACCTTCAAAATCGAGTCCCGGATCCATGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTGAGAACATCTATCTTCATGCTGCAACACACGGAGGTTACACTA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATGTCCCACGGTGGACCTGATGTTGCCGATGTCCGGGAACATCATCGCC
AGCTCCTACGCTTTGGCCTTCCAACTGAAGGACGGCTCTTTCTACACGGC
AGAAGTCAAGAACAACATAGACTTCAAGAATCCAATCCACGAGTCCTTCT
CGAAGTCGGGGCCCATGTTCACCCACAGACGTGTCGAGGAGACTTACACC
AAGGAGAACCTTGCCATGGTGGAGTACCAGCAGGTTTTCAACAGCGCCCC
AAGAGACATGTAG-3'

Polynucleotide (f1-44)

(SEQ ID NO: 93)

5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTAAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATATCCCACGGTGGACCTGATGTTGCCGATGTCCGGGAACATCATCGCC
AGCTCCTACGCTTTGGCCTTCCAACTGAAGGACGGCTCTTTCTACACGGC
AGAAGTCAAGAACAACATAGACTTCAAGAATCCAATCCACGAGTCCTTCT
CGAAGTCGGGGCCCATGTTCACCCACAGACGTGTCGAGGAGACTCACACC
AAGGAGAACCTTGCCATAGTGGAGTACCAGCAGGTTTTCAACAGCGCCCC
AAGAGACATGTAG-3'

Polynucleotide (f1-45)

(SEQ ID NO: 94)

5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTGAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG

ACATGGATTCCCAAGTCAGAGTCCGATCTTCAAGGACACGATCGTGAAGC
AATGTCCCACGGTGGACCTGATGTTGCCGATGTCCGGGAACATCATCGCC
AGCTCCTACGCTTTGGCCTTCCAACTGAAGGACGGCTCTTTCTACACGGC
AGAAGTCAAGAACAACATAGACTTCAAGAATCCAATCCACGAGTCCTTCT
CGAAGTCGGGGCCCATGTTCACCCACAGACGTGTCGAGGAGACTTACACC
AAGGAGAACCTTGCCATGGTGGAGTACCAGCAGGTTTTCAACAGCGCCCC
AAGAGACATGTAG-3'

Polynucleotide (f1-46)
(SEQ ID NO: 95)
5'-ATGACAACCTTCAAAATCGAGTCCCGGATCCAAGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTGAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATGTCCCACGGTGGACCTGATGTTGCCGATGTCCGGGAACATCATCGCC
AGCTCCTACGCTTTGGCCTTCCAACTGAAGGACGGCTCTTTCTACACGGC
AGAAGTCAAGAACAACATAGACTTCAAGAATCCAATCCACGAGTCCTTCT
CGAAGTCGGGGCCCATGTTCACCCACAGACGTGTCGAGGAGACTTACACC
AAGGAGAACCTTGCCATGGTGGAGTACCAGCAGGTTTTCAACAGCGCCCC
AAGAGACATGTAG-3'

Polynucleotide (f1-47)
(SEQ ID NO: 96)
5'-ATGACAACCTTCAAAATCGAGTCCCGGATCCAAGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTGAGAACATCTATCTTCATGCTGCAACAAACGGAGGTTACACCA
ACACCAGGAAGGAGATCTATGAAGACGGCGGCATCTTGGAGGTTAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATGTCCCACGGTGGACCTGATGTTGCCGATGTCCGGGAACATCATCGCC
AGCTCCTACGCTTTGGCCTTCCAACTGAAGGACGGCTCTTTCTACACGGC
AGAAGTCAAGAACAACATAGACTTCAAGAATCCAATCCACGAGTCCTTCT
CGAAGTCGGGGCCCATGTTCACCCACAGACGTGTCGAGGAGACTCACACC
AAGGAGAACCTTGCCATAGTGGAGTACCAGCAGGTTTTCAACAGCGCCCC
AAGAGACATATAG-3'

Polynucleotide (f1-48)
(SEQ ID NO: 97)
5'-ATGACAACCTTCAAAATCGAGTCCCGGATCCACGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTGAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATGGCCCACGGTGGACCTGATGTTGCCGATGTCCGGGAACATCATCGCC
AGTTCCTACGCTTTGGCCTTCCAACTGAAGGACGGCTCTTTCTACACGGC
AGAGGTCAAGAACAACATAGACTTCAAGAATCCAATCCACGAGTCCTTCT
CGAAGTCGGGGCCCATGTTCACCCACAGACGTGTCGAGGAGACTCACACC
AAGGAGAACCTTGCCATAGTGGAGTACCAGCAGGTTTTCAACAGCGCCCC
AAGAGACATGTAG-3'

Polynucleotide (f1-49)
(SEQ ID NO: 98)
5'-ATGACAACCTTCAAAATCGAGTCCCGGATCCAAGGCAACCTCAACGG
GGAGAAGTTCGAGTTGGTTGGAGGTGGAGTAGGTGAGGAGGGTCGCCTCG
AGATTGAGATGAAGACTAAAGATAAACCACTGGCATTCTCTCCCTTCCTG
CTGTCCTGCTGCATGGGTTACGGGTTCTACCACTTCGCCAGCTTCCCAAA
GGGGACTGAGAACATCTATCTTCATGCTGCAACAAACGGAGGTTACACCA
ACACCAGGAAGGAGATCTATGAAGACGGCGGCATCTTGGAGGTCAACTTC
CGTTACACTTACGAGTTCAACAAGATCATCGGTGACGTCGAGTGCATTGG
ACATGGATTCCCAAGTCAGAGTCCGATCTTCAAGGACACGATCGTGAAGC
AATGGCCCACGGTGGACCTGATGTTGCCGATGTCCGGGAACATCATCGCC
AGTTCCTACGCTTTGGCCTTCCAACTGAAGGACGGCTCTTTCTACACGGC
AGAGGTCAAGAACAACATAGACTTCAAGAATCCAATCCACGAGTCCTTCT
CGAAGTCGGGGCCCATGTTCACCCACAGACGTGTCGAGGAGACTCACACC
AAGGAGAACCTTGCCATGGTGGAGTACCAGCAGGTTTTCAACAGCGCCCC
AAGAGACATGTAG-3'

Polynucleotide (f1-50)
(SEQ ID NO: 99)
5'-ATGACAACCTTCAAAATCGAGTCCCGGATCCAAGGCAACCTCAACGG
GGAGAAGTTCGAGTTGGTTGGAGGTGGAGTAGGTGAGGAGGGTCGCCTCG
AGATTGAGATGAAGACCAAAGATAAACCACTGGCATTCTCTCCCTTCCTG

CTGTCC[TGC]TGCATGGGTTACGGGTTCTACCACTTCGCCAGCTTCCCAAA

GGGGACTGAGAACATCTATCTTCATGCTGCAACAAACGGAGGTTACACCA

ACACCAGGAAGGAGATCTATGAAGACGGCGGCATCTTGAAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG[C]

[AA]TGTCCCACGGTGGACCTGATGTTGCCGATGTCCGGGAACATCATCGCC

AGCTCCTACGCT[TTG]GCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>TAC</u>ACC

AAGGAGAACCTTGCC<u>ATG</u>GTGGAGTACCAGCAGGTTTTCAACAGCGCCCC

AAGAGACATGTAG-3'

Polynucleotide (f1-51)
(SEQ ID NO: 100)
5'-ATGACAACCTTCAAAATCGAGTCCCGGATCCAAGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC[TGC]TGCATGGGTTACGGGTTCTACCACTTCGCCAGCTTCCCAAA

GGGGACTGAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG[C]

[AA]TGTCCCACGGTGGACCTGATGTTGCCGATGTCCGGGAACATCATCGCC

AGCTCCTACGCT[TTG]GCCTTCCAACTGGAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>TAC</u>ACC

AAGGAGAACCTTGCC<u>ATG</u>GTGGAGTACCAGCAGGTTTTCAACAGCGCCCC

AAGAGACATGTAG-3'

Polynucleotide (f1-52)
(SEQ ID NO: 101)
5'-ATGACAACCTTCAAAATCGAGTCCCGGATCCGTGGCAACCTCAACGG

GGAGAAGTTCGAGTTGGTTGGAGGTGGAGTAGGTGAGGAGGGTCGCCTCG

AGATTGAGATGAAGACTAAAGATAAACCACTGGCATTCTCTCCCTTCCTG

CTGTCC[TGC]TGCATGGGTTACGGGTTCTACCACTTCGCCAGCTTCCCAAA

GGGGACTGAGAACATCTATCTTCATGCTGCAACAAACGGAGGTTACACCA

ACACCAGGAAGGAGATCTATGAAGACGGCGGCATCTTGGAGGTCAACTTC

CGTTACACTTACGAGTTCAACAAGATCATCGGTGACGTCGAGTGCATTGG

ACATGGATTCCCAAGTCAGAGTCCGATCTTCAAGGACACGATCGTGAAG[C]

[AA]TGTCCCACGGTGGACCTGATGTTGCCGATGTCCGGGAACATCATCGCC

AGCTCCTACGCT[TTG]GCCTTCCAACTGAAGGACGGCTCTTTCTACACGGC

AGAAGTCAAGAACAACATAGACTTCAAGAATCCAATCCACGAGTCCTTCT

CGAAGTCGGGGCCCATGTTCACCCACAGACGTGTCGAGGAGACT<u>TAC</u>ACC

AAGGAGAACCTTGCC<u>ATG</u>GTGGAGTACCAGCAGGTTTTCAACAGCGCCCC

AAGAGACATGTAG-3'

It can be said that the polynucleotide (f2) is, for example, a polynucleotide encoding a protein having a fluorescence activity and consisting of a base sequence obtained by deletion, substitution, insertion, and/or addition of one to several bases in the polynucleotide (f1) in which the $N_{154}$, the $N_{155}$, the $N_{156}$, the $N_{397}$, the $N_{398}$, the $N_{399}$, the $N_{460}$, the $N_{461}$, and the $N_{462}$ are preserved. In the polynucleotide (f2), "one to several" can be a range in which a protein encoded by the polynucleotide (f2) has a fluorescence activity, for example. In the polynucleotide (f2), "one to several" can be, for example, 1 to 132, 1 to 99, 1 to 66, 1 to 33, 1 to 26, 1 to 20, 1 to 13, 1 to 7, 1, 2, 3, or 4. When the $N_{613}N_{614}N_{615}$ codon is substituted with a codon encoding I in the polynucleotide (f1), the polynucleotide (f2) is preferably a polynucleotide in which the $N_{613}$, the $N_{614}$, and the $N_{615}$ of the polynucleotide (f1) are preserved. In this case, the polynucleotide (f2) is, for example, a polynucleotide encoding a protein having a fluorescence activity and consisting of a base sequence obtained by deletion, substitution, insertion, and/or addition of one to several bases in the base sequence of the polynucleotide (f1) in which the $N_{154}$, the $N_{155}$, the $N_{156}$, the $N_{397}$, the $N_{398}$, the $N_{399}$, the $N_{460}$, the $N_{461}$, the $N_{462}$, the $N_{613}$, the $N_{614}$, and the $N_{615}$ are preserved. When the $N_{592}N_{593}N_{594}$ codon is substituted with a codon encoding L or H in the polynucleotide (f1), the polynucleotide (f2) is preferably a polynucleotide in which the $N_{592}$, the $N_{593}$, and the $N_{594}$ of the polynucleotide (f1) are preserved. In this case, the polynucleotide (f2) can be, for example, a polynucleotide encoding a protein having a fluorescence activity and consisting of a base sequence obtained by deletion, substitution, insertion, and/or addition of one to several bases in the base sequence of the polynucleotide (f1) in which the $N_{154}$, the $N_{155}$, the $N_{156}$, the $N_{397}$, the $N_{398}$, the $N_{399}$, the $N_{460}$, the $N_{461}$, the $N_{462}$, the $N_{592}$, the $N_{593}$, and the $N_{594}$ are preserved. When the combination of the $N_{592}N_{593}N_{594}$ codon and the $N_{613}N_{614}N_{615}$ codon is substituted with the combination of codons encoding L and I or the combination of codons encoding H and I, respectively, in the polynucleotide (f1), the polynucleotide (f2) is preferably a polynucleotide in which the $N_{154}$, the $N_{155}$, the $N_{156}$, the $N_{397}$, the $N_{398}$, the $N_{399}$, the $N_{460}$, the $N_{461}$, the $N_{462}$, the $N_{592}$, the $N_{593}$, the $N_{594}$, the $N_{613}$, the $N_{614}$, and the $N_{615}$ of the polynucleotide (f1) are preserved. In this case, the polynucleotide (f2) is, for example, a polynucleotide encoding a protein having a fluorescence activity and consisting of a base sequence obtained by deletion, substitution, insertion, and/or addition of one to several bases in the base sequence of the polynucleotide (f1) in which the $N_{154}$, the $N_{155}$, the $N_{156}$, the $N_{397}$, the $N_{398}$, the $N_{399}$, the $N_{460}$, the $N_{461}$, the $N_{462}$, the $N_{592}$, the $N_{593}$, the $N_{594}$, the $N_{613}$, the $N_{614}$, and the $N_{615}$ are preserved. Regarding the "one to several", reference can be made to the above description.

It can be said that the polynucleotide (f3) is, for example, a polynucleotide encoding a protein having a fluorescence activity and consisting of a base sequence having at least 80% identity to the base sequence of the polynucleotide (f1) in which the $N_{154}$, the $N_{155}$, the $N_{156}$, the $N_{397}$, the $N_{398}$, the $N_{399}$, the $N_{460}$, the $N_{461}$, and the $N_{462}$ are preserved. In the polynucleotide (f3), "identity" can be a range in which a protein encoded by the polynucleotide (f3) has a fluorescence activity, for example. In the polynucleotide (f3), "identity" is, for example, at least 80%, at least 85%, at least 90%, at least 95%, at least 96%, at least 97%, at least 98%, or at least 99%. When the $N_{613}N_{614}N_{615}$ codon is substituted with a codon encoding I in the polynucleotide (f1), the polynucleotide (f3) is preferably a polynucleotide in which the $N_{613}$, the $N_{614}$, and the $N_{615}$ of the polynucleotide (f1) are preserved. In this case, the polynucleotide (f3) can be, for example, a polynucleotide encoding a protein having a fluorescence activity and consisting of a base sequence having at least 80% identity to the base sequence of the polynucleotide (f1) in which the $N_{154}$, the $N_{155}$, the $N_{156}$, the $N_{397}$, the $N_{398}$, the $N_{399}$, the $N_{460}$, the $N_{461}$, the $N_{462}$, the $N_{613}$, the $N_{614}$, and the $N_{615}$ are preserved. When the $N_{592}N_{593}N_{594}$ codon is substituted with a codon encoding L or H in the polynucleotide (f1), the polynucleotide (f3) is preferably a polynucleotide in which the $N_{592}$, the $N_{593}$, and the $N_{594}$ of the polynucleotide (f1) are preserved. In this case, the polynucleotide (f3) is, for example, a polynucleotide encoding a protein having a fluorescence activity and consisting of a base sequence having at least 80% identity to the base sequence of the polynucleotide (f1) in which the $N_{154}$, the $N_{155}$, the $N_{156}$, the $N_{397}$, the $N_{398}$, the $N_{399}$, the $N_{460}$, the $N_{461}$, the $N_{462}$, the $N_{592}$, the $N_{593}$, and the $N_{594}$ are preserved. When the combination of the $N_{592}N_{593}N_{594}$ codon and the $N_{613}N_{614}N_{615}$ codon is substituted with the combination of codons encoding L and I or the combination of codons encoding H and I, respectively, in the polynucleotide (f1), the polynucleotide (f3) is preferably a polynucleotide in which the $N_{154}$, the $N_{155}$, the $N_{156}$, the $N_{397}$, the $N_{398}$, the $N_{399}$, the $N_{460}$, the $N_{461}$, the $N_{462}$, the $N_{592}$, the $N_{593}$, the $N_{594}$, the $N_{613}$, the $N_{614}$, and the $N_{615}$ of the polynucleotide (f1) are preserved. In this case, the polynucleotide (f3) is, for example, a polynucleotide encoding a protein having a fluorescence activity and consisting of a base sequence having at least 80% identity to the base sequence of the polynucleotide (f1) in which the $N_{154}$, the $N_{155}$, the $N_{156}$, the $N_{397}$, the $N_{398}$, the $N_{399}$, the $N_{460}$, the $N_{461}$, the $N_{462}$, the $N_{592}$, the $N_{593}$, the $N_{594}$, the $N_{613}$, the $N_{614}$, and the $N_{615}$ are preserved. Regarding the "identity", reference can be made to the above description.

In the polynucleotide (f4), the "polynucleotide that hybridizes to a polynucleotide" is, for example, a polynucleotide completely or partially complementary to the polynucleotide (f1). The hybridization can be detected, for example, by various hybridization assays. The hybridization assay is not limited to particular assays, and can be, for example, the method described in Sambrook et al. "Molecular Cloning: A Laboratory Manual 2nd Ed." [Cold Spring Harbor Laboratory Press (1989)].

In the polynucleotide (f4), the "stringent condition" can be any of a low stringent condition, a middle stringent condition, and a high stringent condition, for example. The "low stringent condition" refers to, for example, a condition in which 5×SSC, 5×Denhardt's solution, 0.5% SDS, and 50% formamide are used at 32° C. The "middle stringent condition" refers to, for example, a condition in which 5×SSC, 5×Denhardt's solution, 0.5% SDS, and 50% formamide are used at 42° C. The "high stringent condition" refers to, for example, a condition in which 5×SSC, 5×Denhardt's solution, 0.5% SDS, and 50% formamide are used at 50° C. Those skilled in the art can adjust the degree of the stringency, for example, by appropriately selecting the conditions such as a temperature, a salt concentration, the concentration and the length of a probe, an ionic strength, time, and the like. The "stringent condition" can be, for example, the condition described in Sambrook et al. "Molecular Cloning: A Laboratory Manual 2nd Ed." [Cold Spring Harbor Laboratory Press (1989)].

The base sequence of the polynucleotide (f5) can be any base sequence as long as a protein encoded by the polynucleotide (f5) has a fluorescence activity, for example. The base sequence of the polynucleotide (f5) can be designed, for example, by substituting the codon(s) with a corresponding codon(s) based on the amino acid sequence of SEQ ID NO: 1 and the amino acids $Xaa_{52}$, $Xaa_{133}$, and $Xaa_{154}$. It can be said that the protein encoded by the polynucleotide (f5) is, for example, the protein (F1) described in the description as to the novel protein of the present invention, and the reference can be made as to the description.

When the combination of the amino acids $Xaa_{52}$, $Xaa_{133}$, and $Xaa_{154}$ of the protein encoded by the polynucleotide (f5) i.e., the protein (F1) is the combination of the amino acids $Xaa_{52}$, $Xaa_{133}$, and $Xaa_{154}$ of the protein (B1), the polynucleotide (f5) is also referred to as a polynucleotide (b5), and the polynucleotides (f6) and (f7) are also referred to as polynucleotides (b6) and (b7) when the polynucleotide (f5) is the polynucleotide (b5). Also in the description below, regarding the polynucleotides (b6) and (b7), for example, reference can be made to the description as to the polynucleotides (f6) and (f7) by replacing (f6) with (b6), (f7) with (b7), (F2) with (B2), and (F3) with (B3), respectively.

In the polynucleotide (f6), "one to several" can be a range in which a protein encoded by the polynucleotide (f6) has a fluorescence activity, for example. In the polynucleotide (f6), "one to several" can be, for example, 1 to 43, 1 to 33, 1 to 22, 1 to 11, 1 to 9, 1 to 7, 1 to 5, 1 to 3, 1, or 2. The protein encoded by the polynucleotide (f6) can be, for example, the protein (F2) described in the description as to the novel protein of the present invention, and the reference can be made as to the description.

In the polynucleotide (f7), "identity" can be a range in which a protein encoded by the polynucleotide (f7) has a fluorescence activity, for example. In the polynucleotide (f7), "identity" is, for example, at least 80%, at least 85%, at least 90%, at least 95%, at least 96%, at least 97%, at least 98%, or at least 99%. The protein encoded by the polynucleotide (f7) can be, for example, the protein (F3) described in the description as to the novel protein of the present invention, and the reference can be made as to the description.

In the present invention, the above-described polynucleotides can be produced, for example, by a publicly known genetic engineering method or synthesis method.

<Expression Vector of Novel Protein>

The expression vector of the present invention includes the novel gene of the present invention as described above. According to the expression vector of the present invention, for example, by transfecting the expression vector to the host, the novel protein of the present invention can be produced readily. Regarding the expression vector of the present invention, reference can be made to the description as to the novel gene of the present invention, for example.

The expression vector can be any vector as long as it functionally includes the polynucleotide such that a novel protein encoded by the polynucleotide which is the novel gene of the present invention can be expressed, for example, and the other configurations are by no means limited.

The expression vector can be produced by inserting the polynucleotide into a vector serving as a skeleton (hereinafter, also referred to as a "basic vector"), for example. The type of the vector is not limited to particular types and can be determined appropriately according to the type of the host, for example. The vector can be a viral vector or a non-viral vector. The vector is preferably a binary vector, for example. For the transformation of a plant, the vector is preferably a T-DNA binary vector. For the transformation of a plant by the method using *Agrobacterium*, the vector can be, for example, a pBI121 vector, a pPZP202 vector, a pBINPLUS vector, a pBIN19 vector, a pBIG2113N vector, a pBIG2113SF vector, a pRI101DNA vector (products of TAKARA BIO INC.), a pRI201DNA vector (product of TAKARA BIO INC.), a pRI909DNA vector (product of TAKARA BIO INC.), and a pRI910DNA vector (product of TAKARA BIO INC.). For the transformation of microorganisms such as *Escherichia coli*, the vector can be, for example, a pETDuet-1 vector (product of Novagen), a pQE-80L vector (product of QIAGEN), a pBluescript II SK vector, a pET101/D-TOPO vector (product of Invitrogen Corporation), a pGEX-6P-1 vector (product of Amersham Biosciences), a pcDNA3.2/V5-GW/D-TOPO vector (product of Invitrogen Corporation), a pEGFP vector, and a pcDNA3.1-hygro (−) vector (product of Invitrogen Corporation).

The expression vector preferably includes a regulatory sequence for regulating the expression of the polynucleotide and the expression of the novel protein of the present invention encoded by the polynucleotide, for example. The regulatory sequence can be, for example, a promoter, a terminator, an enhancer, a polyadenylation signal sequence, and an origin of replication sequence (ori). In the expression vector, the position of the regulatory sequence is not particularly limited. The regulatory sequence can be placed at any position in the expression vector as long as it functionally regulates the expression of the polynucleotide and the expression of the novel protein encoded by the polynucleotide. The regulatory sequence can be placed according to the publicly known method, for example. For example, a sequence preliminarily contained in the basic vector may be used as the regulatory sequence, the regulatory sequence may be inserted into the basic vector, or a regulatory sequence contained in the basic vector may be substituted with another regulatory sequence.

The expression vector may further include a coding sequence of a selection marker, for example. The selection marker can be, for example, a pharmaceutical composition-resistant marker, a fluorescent protein marker, an enzyme marker, and a cell surface receptor marker.

<Production Method of Novel Protein>

The production method of the novel protein of the present invention is not limited to particular methods, and can be, for example, a publicly known genetic engineering method, synthesis method, and the like. In the former case, the production method of the present invention includes a step of expressing the novel gene of the present invention. Thereby, the production method of the novel protein of the present invention can produce the novel fluorescent protein of the present invention readily.

The expression of the polynucleotide which is the novel gene of the present invention can be performed using the expression vector of the present invention, for example.

The method for expressing the polynucleotide is not limited to particular methods and can be a publicly known method. For example, a cell-free protein synthesizing system, a host, and the like can be used for the expression.

In the former case, preferably, the polynucleotide is expressed in the cell-free protein synthesizing system. In this case, an expression vector may be used for the expression of the polynucleotide. The cell-free protein synthesizing system can be performed, for example, by a publicly known method using a cell extract, a buffer including various components, and an expression vector to which an intended polynucleotide has been transfected. For example, a commercially available reagent kit can be used.

In the latter case, preferably, a host to which the polynucleotide has been transfected is used and the polynucleotide is expressed in the host by culturing the host, for example. For example, a transformant that synthesizes the novel protein of the present invention can be produced by transfecting the polynucleotide to the host, and the novel protein of the present invention can be synthesized by culturing the transformant.

Examples of the host include nonhuman hosts such as microorganisms, plants, animals, insects, and the cultured cells thereof; isolated human cells; and the cultured cells thereof. Among them, plants are preferable. When the host is a plant, the plant can be, for example, a planta or a part of the planta. Examples of the part of planta include organs, tissues, cells, and propagules. Examples of the organ include petals, corollas, flowers, leaves, seeds, fruits, stems, and roots. The tissue can be, for example, a part of the organ. The cell can be, for example, the planta or a cell collected from the tissue of the planta, a cultured cell of the cell collected from the tissue of the planta, protoplast, and callus. The origin of the plant is not limited to particular origins and can be, for example, Brassicaceae, Solanaceae, Poaceae, Fabaceae, Rosaceae, Caryophyllaceae, Asteraceae, Gentianaceae, Scrophulariaceae, Verbenaceae, Primulaceae, Cactaceae, Orchidaceae, and the like. The Brassicaceae can be, for example, *Arabidopsis* such as *Arabidopsis thaliana* and the like. The Solanaceae can be, for example, *Nicotiana* such as *Nicotiana tabacum* and the like; *Petunia* such as *Petunia*× *hybrid* and the like; *Nierembergia* such as *Nierembergia hippoamanica* and the like; *Calibrachoa* such as *Calibrachoa hybrid Cultivar* and the like; and the like. The Poaceae can be, for example, *Zea* such as *Zea mays* and the like; *Oryza* such as *Oryza sativa* and the like; and the like. The Fabaceae can be, for example, *Glycine* such as *Glycine max* and the like. The Rosaceae can be, for example, Rosa such as Rosa and the like. The Caryophyllaceae can be, for example, *Dianthus* such as *Dianthus caryophyllus* and the like. The Asteraceae can be, for example, *Chrysanthemum* such as *Chrysanthemum morifolium* and the like; *Gerbera* such as *Gerbera cvs.* and the like; and the like. The Gentianaceae can be, for example, *Eustoma* such as *Eustoma grandiflorum* and the like. The Scrophulariaceae can be, for example, *Torenia* such as *Torenia fournieri* and the like. The Verbenaceae can be, for example, *Verbena* such as *Garden verbena* and the like. The Primulaceae can be, for example, *Cyclamen* such as *Cyclamen persicum* and the like. Examples of the Cactaceae include Austrocylindropuntia, Astrophytum, Echinocactus, Echinocereus, Echinopsis, Epiphyllum, Opuntia, Schlumbergera russeliana, Chamaecereus, Cylindropuntia, Gymnocalycium, Schlumbergera truncata, Selenicereus, Tephrocactus, Neobuxbaumia, Neoraimondia, Nopalea, Ferocactus, Mammillaria, Melocactus, Rhipsalis, Roseocactus, and Lophophora. Examples of the Orchidaceae include *Phalaenopsis* such as *Phalaenopsis cvs.* and the like; *Cymbidium* such as *Cymbidium cvs.* and the like; *Dendrobium* such as *Dendrobium nobile* hybrids, *D. phalaenopsis* hybrids, and the like; *Oncidium* such as *Oncidium cvs.* and the like; and *Cattleya* such as *Cattleya cvs.* and the like. Examples of the microorganisms include eukaryote and prokaryote. The prokaryote can be, for example, bacteria including *Escherichia* such as *Escherichia coli* and the like; *Pseudomonas* such as *Pseudomonas putida* and the like. The eukaryote can be, for example, yeast such as *Saccharomyces cerevisiae* and the like. Examples of the animal cell include a COS cell and a CHO cell. Examples of the insect cell include Sf9 and Sf21.

The method for transfecting the polynucleotide to the host i.e., the method for the transformation of the host is not limited to particular methods, and can be, for example, a method using the expression vector or a publicly known method without using the expression vector. In the latter case, the transfection method can be determined appropriately according to the type of the host, for example. Examples of the transfection method include a heat shock method, a lithium acetate method, a method using a gene gun such as a particle gun, a calcium phosphate method, a polyethylene glycol method, a lipofection method using liposome, an electroporation method, an ultrasonic nucleic acid transfection method, a DEAE-dextran method, a direct transfection method using a microglass tube, a hydrodynamic method, a cationic liposome method, a method using a transfection adjuvant, and a method through *Agrobacterium*. The liposome cab be, for example, Lipofectamine and cationic liposome, and the transfection adjuvant can be, for example, atelocollagen, nanoparticle, and polymer. When the host is a plant, the transfection method is preferably a method through *Agrobacterium*. The polynucleotide which is the novel gene of the present invention may be transfected to the host by the expression vector of the present invention, for example.

The method for culturing the host is not limited to particular methods and can be determined appropriately according to the type of the host. The culture medium used for culturing the host is not limited to particular media and can be determined appropriately according to the type of the host.

The form of the culture medium used for culturing the host is not limited to particular forms and can be, for example, a publicly known culture medium such as a solid culture medium, a liquid culture medium, an agar culture medium, or the like. The component contained in the culture medium are not limited to particular components. The culture medium may contain a commercially available culture medium, for example. When the host is a plant, a commercially available culture medium of the plant is not limited to particular media and can be, for example, a Murashige-Skoog (MS) culture medium and the like. When the host is a plant cell, a commercially available culture medium of the plant cell is not limited to particular media and can be, for example, a hyponex culture medium, an MS culture medium, a Gamborg B5 (B5) culture medium, a White culture medium, and the like. When the host is microorganisms, a commercially available culture medium of microorganisms is not limited to particular media and can be, for example, an LB culture medium, a Super Broth culture medium, an M9 culture medium, and the like. One of the culture media can be used alone of two or more of them may be used in combination, for example. The pH of the culture medium is not particularly limited and is, for example, in the range from pH6 to pH 8 or from pH6.5 to pH 7.5.

The method for culturing the host is not limited to particular methods and can be determined appropriately according to the type of the host, for example. When the host is a plant, the method for culturing can be, for example, the soil cultivation of a plant, the hydroponics of a plant, and the like. When the plant is a plant cell, the method for culturing can be, for example, a callus culture, a root culture, an ovule culture, an embryo culture, and the like.

The culture temperature of the host is not particularly limited and can be determined appropriately according to the type of the host, for example. When the host is a plant, the culture temperature can be, for example, a viable temperature of a plant, an optimal growth temperature of a plant, and the like. Specifically, the culture temperature is, for example, in the range from 15° C. to 40° C. or in the range from 30° C. to 37° C. When the host is a plant cell, the culture temperature can be, for example, a viable temperature of a plant cell, an optimal growth temperature of a plant cell, and the like. Specifically, the culture temperature is, for example, in the range from 15° C. to 40° C. or in the range from 30° C. to 37° C.

The host may be cultured under an aerobic condition or an anaerobic condition, for example. The aerobic condition and the anaerobic condition are not limited to particular conditions, and can be determined using a conventionally known method.

<Transformant>

The transformant of the present invention includes the novel gene of the present invention as described above. The transformant of the present invention is characterized in that it includes the novel gene of the present invention, and other configurations and conditions are by no means limited. The transformant of the present invention including the novel gene of the present invention has a fluorescence activity owing to the novel gene, for example. Regarding the transformant of the present invention, for example, reference can be made to the description as to the novel protein of the present invention and the like.

In the present invention, the transformant is not particularly limited and can be an animal, a plant, and the like. Among them, a plant is preferable. When the transformant is an animal, the transformant can be, for example, a cancer cell such as a human colon cancer cell. When the transformant is a plant, the plant and the origin of the plant are not particularly limited, and reference can be made to the above description, for example. Specifically, the plant can be, for example, a planta or a part of the planta. Examples of the part of planta include organs, tissues, cells, and propagules. Examples of the organ include petals, corollas, flowers, leaves, seeds, fruits, stems, and roots. The tissue can be, for example, a part of the organ. The cell can be, for example, the planta or a cell collected from the tissue of the planta, a cultured cell of the cell collected from the tissue of the planta, protoplast, and callus.

In the present invention, when the transformant is a plant, the transformant of the present invention can further be propagated, for example. On this occasion, the transformant of the present invention can be used as a propagation material. The propagation material is not particularly limited and can be, for example, the whole or a part of the transformant. When the transformant is the planta or a part of the planta, the propagation material can be, for example, a seed, a fruit, a shoot, a stem such as a tuber, a root such as a tuberous root, a strain, a protoplast, a callus, and the like.

The method for propagating the transformant of the present invention is not limited to particular methods and can be a publicly known method. The propagation method can be, for example, a sexual reproduction or an asexual reproduction, and the asexual reproduction is preferable.

The asexual reproduction can be, for example, a vegetative propagation, which is also called a vegetative reproduction. The vegetative propagation is not limited to particular methods. When the transformant is a planta or a part of the planta, the vegetative propagation can be, for example, propagation by cutting bud or tree, fragmentation from an organ to plant individuals, growth by a callus, and the like. As the organ, for example, the leaves, stems, and roots described above can be used.

The propagule obtained by propagating the transformant vegetatively is referred to as the propagule of the present invention hereinbelow. The propagule of the present invention preferably has the same properties as the transformant of the present invention. As in the transformant, the propagule of the present invention is not particularly limited and can be, for example, a planta or a part of the planta.

When the transformant is sexually reproduced, for example, a seed, a descendant such as a growing material grown from the seed can be obtained. The descendant of the present invention preferably has the same properties as the transformant of the present invention. As in the transformant, the descendant of the present invention can be, for example, a planta or a part of the planta.

The transformant of the present invention may further be processed, for example. The type of the transformant to be processed is not limited to particular types and can be, for example, a flower, a leaf, a branch, and the like. The processed product of the transformant is not limited to particular products and can be, for example, a potpourri made by drying a flower, a leaf, a branch, or the like; a pressed flower; a dried flower; a preserved flower; a resin sealed product; and the like. The processed product of the present invention can be, for example, a processed product of the propagule, organ, tissue, or cell of the transformant.

<Production Method of Transformant>

The method for producing a transformant of the present invention includes a step of transfecting the novel gene according to the present invention to a host as described above. The production method of the transformant of the present invention is characterized in that it includes a step of transfecting the novel gene according to the present invention to a host, and other steps and conditions are by no means limited. According to the production method of the transformant of the present invention, for example, the transformant of the present invention can be produced readily.

The method for producing a transformant of the present invention may further include a step of expressing the novel gene in the host.

In the transfection step, the method for transfecting the novel gene of the present invention to the host is not limited to particular methods, and reference can be made to the description as to the method for transfecting the polynucleotide to host in the production method of the novel protein of the pre sent invention, for example. In the production method of the transformant of the present invention, the host is preferably a plant.

The expression step is a step of expressing the novel protein of the present invention from the novel gene of the present invention in the host, for example. In the expression step, for example, the host is preferably a transformant to which the novel gene or expression vector of the present invention has transfected and the novel protein of the present invention is preferably expressed in the host by culturing the transformant.

When the host is a plant, the method for producing a transformant of the present invention may further include a step of propagating the transformant obtained in the transfection step. Regarding the propagation method in the propagation step, for example, reference can be made to the above description. The method for producing a transformant of the present invention may further include a step of producing a seed from the propagated transformant and a step of growing a growing material from the seed obtained in the seed production step.

<Screening Method of Novel Fluorescent Protein>

The method for screening the novel fluorescent protein of the present invention (hereinafter, also referred to as "the screening method of the present invention".) is characterized in that it includes a step of selecting a protein having a fluorescence activity in which each of an amino acid corresponding to the 52nd amino acid $Xaa_{52}$, an amino acid corresponding to the 133rd amino acid $Xaa_{133}$, and an amino acid corresponding to the 154th amino acid $Xaa_{154}$ in the amino acid sequence of SEQ ID NO: 1 is an arbitrary amino acid from a candidate protein obtained by introducing a mutation to the novel protein according to the present invention as described above, and other steps and conditions are by no means limited. According to the screening method of the present invention, for example, a protein having a fluorescence activity can be screened easily. Regarding the screening method of the present invention, for example, reference can be made to the description as to the novel protein, novel gene, expression vector, production method, and the like of the present invention.

The candidate protein is a protein obtained by introducing a mutation to the novel protein of the present invention. The type of the mutation to be introduced to the novel protein is not limited to particular types and can be, for example, deletion, substitution, insertion, and/or addition of an amino acid(s). As a specific example, the candidate protein can be, for example, a protein consisting of an amino acid sequence obtained by deletion, substitution, insertion, and/or addition of one to several amino acids in the amino acid sequence of the novel protein or a protein consisting of an amino acid sequence having at least 80% identity to the amino acid sequence of the novel protein.

In the amino acid sequence of the candidate protein, "one to several" is, for example, 1 to 43, 1 to 33, 1 to 22, 1 to 11, 1 to 9, 1 to 7, 1 to 5, 1 to 3, 1, or 2.

In the amino acid sequence of the candidate protein, "identity" is, for example, at least 80%, at least 85%, at least 90%, at least 95%, at least 96%, at least 97%, at least 98%, or at least 99%.

The candidate protein can be produced by a publicly known protein synthesis method or genetic engineering method based on the amino acid sequence of the candidate protein. In the latter case, the screening method of the present invention includes, for example, a step of introducing a mutation to a base sequence encoding the novel protein i.e., the novel gene of the present invention to produce a mutation polynucleotide and a step of expressing the candidate protein from the mutation polynucleotide.

In the mutation step, the mutation to be introduced to the novel gene is not limited to particular mutations and can be, for example, deletion, substitution, insertion, and/or addition of a base. The method for introducing a mutation to the novel gene is not limited to particular methods and can be, for example, a publicly known method for introducing a mutation to a polynucleotide. As a specific example, the method for introducing a mutation can be a method of reconstructing a gene (so called DNA shuffling) by the random fragmentation and the recombination using PCR of the polynucleotide of the novel gene of the present invention.

In the expression step, the method for expressing the mutation polynucleotide is not limited to particular methods. Regarding the method for expressing the mutation polynucleotide, for example, reference can be made to the description as to the production method of the novel protein of the present invention, and either a cell-free protein synthesizing system or a host may be used. As the host, for example, prokaryote, especially, *Escherichia coli* is preferably used.

The screening method of the present invention may include a step of purifying the candidate protein obtained in the expression step, for example. The purification method is not limited to particular methods and examples thereof include salting out and various kinds of column chromatography. The solvent to be used in the purification step is not limited to particular solvents and can be, for example, a buffer solution. In the screening method of the present invention, for example, the candidate protein obtained in the expression step may be used directly in the selection step described below or a partially purified candidate protein or a singly purified candidate protein may be used.

The selection step is a step of selecting a protein having a fluorescence activity in which each of an amino acid corresponding to the 52nd amino acid $Xaa_{52}$, an amino acid corresponding to the 133rd amino acid $Xaa_{133}$, and an amino acid corresponding to the 154th amino acid $Xaa_{154}$ in the amino acid sequence of SEQ ID NO: 1 is an arbitrary amino acid from the candidate protein.

An amino acid corresponding to the $Xaa_{52}$ of the candidate protein selected in the selection step is an arbitrary amino acid. The arbitrary amino acid is A, C, D, E, F, G, H, I, K, L, M, N, P, Q, R, S, T, V, W, or Y, is preferably C, F, H, K, M, or T, and is more preferably C, M, or T as it shows stronger fluorescence even with excitation light having a relatively low wavelength, for example. In the selected candidate protein, the $Xaa_{52}$ is more preferably H as it shows stronger fluorescence under excitation with excitation light at the same intensity, for example.

The $Xaa_{133}$ of the selected candidate protein is an arbitrary amino acid. The arbitrary amino acid is A, C, D, E, F, G, H, I, K, L, M, N, P, Q, R, S, T, V, W, or Y, and is preferably L, Q, S, or T. In the selected candidate protein, the $Xaa_{133}$ is more preferably T as it shows stronger fluorescence under excitation with excitation light at the same intensity, for example.

In the selected candidate protein, the $Xaa_{154}$ is an arbitrary amino acid. The arbitrary amino acid is A, C, D, E, F, G, H, I, K, L, M, N, P, Q, R, S, T, V, W, or Y, is preferably A, H, I, K, L, Q, V, or Y, and is more preferably A, I, L, V, or Y as it shows stronger fluorescence even with excitation light having a relatively low wavelength, for example. In the selected candidate protein, the $Xaa_{154}$ is more preferably K as it shows stronger fluorescence under excitation with excitation light at the same intensity, for example.

The candidate protein selected in the selection step is a protein having a fluorescence activity in which the amino acid corresponding to the $Xaa_{52}$ is C, F, H, K, M, or T, the amino acid corresponding to the $Xaa_{133}$ is L, Q, S, or T, and the amino acid corresponding to the $Xaa_{154}$ is A, H, I, K, L, Q, V, or Y in the amino acid sequence of SEQ ID NO: 1.

The candidate protein selected in the selection step is a protein having a fluorescence activity in which the combination of amino acids corresponding to the $Xaa_{52}$, $Xaa_{133}$, and the $Xaa_{154}$ in the amino acid sequence of SEQ ID NO: 1 is one of the following combinations (aa1) to (aa12). The candidate protein selected in the selection step is a protein having a fluorescence activity in which the combination of amino acids corresponding to the $Xaa_{52}$, the $Xaa_{133}$, and the $Xaa_{154}$ is the following combination (aa1), (aa3), (aa6), (aa9), (aa10), or (aa12) or a protein having a fluorescence activity in which the combination of amino acids corresponding to the $Xaa_{52}$, the $Xaa_{133}$, and the $Xaa_{154}$ is the following combination (aa1) or (aa9) as it shows stronger fluorescence even with excitation light having a relatively low wavelength, for example. The candidate protein selected in the selection step is a protein having a fluorescence activity in which the combination of amino acids corresponding to the $Xaa_{52}$, the $Xaa_{133}$, and the $Xaa_{154}$ is the following combination (aa2) as it shows stronger fluorescence under excitation with excitation light at the same intensity, for example.

TABLE 4

|        | $Xaa_{52}$ | $Xaa_{133}$ | $Xaa_{154}$ |
|--------|------------|-------------|-------------|
| (aa1)  | T          | S           | Y           |
| (aa2)  | H          | T           | K           |
| (aa3)  | C          | L           | L           |
| (aa4)  | C          | S           | H           |
| (aa5)  | T          | S           | H           |
| (aa6)  | M          | L           | V           |
| (aa7)  | F          | S           | Q           |
| (aa8)  | K          | T           | A           |
| (aa9)  | C          | Q           | L           |
| (aa10) | T          | T           | I           |
| (aa11) | K          | S           | Q           |
| (aa12) | M          | L           | A           |

The candidate protein selected in the selection step is preferably a protein having a fluorescence activity in which the $Xaa_{205}$ is substituted with I as it shows stronger fluorescence even with excitation light having a relatively low wavelength, for example. The candidate protein selected in the selection step is preferably a protein having a fluorescence activity in which the $Xaa_{198}$ is substituted with L or H as it shows stronger fluorescence even with excitation light having a relatively low wavelength, for example. The candidate protein selected in the selection step is preferably a protein having a fluorescence activity in which the $Xaa_{198}$ and the $Xaa_{205}$ are substituted with the combination of L and I or H and I as it shows further stronger fluorescence even with excitation light having a relatively low wavelength, for example.

In the selection step, the method for identifying the amino acid sequence of the candidate protein is not limited to particular methods, and can be, for example, a publicly known amino acid identification method. When the candidate protein is expressed from the mutation polynucleotide, the amino acid sequence of the candidate protein can be identified by substituting the codon of the base sequence of the mutation polynucleotide with a corresponding amino acid sequence, for example.

In the selection step, the method for examining the fluorescence activity of the candidate protein is not limited to particular methods, and can be a publicly known fluorescence activity examination method. For example, the fluorescence activity of the candidate protein can be examined by measuring the spectrum of the fluorescence generated by the excitation light at each excitation wavelength using a publicly known optical measuring instrument. When the candidate protein is expressed in *Escherichia coli* (*Escherichia coli*), the method for examining the fluorescence activity is not limited to particular methods. For example, the fluorescence activity can be examined using a light emitting diode ultra violet (LEDUV) light source and an UV transmission filter.

In the selection step in the screening method of the present invention, preferably, a protein having a fluorescence activity and consisting of an amino acid sequence having at least 80% identity to the amino acid sequence of SEQ ID NO: 1 is selected. The "identity" can be a range in which the selected candidate protein has the fluorescence activity, for example. The "identity" is, for example, at least 80%, at least 85%, at least 90%, at least 95%, at least 96%, at least 97%, at least 98%, or at least 99%.

EXAMPLE

The examples of the present invention are described below. The present invention, however, is not limited by the following examples.

Example 1

The fluorescence activity of the novel protein of the present invention was examined.

(1) Construction of Expression Vector

Twelve kinds of vector insertion sequences (SEQ ID NO: 33) each including one of the novel genes (SEQ ID NOs: 17, 18, 20, 21, 23, 25 to 27, and 29 to 32) which encode the novel fluorescent proteins (SEQ ID NOs: 2 to 13), respectively, were obtained by a chemical synthesis. In the vector insertion sequence, the underlined base sequence within parentheses is a base sequence corresponding to the novel gene encoding the novel fluorescent protein. The relationships between the boxed $N_{154}N_{155}N_{156}$ codon, $N_{397}N_{398}N_{399}$ codon, and $N_{460}N_{461}N_{462}$ codon and the novel fluorescent protein and the novel gene in the vector insertion sequence are shown in the following table 5. The vector insertion sequences in each of which the combination of the $N_{154}N_{155}N_{156}$ codon, $N_{397}N_{398}N_{399}$ codon, and $N_{460}N_{461}N_{462}$ codon was one of (f1-3), (f1-4), (f1-6), (f1-7), (f1-9), (f1-11) to (f1-13), and (f1-15) to (f1-18) were referred to as the vector insertion sequences (f1-3), (f1-4), (f1-6), (f1-7), (f1-9), (f1-11) to (f1-13), and (f1-15) to (f1-18), respectively.

Vector insertion sequence
(SEQ ID NO: 33)
5'-AAGCTTG[ATGACAACCTTCAAAATCGAGTCCCGGATCCATGGCAAC
CTCAACGGGGAGAAGTTCGAGTTGGTTGGAGGTGGAGTAGGTGAGGAGGG
TCGCCTCGAGATTGAGATGAAGACTAAAGATAAACCACTGGCATTCTCTC
CCTTCCTGCTGTCC[NNN]TGCATGGGTTACGGGTTCTACCACTTCGCCAGC
TTCCCAAAGGGGACTAAGAACATCTATCTTCATGCTGCAACAAACGGAGG
TTACACCAACACCAGGAAGGAGATCTATGAAGACGGCGGCATCTTGGAGG
TCAACTTCCGTTACACTTACGAGTTCAACAAGATCATCGGTGACGTCGAG
TGCATTGGACATGGATTCCCAAGTCAGAGTCCGATCTTCAAGGACACGAT
CGTGAAG[NNN]TGTCCCACGGTGGACCTGATGTTGCCGATGTCCGGGAACA
TCATCGCCAGCTCCTACGCT[NNN]GCCTTCCAACTGAAGGACGGCTCTTTC
CTACACGGCAGAAGTCAAGAACAACATAGACTTCAAGAATCCAATCCACG
AGTCCTTCTCGAAGTCGGGGCCCATGTTCACCCACAGACGTGTCGAGGAG
ACTCACACCAAGGAGAACCTTGCCATGGTGGAGTACCAGCAGGTTTTCAA
CAGCGCCCCAAGAGACATGTAG]AATTC-3'

TABLE 5

| | $N_{154}N_{155}N_{156}$ | $N_{397}N_{398}N_{399}$ | $N_{460}N_{461}N_{462}$ | Protein | Gene |
|---|---|---|---|---|---|
| (f1-3) | ACT | AGT | TAC | SEQ ID NO: 2 | SEQ ID NO: 17 |
| (f1-4) | CAC | ACT | AAG | SEQ ID NO: 3 | SEQ ID NO: 18 |
| (f1-6) | TGC | TTA | CTT | SEQ ID NO: 4 | SEQ ID NO: 20 |
| (f1-7) | TGC | AGC | CAT | SEQ ID NO: 5 | SEQ ID NO: 21 |
| (f1-9) | ACG | AGC | CAC | SEQ ID NO: 6 | SEQ ID NO: 23 |
| (f1-11) | ATG | CTC | GTG | SEQ ID NO: 7 | SEQ ID NO: 25 |
| (f1-12) | AAA | AGC | CAA | SEQ ID NO: 8 | SEQ ID NO: 26 |
| (f1-13) | AAA | ACT | GCT | SEQ ID NO: 9 | SEQ ID NO: 27 |
| (f1-15) | TGC | CAA | TTG | SEQ ID NO: 10 | SEQ ID NO: 29 |
| (f1-16) | ACT | ACA | ATT | SEQ ID NO: 11 | SEQ ID NO: 30 |
| (f1-17) | AAA | AGC | CAA | SEQ ID NO: 12 | SEQ ID NO: 31 |
| (f1-18) | ATG | CTC | GCC | SEQ ID NO: 13 | SEQ ID NO: 32 |

The vector insertion sequences (f1-3), (f1-4), (f1-6), (f1-7), (f1-9), (f1-11) to (f1-13), and (f1-15) to (f1-18) each were cleaved by restriction enzymes HindIII and EcoRI and each of the resultants was linked to the pEGFP vector (product of CLONTEC) cleaved by the restriction enzymes. The vectors into which the vector insertion sequences (f1-3), (f1-4), (f1-6), (f1-7), (f1-9), (f1-11) to (f1-13), and (f1-15) to (f1-18) were inserted were referred to as the expression vectors (f1-3), (f1-4), (f1-6), (f1-7), (f1-9), (f1-11) to (f1-13), and (f1-15) to (f1-18), respectively. The expression vector was constructed by Gene Script.

(2) Transfection to *Escherichia coli*

Each of the expression vectors (f1-3), (f1-4), (f1-6), (f1-7), (f1-9), (f1-11) to (f1-13), and (f1-15) to (f1-18) alone was transfected to the *Escherichia coli* DH5a strain by a heat shock method. Each of the obtained transformants was cultured at 37° C. for 10 hours using an LB culture medium containing 100 µg/mL antibiotic (ampicillin). Then each of the cultured bacterial cells is collected, and the obtained pellet was washed twice using 40 mL of PBS solution containing one tablet of protease inhibitor (cOmplete, product of EDTA-free, Roche Ltd). Each of the washed pellet was suspended in 800 µL of PBS solution containing the protease inhibitor. Subsequently, each of the obtained suspensions was sonicated twice with Amp 25% for 1 minute using an ultrasonic homogenizer (QSONICA, WAKENBTECH CO., LTD). Then, each of the treated suspensions was centrifuged with 1300 rpm at 4° C. for 10 minutes, and the obtained supernatant was recovered. Hereinafter, the supernatants obtained from the transformants to which the expression vectors (f1-3), (f1-4), (f1-6), (f1-7), (f1-9), (f1-11) to (f1-13), and (f1-15) to (f1-18) have transfected were referred to as proteins (F1-1) to (F1-12) protein, respectively. The concentration of the protein in each supernatant was determined by adding Protein Assay (product of Bio Rad) to the supernatant and measuring the absorbance at 595 nm by a microplate reader (Infinite® M1000Pro, product of TECAN).

(3) Measurement of Fluorescence Activity

Each supernatant obtained in the transfection (2) was diluted based on the concentration of the protein in each supernatant obtained in the transfection (2) so that the concentration of the protein in the supernatant was 0.2 mg/mL. The fluorescence intensity (FI) of 50 µL of each supernatant after dilution was measured with the microplate reader under the measurement conditions described below. As a negative control, the fluorescence intensity (FI) was measured in the same manner as described above except that the pUC vector was transfected instead of the expression vector.

(Measurement Condition)

Excitation wavelength: 350 to 650 nm (band width: 5 nm)
Fluorescence (detection) wavelength: 350 to 650 nm (band width: 5 nm)
laser intensity (Gain): 105

The results obtained in the case where the excitation wavelength (Ex) was 375 nm and the fluorescence wavelength (Em) was 515 nm are shown in the following table 6A, the results obtained in the case where the excitation wavelength was 405 nm and the fluorescence wavelength was 515 nm are shown in the following table 6B, the results obtained in the case where the excitation wavelength was 500 nm and the fluorescence wavelength was 525 nm are shown in the following table 6C, and the results obtained in the case where the excitation wavelength was 510 nm and the fluorescence wavelength was 535 nm are shown in the following table 6D. As shown in the following tables 6A to 6D, the proteins (F1-1) to (F1-12) each showed a fluorescence activity at every wavelength. In contrast, the negative control (pUC) did not show a fluorescence activity. As shown in the table 6A, in the case where the excitation wavelength was 375 nm and the fluorescence wavelength was 515 nm, the proteins (F1-1) to (F1-6), (F1-9), (F1-10), and (F1-12) each showed a strong fluorescence activity, and the protein (F1-9) showed a significantly strong fluorescence activity. As shown in the table 6B, in the case where the excitation wavelength was 405 nm and the fluorescence wavelength was 515 nm, the proteins (F1-1), (F1-2), (F1-4), and (F1-9) each showed a strong fluorescence activity, and the protein (F1-9) showed a significantly strong fluorescence activity. As shown in the table 6C, in the case where the excitation wavelength was 500 nm and the fluorescence wavelength was 525 nm, the protein (F1-2) showed a strong fluorescence activity. As shown in the table 6D, in the case where the excitation wavelength was 510 nm and the fluorescence wavelength was 535 nm, the protein (F1-2) showed a strong fluorescence activity. Although it is not shown in the tables, also in the cases of using expression vectors each including one of the polynucleotides (f1-1) and (f1-2) each encoding the amino acid sequence of (F1-1), the polynucleotide (f1-5) encoding the amino acid sequence of (F1-2), the polynucleotide (f1-8) encoding the amino acid sequence of (F1-4), the polynucleotide (f1-10) encoding the amino acid sequence of (F1-6), and the polynucleotide (f1-14) encoding the amino acid sequence (F1-9) instead of the expression vector, the proteins each showed a fluorescence activity. These results showed that the novel fluorescent protein of the present invention has a fluorescence activity.

TABLE 6A

| Excitation wavelength = 375 nm Fluorescence wavelength = 515 nm | Fluorescence intensity (FI) |
|---|---|
| F 1-1 | 784 |
| F 1-2 | 172 |
| F 1-3 | 371 |
| F 1-4 | 409 |
| F 1-5 | 175 |
| F 1-6 | 166 |
| F 1-7 | 33 |
| F 1-8 | 50 |
| F 1-9 | 906 |
| F 1-10 | 266 |
| F 1-11 | 33 |
| F 1-12 | 258 |
| pUC | 17 |

TABLE 6B

| Excitation wavelength = 405 nm Fluorescence wavelength = 515 nm | Fluorescence intensity (FI) |
|---|---|
| F 1-1 | 1071 |
| F 1-2 | 1170 |
| F 1-3 | 464 |
| F 1-4 | 713 |
| F 1-5 | 267 |
| F 1-6 | 182 |
| F 1-7 | 91 |
| F 1-8 | 72 |
| F 1-9 | 1402 |
| F 1-10 | 304 |
| F 1-11 | 141 |
| F 1-12 | 275 |
| pUC | 10 |

TABLE 6C

| Excitation wavelength = 500 nm Fluorescence wavelength = 525 nm | Fluorescence intensity (FI) |
|---|---|
| F 1-1 | 170 |
| F 1-2 | 100401 |

TABLE 6C-continued

| Excitation wavelength = 500 nm Fluorescence wavelength = 525 nm | Fluorescence intensity (FI) |
|---|---|
| F 1-3 | 3034 |
| F 1-4 | 3022 |
| F 1-5 | 1572 |
| F 1-6 | 1407 |
| F 1-7 | 248 |
| F 1-8 | 2518 |
| F 1-9 | 6335 |
| F 1-10 | 2910 |
| F 1-11 | 387 |
| F 1-12 | 2341 |
| pUC | 9 |

TABLE 6D

| Excitation wavelength = 510 nm Fluorescence wavelength = 535 nm | Fluorescence intensity (FI) |
|---|---|
| F 1-1 | 108 |
| F 1-2 | 64915 |
| F 1-3 | 2417 |
| F 1-4 | 1219 |
| F 1-5 | 724 |
| F 1-6 | 1081 |
| F 1-7 | 67 |
| F 1-8 | 1108 |
| F 1-9 | 2864 |
| F 1-10 | 2181 |
| F 1-11 | 104 |
| F 1-12 | 1876 |
| pUC | 10 |

Figure 1B:
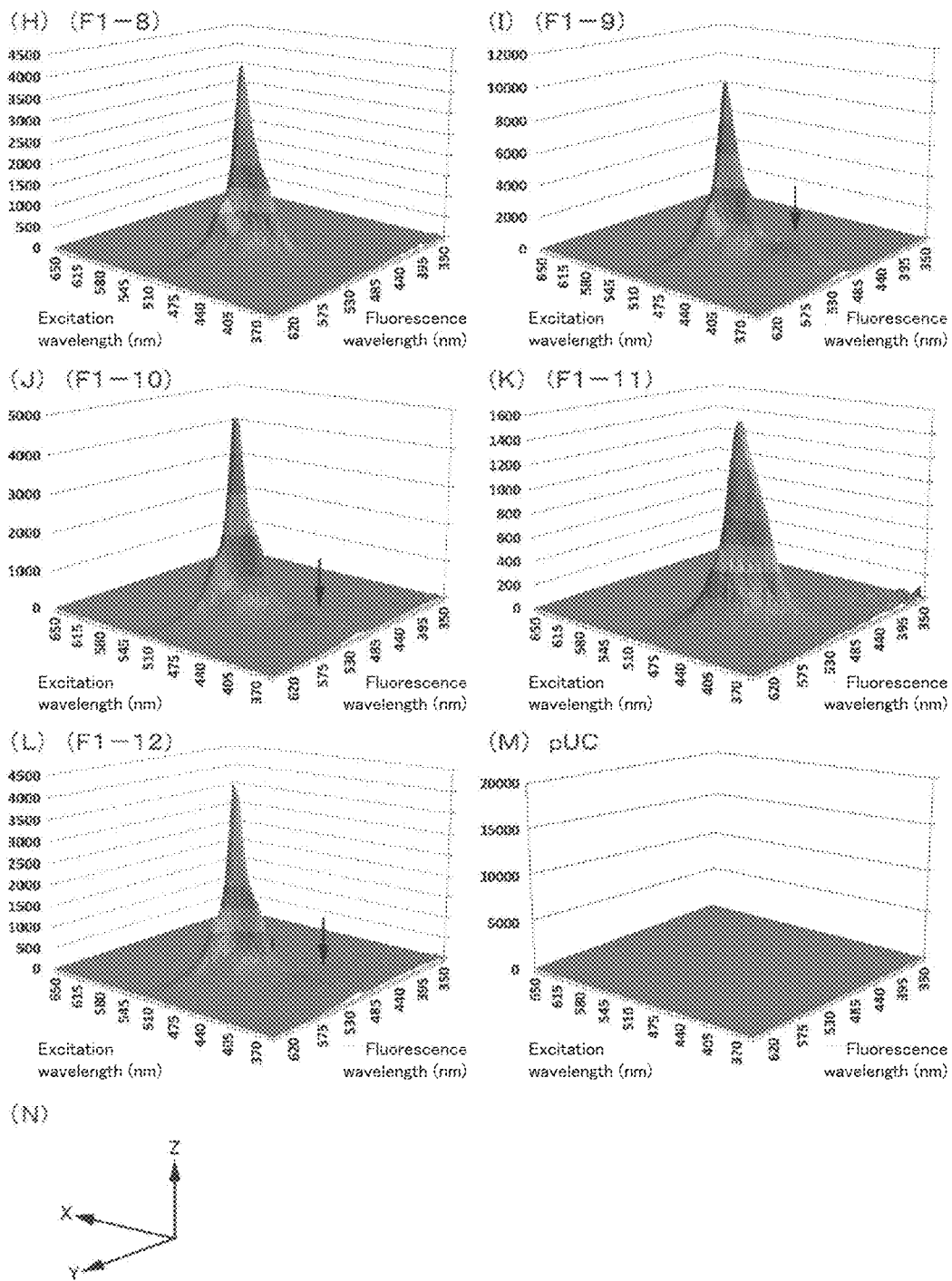
FIG. 1B shows graphs showing the fluorescence intensities at different excitation wavelengths and fluorescence wavelengths in Example 1.

The measurement results of the overall range of the excitation wavelength and the overall range of the fluorescence wavelength are shown in FIGS. 1A and 1B. FIGS. 1A and 1B each show graphs showing the fluorescence intensities at different excitation wavelengths and fluorescence wavelengths in Example 1. In FIG. 1A, (A) to (G) show the results of the proteins (F1-1) to (F1-7), respectively. In FIG. 1B, (H) to (L) show the results of the proteins (F1-8) to (F1-12), respectively, (M) shows the result of the negative control (pUC), and (N) shows the details of the axes in each graph. As shown in (N) of FIG. 1B, in (A) to (G) of FIG. 1A and (H) to (N) of FIG. 1B, the X-axis direction shows the excitation wavelength, the Y-axis direction shows fluorescence wavelength, and the Z-axis direction shows the fluorescence intensity. As shown in (A) to (L) of FIGS. 1A and 1B, the proteins (F1-1) to (F1-12) each showed a fluorescence activity. In contrast, as shown in (M) of FIG. 1B, the negative control did not show a fluorescence activity. As shown in (B) of FIG. 1A, the protein (F1-2) showed a stronger fluorescence activity than other proteins under excitation with excitation light at the same intensity.

As shown by the arrows (A), (C), and (F) of FIG. 1A and (I), (J), and (L) of FIG. 1B, the proteins (F1-1), (F1-3), (F1-6), (F1-9), (F1-10), and (F1-12) each showed a stronger fluorescence activity than other proteins at a relatively low excitation wavelength (350 to 435 nm). Specifically, the proteins (F1-1), (F1-3), (F1-6), (F1-9), (F1-10), and (F1-12) each showed a fluorescence at around 520 nm even under excitation with excitation light having a excitation wavelength described in the following table 7. The excitation maximum wavelength shown in table 7 is an excitation wavelength, within the excitation wavelength of 350 to 435 nm, which shows the maximum fluorescence intensity.

TABLE 7

| | Excitation wavelength | Excitation maximum wavelength |
|---|---|---|
| F1-1 | 350~435 nm | 396~404 nm |
| F1-3 | 350~435 nm | 396~404 nm |
| F1-6 | 350~435 nm | 391~399 nm |
| F1-9 | 350~435 nm | 401~409 nm |
| F1-10 | 350~435 nm | 391~399 nm |
| F1-12 | 350~435 nm | 386~394 nm |

These results showed that the novel fluorescent protein of the present invention has a fluorescence activity.

Example 2

It was examined that the novel fluorescent protein can be screened by the screening method of the present invention.
(1) Construction of Expression Vector A mutation polynucleotide was produced by a DNA shuffling method and the mutation polynucleotide was linked to the vector, thereby constructing the expression vector of the mutation polynucleotide. Specifically, the expression vector was constructed as follows. First, the polynucleotide (f1-3) (SEQ ID NO: 17) and the polynucleotide (f1-15) (SEQ ID NO: 29) were amplified by the 1st polymerase chain reaction (PCR) using the following primer set, thereby obtaining a 1st PCR product. The PCR reaction solution was prepared using the kit TaKaRa EX Taq® (product of TAKARA BIO INC.) according to the instruction.

Primer Set

```
Primer sequence 1
                                        (SEQ ID NO: 102)
5'-ATGCTTCCGGCTCGTATGTTG-3'

Primer sequence 2
                                        (SEQ ID NO: 103)
5'-GTACGGCCGACTAGTAGGCC-3'
```

1.9 μg of the 1st PCR product was suspended in a buffer solution containing deoxyribonuclease (DNase) and having the following composition, caused to react at 25° C. for 20 minutes, and then caused to react at 90° C. for 10 minutes, thereby fragmenting DNA.

[Composition of Buffer Solution]

| Total | 40 μL |
|---|---|
| DNase I | (product of TaKaRa) |
| 0.05 U | (PCR product of polynucleotide (f1-3)) |
| 0.025 U | (PCR product of polynucleotide (f1-15)) |
| Tris-Hcl | 50 mmol/L |
| MnCl$_2$ | 10 mmol/L | pH 7.4

Each of the fragmented DNAs was purified by agarose gel electrophoresis and gel extraction. Then, the obtained purified product was added to the PCR reaction solution so that the concentration of the solution is in the range from 10 to 30 μg/μL and the resultant was amplified by the 2nd PCR, thereby obtaining a number of 2nd PCR products. In the 2nd PCR, the above-described primer set was not used. Then, one-fiftieth of each of the 2nd PCR products was added to the PCR reaction solution and amplified by the 3rd PCR using the primer set, thereby obtaining a mutation polynucleotide. The mutation polynucleotide was cleaved by the restriction enzymes and each of the resultants was linked to the pEGFP vector cleaved by the restriction enzymes. The vector into which the mutation polynucleotide was inserted was served as a mutation polynucleotide expression vector. In this manner, a number of mutation polynucleotide expression vectors were obtained.

(2) Transfection to *Escherichia coli*

Each of the mutation polynucleotide expression vectors alone was transfected to the *Escherichia coli* JM109 strain by a heat shock method. The obtained transformant was cultured at 37° C. overnight (18 hours) until about 1000 colonies are formed using an LB culture medium containing 100 μg/mL antibiotic (ampicillin).

(3) Examination of Fluorescence Activity

Then, each of the cultured bacterial cells was collected and the fluorescence activity of the bacterial cell was examined using the LEDUV light source (NS375LIM, product of Nitride Semiconductors Co., Ltd.) as a light source and the UL360 (OMG CO., LTD.) as a filter. As to the bacterial cell whose fluorescence activity was observed, the plasmid was purified, the procedures (1) and (2) of Example 2 were repeated three times, and then the fluorescence activity of the bacterial cell was examined in the same manner as described above.

(4) Sequence of *Escherichia coli*

The colony of the bacterial cell whose fluorescence activity was observed in the examination (3) was recovered, the plasmid was purified, and the resultant was subjected to a direct sequencing under the following conditions. The results showed that the bacterial cell whose fluorescence activity was observed includes one of the novel genes of the present invention (SEQ ID NOs: 68 to 101). These results showed that the novel fluorescent protein of the present invention can be screened by the screening method of the present invention.

[Conditions of Direct Sequencing]

```
Sequencer          ABI 3130xl (product of Applied Biosys-
                   tems)

Sequencing reagent BigDye Terminator V1-1 cycle sequencing
                   kit (product of Applied Biosystem)

Sequencing primer
Primer sequence 1
                                                 (SEQ ID NO: 102)
5'-ATGCTTCCGGCTCGTATGTTG-3'

Primer sequence 2
                                                 (SEQ ID NO: 103)
5'-GTACGGCCGACTAGTAGGCC-3'
```

Example 3

The fluorescence activity of the novel protein of the present invention was examined. The experimental conditions, experimental method, and the like were the same as those described in Example 1 unless otherwise noted.

(1) Construction of Expression Vector

Fourteen kinds of vector insertion sequences were obtained by a chemical synthesis by adding the 5' end sequence (5'-AAGCTTG-3') to the 5' end of and the 3' end sequence (5'-AATTC-3') to the 3' end of each of the base sequences of the novel genes (SEQ ID NOs: 68 to 82, (f1-19) to (f1-33)) encoding the novel fluorescent proteins (SEQ ID NOs: 34 to 48). Also, nineteen kinds of vector insertion sequences were obtained by a chemical synthesis by adding the 5' end sequence (5'-AAGCTTG-3') to the 5' end of and the 3' end sequence (5'-AATTC-3') to the 3' end of each of the base sequences of the novel genes (SEQ ID NOs: 83 to 101, (f1-34) to (f1-52)) encoding the novel fluorescent proteins (SEQ ID NOs: 49 to 67). The vector insertion sequences including the novel genes (f1-19) to (f1-52) were referred to as the vector insertion sequences (f1-19) to (f1-52), respectively.

The vector insertion sequences (f1-19) to (f1-52) each were cleaved by the restriction enzymes and each of the resultants was linked to the pEGFP vector cleaved by the restriction enzymes. The vectors into which the vector insertion sequences (f1-19) to (f1-52) were inserted were referred to as the expression vectors (f1-19) to (f1-52), respectively.

(2) Transfection to *Escherichia coli*

Each of the expression vectors (f1-19) to (f1-52) was transfected to the *Escherichia coli* DH5α strain, the supernatant obtained from each of the transformants to which the expression vectors (f1-19) to (f1-52) have transfected were referred to as proteins (F1-13) to (F1-46), and the concentration of the protein in each supernatant was determined by measuring the absorbance in the same manner as in the transfection (2) of Example 1 except for the following experimental conditions. As to the experimental condition, the culture time of the transformant was 16 to 18 hours and the PBS solution in which the pellet after washing is suspended was 1.5 mL. Each of the obtained suspensions was sonicated four times with Amp 35% at 10 seconds/30 seconds, for 2 minutes using the ultrasonic homogenizer. Each of the sonicated suspension was centrifuged with 3000 rpm at 4° C. for 10 minutes. The concentration of the protein in each supernatant was determined by measuring the absorbance at 562 nm by a microplate reader.

(3) Measurement of Fluorescence Activity

Each supernatant obtained in the transfection (2) was diluted based on the concentration of the protein in each supernatant measured in the transfection (2) so that the concentration of the protein in the supernatant was in the range from 1.5 to 2.0 mg/mL. A to 50 to 70 μL of each supernatant after dilution, the fluorescence intensity (FI) was measured with the microplate reader under the same measurement conditions as in the measurement (3) of Example 1. As a control, the fluorescence intensity (FI) was measured in the same manner as described above except that the expression vectors (f1-3) and (f1-15) were transfected instead of the expression vector and the proteins (F1-1) and (F1-9) were obtained.

The results of the proteins (F1-13) to (F1-27), (F1-1), and (F1-9) are shown in the following table 8A, the results of the proteins (F1-28) to (F1-46), (F1-1), and (F1-9) are shown in the following table 8B, and the results of the proteins (F1-28) to (F1-46) and (F1-9) are shown in the following table 8C. The tables 8A to 8C shows the values of the excitation wavelength (Ex), fluorescence wavelength, and fluorescence intensity (FI) of each protein. As shown in the table 8A, the proteins (F1-13) to (F1-27) each showed a stronger fluorescence activity than the proteins (F1-1) and (F1-9). Particularly, the proteins (F1-14) to (F1-27) each showed a significantly strong fluorescence activity. As shown in the table 8B, the proteins (F1-28) to (F1-46) each showed a stronger fluorescence activity than the proteins (F1-1) and (F1-9). As shown in the table 8C, the proteins (F1-28) to (F1-46) each showed a stronger fluorescence activity than the protein (F1-9). These results showed that the novel fluorescent protein of the present invention has a fluorescence activity.

TABLE 8A

| | Excitation wavelength (nm) | Fluorescence wavelength (nm) | Fluorescence intensity (FI) |
|---|---|---|---|
| F 1-13 | 400 | 515 | 20039 |
| F 1-14 | 405 | 515 | 55699 |
| F 1-15 | 400 | 515 | 67637 |
| F 1-16 | 395 | 515 | 60605 |
| F 1-17 | 400 | 515 | 73516 |
| F 1-18 | 400 | 515 | 76394 |
| F 1-19 | 400 | 515 | 72697 |
| F 1-20 | 395 | 515 | 59493 |
| F 1-21 | 395 | 515 | 67541 |
| F 1-22 | 400 | 515 | 60683 |
| F 1-23 | 395 | 515 | 62924 |
| F 1-24 | 400 | 515 | 76883 |
| F 1-25 | 400 | 515 | 62724 |
| F 1-26 | 400 | 515 | 67142 |
| F 1-27 | 395 | 515 | 71671 |
| F 1-1 | 400 | 515 | 5925 |
| F 1-9 | 405 | 515 | 4362 |

TABLE 8B

| | Excitation wavelength (nm) | Fluorescence wavelength (nm) | Fluorescence intensity (FI) |
|---|---|---|---|
| F 1-28 | 405 | 515 | 8554 |
| F 1-29 | 405 | 515 | 16151 |
| F 1-30 | 405 | 515 | 16475 |
| F 1-31 | 405 | 515 | 11240 |
| F 1-32 | 405 | 515 | 7507 |
| F 1-33 | 405 | 515 | 8862 |
| F 1-34 | 405 | 515 | 18209 |
| F 1-35 | 410 | 515 | 8404 |
| F 1-36 | 405 | 515 | 19190 |
| F 1-37 | 405 | 515 | 10031 |
| F 1-38 | 405 | 515 | 18823 |
| F 1-39 | 420 | 515 | 19742 |
| F 1-40 | 405 | 515 | 14866 |
| F 1-41 | 405 | 515 | 10860 |
| F 1-42 | 420 | 515 | 22967 |
| F 1-43 | 425 | 515 | 9600 |
| F 1-44 | 405 | 515 | 13029 |
| F 1-45 | 405 | 515 | 8516 |
| F 1-46 | 405 | 515 | 12651 |
| F 1-1 | 400 | 515 | 3850 |
| F 1-9 | 405 | 515 | 3063 |

TABLE 8C

| | Excitation wavelength (nm) | Fluorescence wavelength (nm) | Fluorescence intensity (FI) |
|---|---|---|---|
| F 1-28 | 500 | 515 | 53757 |
| F 1-29 | 500 | 515 | 114174 |
| F 1-30 | 500 | 515 | 106071 |
| F 1-31 | 500 | 515 | 72273 |
| F 1-32 | 500 | 515 | 48253 |
| F 1-33 | 500 | 515 | 55930 |
| F 1-34 | 500 | 515 | 113810 |
| F 1-35 | 500 | 515 | 53349 |
| F 1-36 | 505 | 515 | 118062 |
| F 1-37 | 500 | 515 | 63908 |
| F 1-38 | 500 | 515 | 108094 |
| F 1-39 | 500 | 515 | 122494 |
| F 1-40 | 500 | 515 | 90253 |
| F 1-41 | 500 | 515 | 66769 |
| F 1-42 | 500 | 515 | 136002 |
| F 1-43 | 505 | 515 | 68784 |
| F 1-44 | 500 | 515 | 80642 |
| F 1-45 | 500 | 515 | 50212 |
| F 1-46 | 500 | 515 | 78833 |
| F 1-9 | 505 | 515 | 16702 |

Figure 2A:
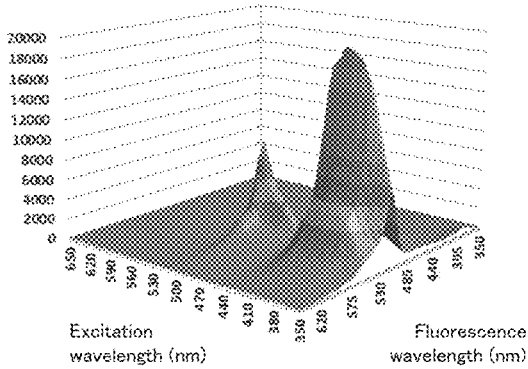
FIG. 2A shows graphs showing the fluorescence intensities at different excitation wavelengths and fluorescence wavelengths in Example 3.
Figure 2A:
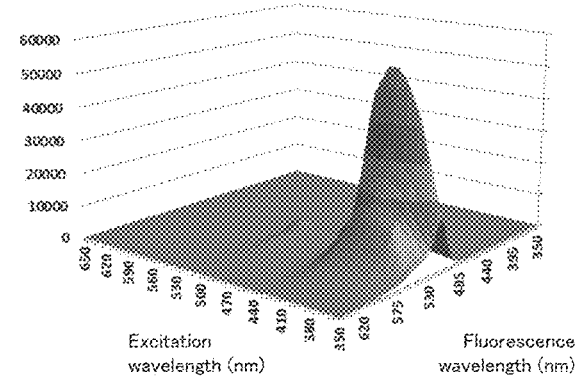
Figure 2A:
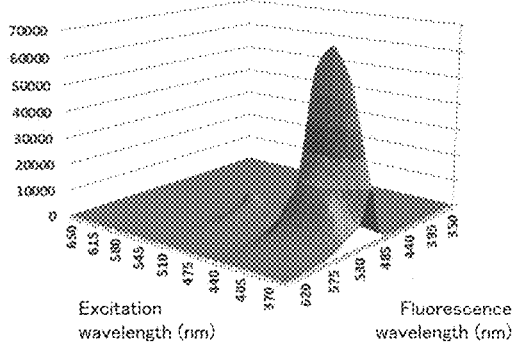
Figure 2A:
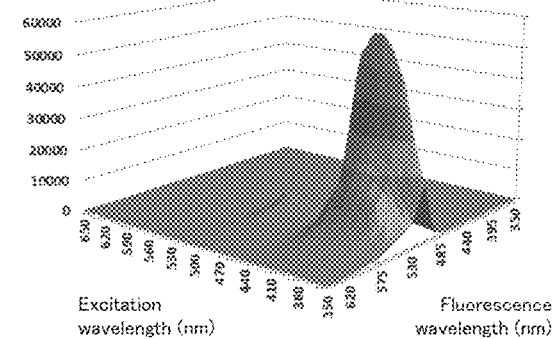
Figure 2A:
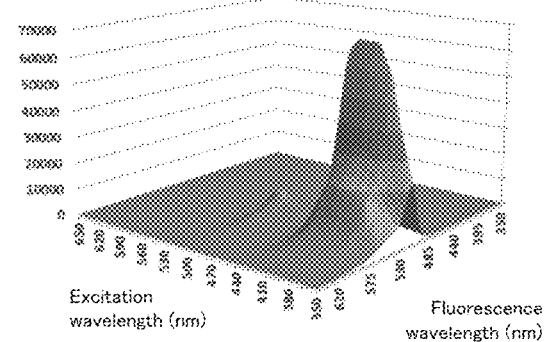
Figure 2A:
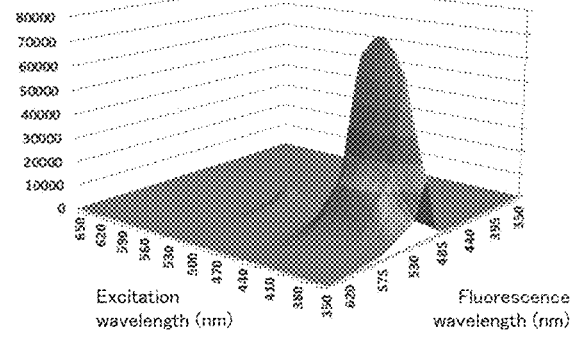
Figure 2B:
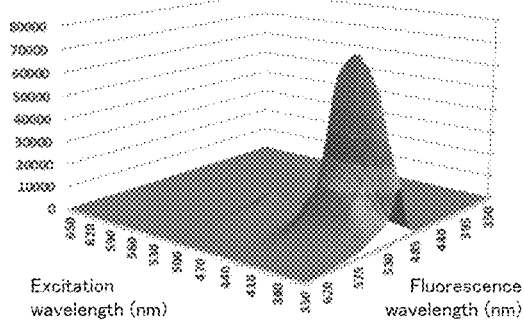
FIG. 2B shows graphs showing the fluorescence intensities at different excitation wavelengths and fluorescence wavelengths in Example 3.
Figure 2B:
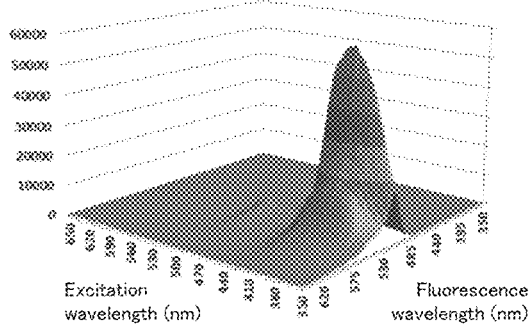
Figure 2B:
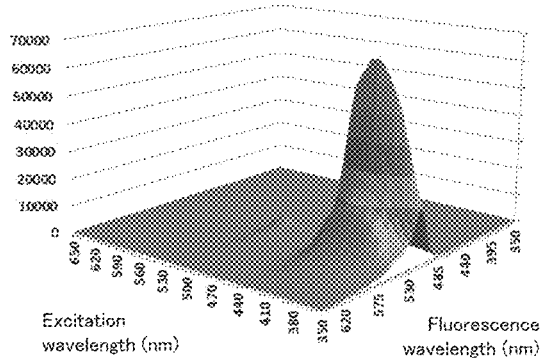
Figure 2B:
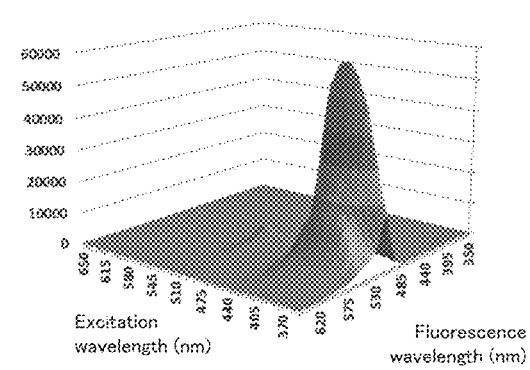
Figure 2B:
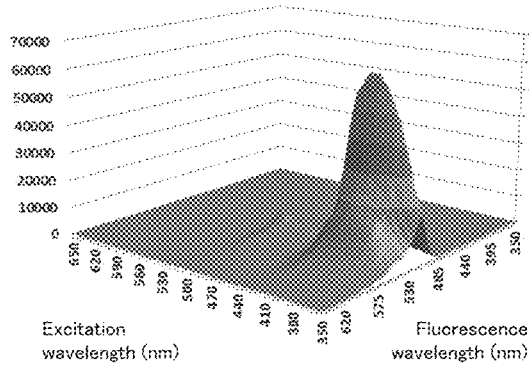
Figure 2B:
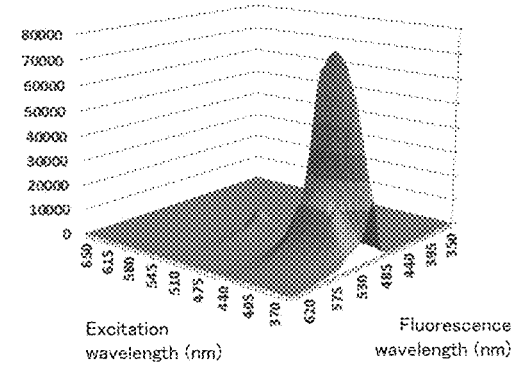
Figure 2C:
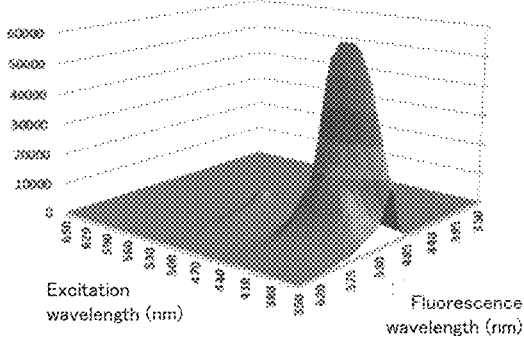
FIG. 2C shows graphs showing the fluorescence intensities at different excitation wavelengths and fluorescence wavelengths in Example 3.
Figure 2C:
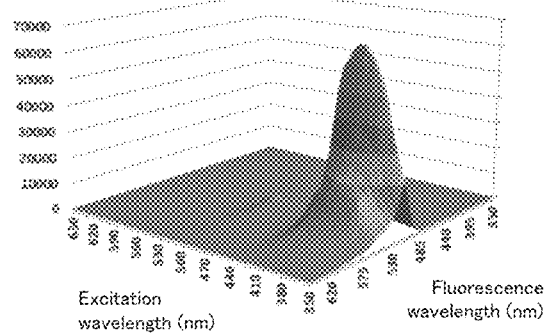
Figure 2C:
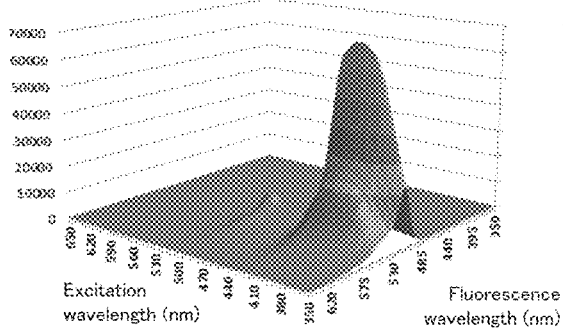
Figure 2C:
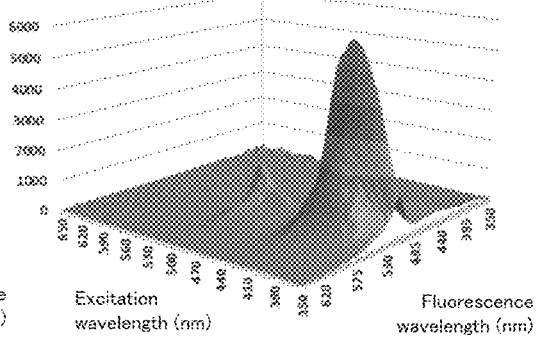
Figure 2C:
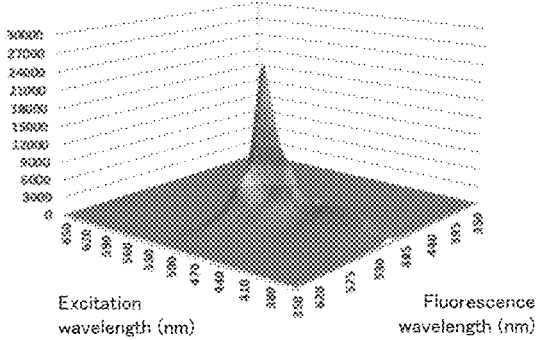
Figure 3A:
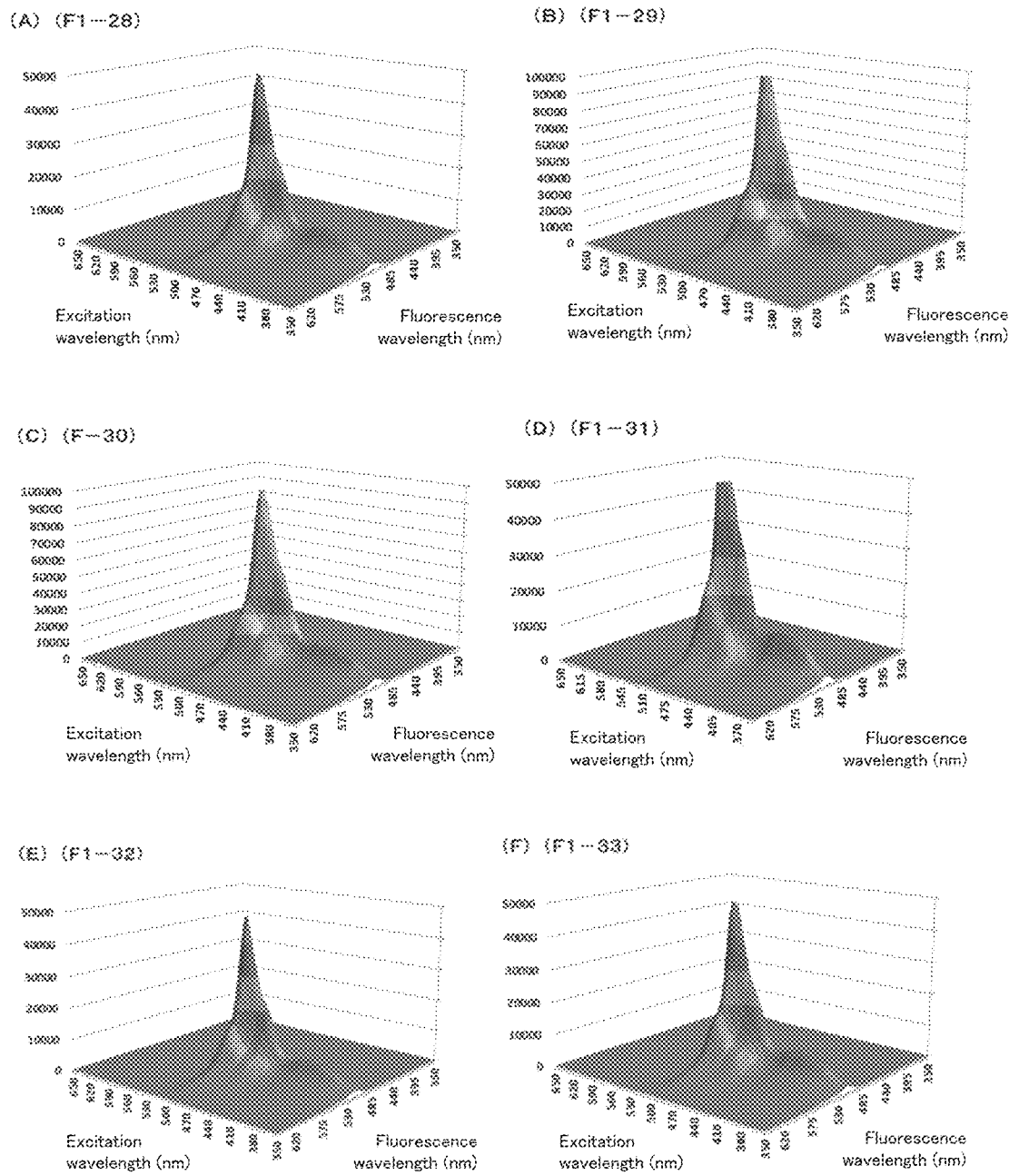
FIG. 3A shows graphs showing the fluorescence intensities at different excitation wavelengths and fluorescence wavelengths in Example 3.
Figure 3B:
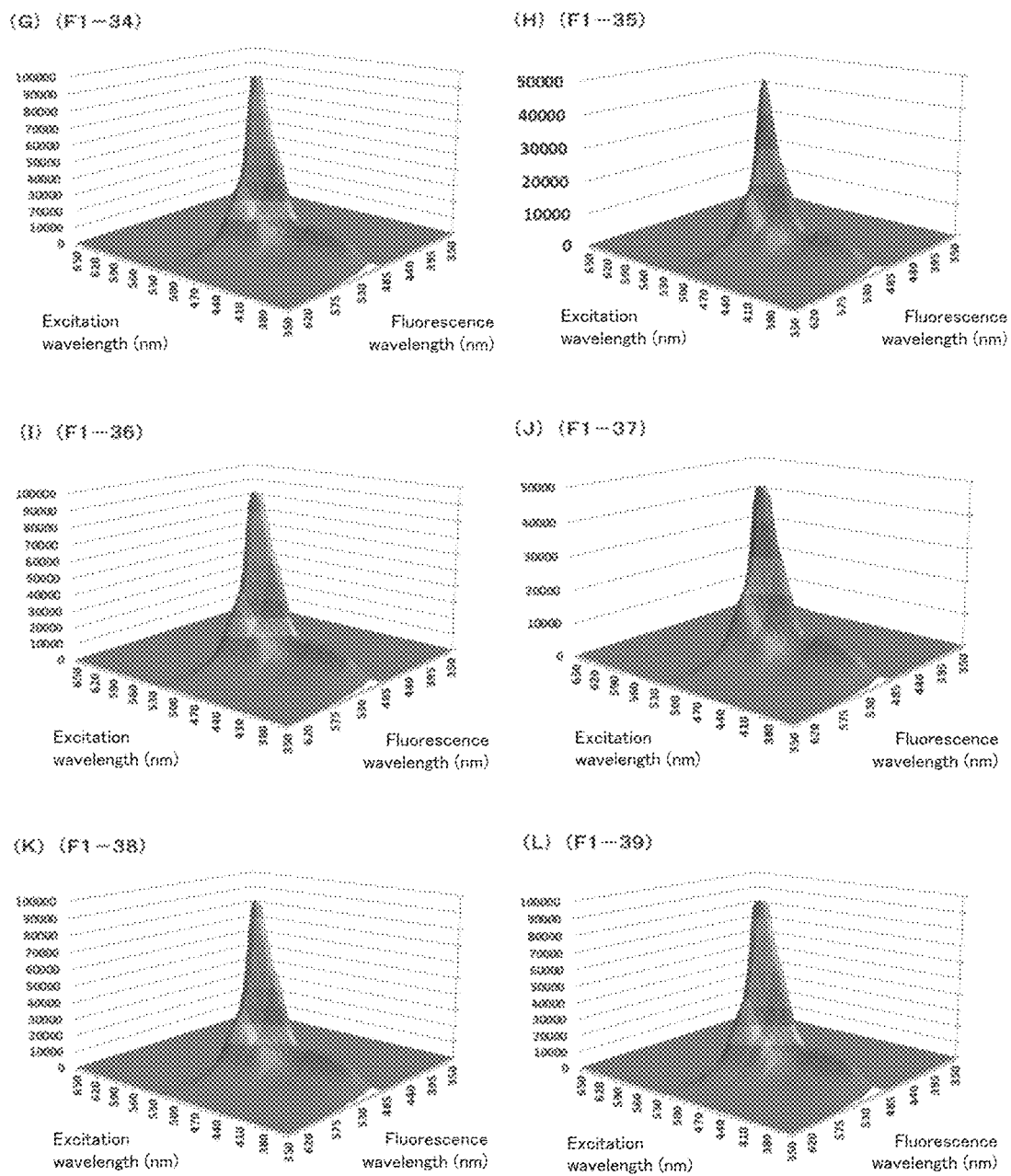
FIG. 3B shows graphs showing the fluorescence intensities at different excitation wavelengths and fluorescence wavelengths in Example 3.
Figure 3C:
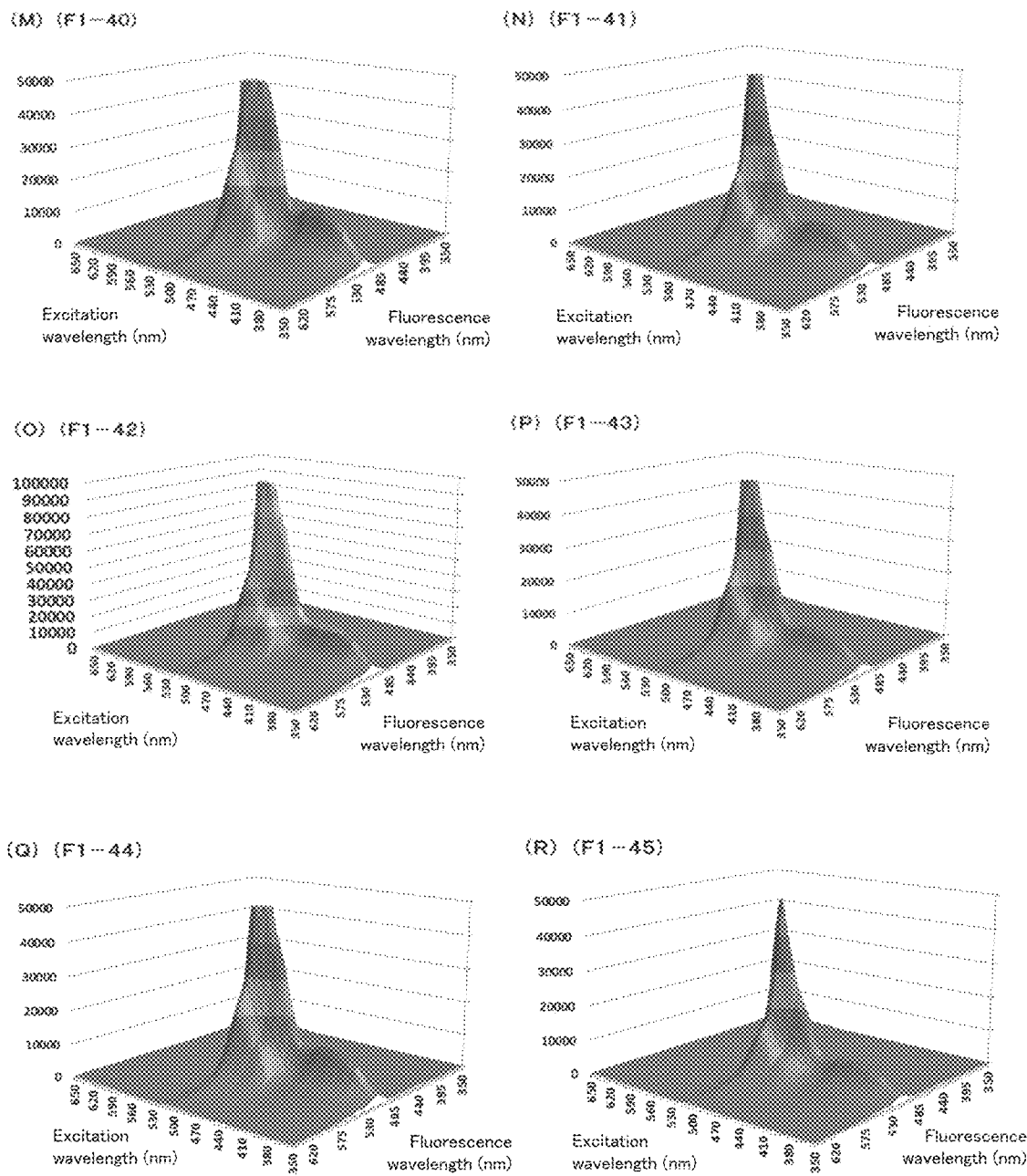
FIG. 3C shows graphs showing the fluorescence intensities at different excitation wavelengths and fluorescence wavelengths in Example 3.
Figure 3D:
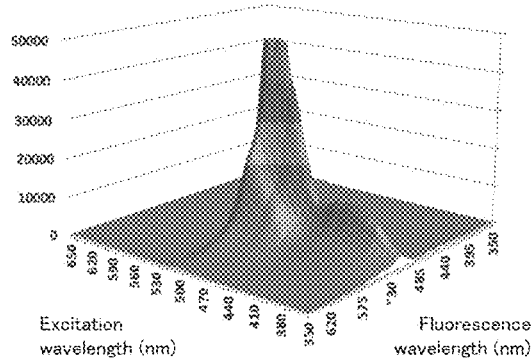
FIG. 3D shows graphs showing the fluorescence intensities at different excitation wavelengths and fluorescence wavelengths in Example 3.
Figure 3D:
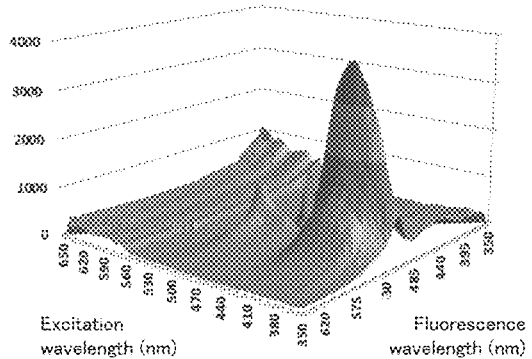
Figure 3D:
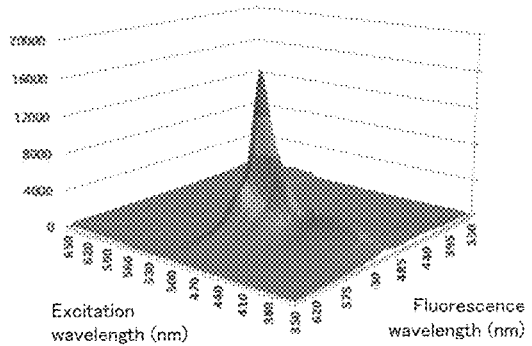

The measurement results of the overall range of the excitation wavelength and the overall range of the fluorescence wavelength are shown in FIGS. 2A to 3D. FIGS. 2A to 3D each show graphs showing the fluorescence intensities at different excitation wavelengths and fluorescence wavelengths in Example 3. In FIG. 2A, (A) to (F) show the results of the proteins (F1-13) to (F1-18), respectively. In FIG. 2B, (G) to (L) show the results of the proteins (F1-19) to (F1-24), respectively. In FIG. 2C, (M) to (Q) show the results of the proteins (F1-25) to (F1-27), (F1-1), and (F1-9), respectively. In FIG. 3A, (A) to (F) show the results of the proteins (F1-28) to (F1-33), respectively. In FIG. 3B, (G) to (L) show the results of the proteins (F1-34) to (F1-39), respectively. In FIG. 3C, (M) to (R) show the results of the proteins (F1-40) to (F1-45), respectively. In FIG. 3D, (S) to (U) show the results of the proteins (F1-46), (F1-1), and (F1-9), respectively. As shown in (N) of FIG. 1B, in (A) to (Q) of FIGS. 2A to 2C and (A) to (U) of FIGS. 3A to 3D, the X-axis direction shows the excitation wavelength, the Y-axis direction shows fluorescence wavelength, and the Z-axis direction shows the fluorescence intensity. As shown in (A) to (O) of FIGS. 2A to 2C and (A) to (S) of FIGS. 3A to D, the proteins (F1-13) to (F1-27) and (F1-28) to (F1-46) each showed a stronger fluorescence activity than the proteins (F1-1) and (F1-9). Particularly, as shown in (B) to (O) of FIGS. 2A to 2C, the proteins (F1-14) to (F1-27) showed a significantly strong fluorescence activity. These results showed that the novel fluorescent protein of the present invention has a fluorescence activity.

Example 4

The fluorescence activity of the novel protein of the present invention was examined. The experimental condition, experimental method, and the like were the same as those described in Example 1 unless otherwise noted.

The supernatants of the proteins (F1-1), (F1-2), (F1-9), (F1-27), and (F1-42) were obtained in the same manner as in Example 1 except that a tag (6×His tag) consisting of histidine 6 residues was added to the N end of each protein. The supernatants were subjected to protein purification according to the instruction manual of TALON Superflow Metal Affinity Rsesin (product of TAKARA BIO INC.), and the eluates containing the proteins (F1-1), (F1-2), (F1-9), (F1-27), and (F1-42), respectively, were obtained. Each eluate was diluted so that the concentration of the protein was 0.2 mg/mL. As to 50 µL of each supernatant after elution, the fluorescence intensity (FI) was measured with the microplate reader under the following measurement conditions.

(Measurement Conditions)
Excitation wavelength: 505 to 520 nm (band width: 1 nm)
Fluorescence (detection) wavelength: 350 to 525 nm (band width: 1 nm)
Laser intensity (Gain): 105

The results of the proteins (F1-1), (F1-9), (F1-27), and (F1-42) in the case where the excitation wavelength (Ex) was around 400 nm and the fluorescence wavelength (Em) was around 515 nm are shown in the following table 9A and the results of the proteins (F1-2), (F1-9), and (F1-42) in the case where the excitation wavelength (Ex) was 507 nm and the fluorescence wavelength (Em) was around 515 nm are shown in the following table 9B. As shown in the table 9A, the proteins (F1-27) and (F1-42) each showed a stronger fluorescence activity than the proteins (F1-1) and (F1-9). Particularly, the protein (F1-27) showed a significantly strong fluorescence activity. As shown in the table 9B, the proteins (F1-2) and (F1-42) each showed a stronger fluorescence activity than the protein (F1-9). These results showed that the novel fluorescent protein of the present invention has a fluorescence activity.

TABLE 9A

| | Excitation wavelength (nm) | Fluorescence wavelength (nm) | Fluorescence intensity (FI) |
| --- | --- | --- | --- |
| F1-1 | 400 | 512 | 4294 |
| F1-9 | 409 | 513 | 4209 |
| F1-27 | 400 | 512 | 37747 |
| F1-42 | 403 | 513 | 16025 |

TABLE 9B

| | Excitation wavelength (nm) | Fluorescence wavelength (nm) | Fluorescence intensity (FI) |
| --- | --- | --- | --- |
| F1-2 | 507 | 516 | 287170 |
| F1-9 | 507 | 513 | 34757 |
| F1-42 | 507 | 513 | 107742 |

Figure 4:
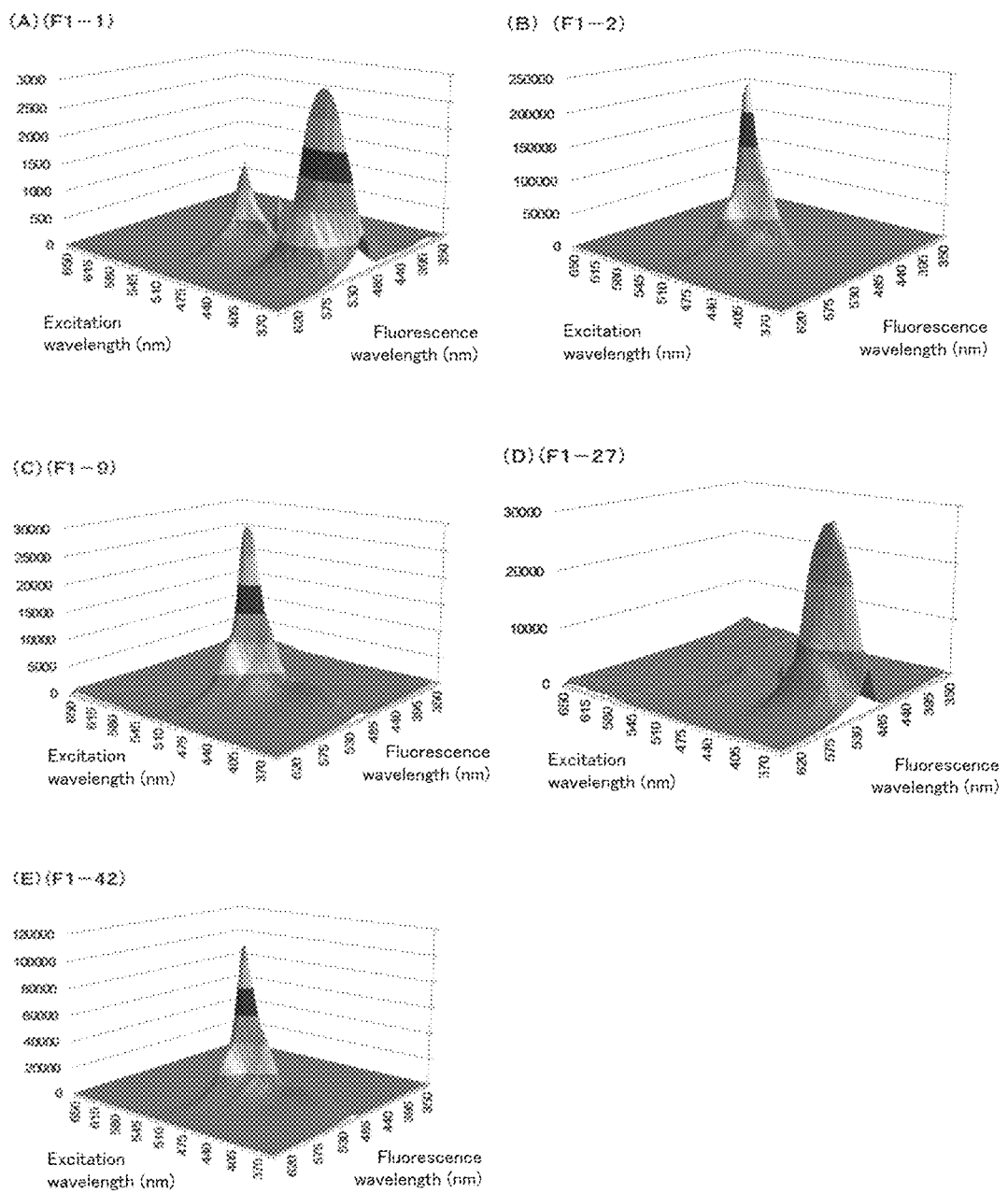
FIG. 4 shows graphs showing the fluorescence intensities at different excitation wavelengths and fluorescence wavelengths in Example 4.

The measurement results of the overall range of the excitation wavelength and the overall range of the fluorescence wavelength are shown in FIG. 4. FIG. 4 shows graphs showing the fluorescence intensities at different excitation wavelengths and fluorescence wavelengths in Example 4. In FIG. 4, (A) to (E) show the results of the proteins (F1-1), (F1-2), (F1-9), (F1-27), and (F1-42). As shown in (N) of FIG. 1B, in (A) to (E) of FIG. 4, the X-axis direction shows the excitation wavelength, the Y-axis direction shows fluorescence wavelength, and the Z-axis direction shows the fluorescence intensity. As shown in FIG. 4, the proteins (F1-1), (F1-2), (F1-9), (F1-27), and (F1-42) each showed a fluorescence activity. The proteins (F1-1), (F1-27), and (F1-42) showed a stronger fluorescence activity even at a relatively low excitation wavelength (around 400 nm). Particularly the protein (F1-27) showed a significantly strong fluorescence activity. These results showed that the novel fluorescent protein of the present invention has a fluorescence activity.

Example 5

The fluorescence activity of the novel protein of the present invention was examined. The experimental conditions, experimental method, and the like were the same as those described in Example 1 unless otherwise noted.

(1) Construction of Expression Vector

The vector insertion sequences (SEQ ID NOs: 104, 105, and 106) each having a sequence in which a His tag sequence was added to the N end of each of the novel genes (SEQ ID NOs: 18, 82, and 97) encoding the novel fluorescent proteins (SEQ ID NOs: 3, 48, and 63), respectively, were obtained by a chemical synthesis. In the vector insertion sequence, the underlined base sequence within parentheses is a base sequence corresponding to the novel gene encoding the novel fluorescent protein and the underlined base sequence outside the parentheses corresponds to a His tag sequence. The relationships between the boxed $N_{592}N_{593}N_{594}$ codon and $N_{613}N_{614}N_{615}$ codon and the novel fluorescent protein and the novel gene in the vector insertion sequence are shown in the following table 10. The vector insertion sequences in each of which the $N_{592}N_{593}N_{594}$ codon and the $N_{613}N_{614}N_{615}$ codon were one of (f1-4), (f1-33), and (f1-48) were referred to as the vector insertion sequences (f1-4), (f1-33), and (f1-48), respectively.

Vector insertions sequence
(SEQ ID NO: 104)
5'-TCTAGATGCATCATCATCATCATCATGGCGGCAGC[ATGACAACCTT

CAAAATCGAGTCCCGGATCCATGGCAACCTCAACGGGGAGAAGTTCGAGT

TGGTTGGAGGTGGAGTAGGTGAGGAGGGTCGCCTCGAGATTGAGATGAAG

ACTAAAGATAAACCACTGGCATTCTCTCCCTTCCTGCTGTCCCACTGCAT

GGGTTACGGGTTCTACCACTTCGCCAGCTTCCCAAAGGGGACTAAGAACA

TCTATCTTCATGCTGCAACAAACGGAGGTTACACCAACACCAGGAAGGAG

ATCTATGAAGACGGCGGCATCTTGGAGGTCAACTTCCGTTACACTTACGA

GTTCAACAAGATCATCGGTGACGTCGAGTGCATTGGACATGGATTCCCAA

GTCAGAGTCCGATCTTCAAGGACACGATCGTGAAGACTTGTCCCACGGTG

GACCTGATGTTGCCGATGTCCGGGAACATCATCGCCAGCTCCTACGCTAA

GGCCTTCCAACTGAAGGACGGCTCTTTCTACACGGCAGAAGTCAAGAACA

ACATAGACTTCAAGAATCCAATCCACGAGTCCTTCTCGAAGTCGGGGCCC

ATGTTCACCCACAGACGTGTCGAGGAGACT[CAC]ACCAAGGAGAACCTTGC

[ATG]GTGGAGTACCAGCAGGTTTTCAACAGCGCCCCAAGAGACATGTAG]

AATTCTGCAGATATCCAGCACAGTGGCGAAGCTT-3'

Vector insertions sequence
(SEQ ID NO: 105)
5'-TCTAGATGCATCATCATCATCATCATGGCGGCAGC[ATGACAACCTT

CAAAATCGAGTCCCGGATCCACGGCAACCTCAACGGGGAGAAGTTCGAGT

TGGTTGGAGGTGGAGTAGGTGAGGAGGGTCGCCTCGAGATTGAGATGAAG

ACTAAAGATAAACCACTGGCATTCTCTCCCTTCCTGCTGACCACTTGCAT

GGGTTACGGGTTCTACCACTTCGCCAGCTTCCCAAAGGGGATTAAGAACA

TCTATCTTCATGCTGCAACGAACGGAGGTTACACCAACACCAGGAAGGAG

ATCTATGAAGACGGCGGCATCTTGGAGGTCAACTTCCGTTACACTTACGA

GTTCAACAAGATCATCGGTGACGTCGAGTGCATTGGACATGGATTCCCAA

GTCAGAGTCCGATCTTCAAGGACACGATCGTGAAGAGTTGTCCCACGGTG

-continued

```
GACCTGATGTTGCCAATGTCCGGGAACATCATCGCCAGCTCCTACGCTTA

CGCCTTCCAACTGAAGGACGGCTCTTTCTACACGGCAGAAGTCAAGAACA

ACATAGACTTCAAGAATCCAATCCACGAGTCCTTCTCGAAGTCAGGGCCC

ATGTTCACCCACAGACGTGTCGAGGAGACT[CTC]ACCAAGGAGAACCTTGC

C[ATA]GTGGAGTACCAGCAGGTTTTCAACAGCGCCCCAAGAGACATGTAG]

AATTCTGCAGATATCCAGCACAGTGGCGAAGCTT-3'
```

Vector insertions sequence (SEQ ID NO: 106)
```
5'-TCTAGATGCATCATCATCATCATCATGGCGGCAGC[ATGACAACCTT

CAAAATCGAGTCCCGGATCCACGGCAACCTCAACGGGGAGAAGTTCGAGT

TGGTTGGAGGTGGAGTAGGTGAGGAGGGTCGCCTCGAGATTGAGATGAAG

ACTAAAGATAAACCACTGGCATTCTCTCCCTTCCTGCTGTCCTGCTGCAT

GGGTTACGGGTTCTACCACTTCGCCAGCTTCCCAAAGGGGACTGAGAACA

TCTATCTTCATGCTGCAACAAACGGAGGTTACACCAACACCAGGAAGGAG

ATCTATGAAGACGGCGGCATCTTGGAGGTCAACTTCCGTTACACTTACGA

GTTCAACAAGATCATCGGTGACGTCGAGTGCATTGGACATGGATTCCCAA

GTCAGAGTCCGATCTTCAAGGACACGATCGTGAAGCAATGGCCCACGGTG

GACCTGATGTTGCCGATGTCCGGGAACATCATCGCCAGTTCCTACGCTTT

GGCCTTCCAACTGAAGGACGGCTCTTTCTACACGGCAGAGGTCAAGAACA

ACATAGACTTCAAGAATCCAATCCACGAGTCCTTCTCGAAGTCGGGGCCC

ATGTTCACCCACAGACGTGTCGAGGAGACT[CAC]ACCAAGGAGAACCTTGC

C[ATA]GTGGAGTACCAGCAGGTTTTCAACAGCGCCCCAAGAGACATGTAG]

AATTCTGCAGATATCCAGCACAGTGGCGAAGCTT-3'
```

TABLE 10

| | $N_{592}N_{593}N_{594}$ | $N_{613}N_{614}N_{615}$ | Protein | Gene |
|---|---|---|---|---|
| (f1-4) | CAC | ATG | SEQ ID NO: 3 | SEQ ID NO: 18 |
| (f1-33) | CTC | ATA | SEQ ID NO: 48 | SEQ ID NO: 82 |
| (f1-48) | CAC | ATA | SEQ ID NO: 63 | SEQ ID NO: 97 |

The vector insertion sequences (f1-4), (f1-33), and (f1-48) each were cleaved by restriction enzymes HindIII and XbaI and each of the resultants was linked to the pcDNA3.1-hygro(−) vector (product of Invitrogen Corporation) cleaved by the restriction enzymes. The vectors into which the vector insertion sequences (f1-4), (f1-33), and (f1-48) were inserted were referred to as the expression vectors (f1-4), (f1-33), and (f1-48), respectively.

(2) Amplification and Purification of Plasmid DNA

Each of the expression vectors (f1-4), (f1-33), and (f1-48) was transfected to the *Escherichia coli* DH5α strain in the same manner as in the transfection (2) of Example 1 and the *Escherichia coli* was cultured at 37° C. under 5% $CO_2$ for 10 hours, thereby amplifying the plasmid DNAs containing the genes (f1-4), (f1-33), and (f1-48). Then, the plasmid DNAs containing the genes (f1-4), (f1-33), and (f1-48) were purified with the Midi Prep Kit (product of QIAGEN) according to the protocol attached to the product.

(3) Transfection of Plasmid DNA to Colon Cancer Cell

First, human colon cancer derived HCT116 cells (DS Pharma Biomedical Co., Ltd.) were disseminated to a 6-hole plate so as to achieve about 70% confluent. The McCoy's 5A modified culture medium (product of Invitrogen Corporation) was used as the culture medium and the cells were cultured at 37° C. under 5% $CO_2$. The cells in each well were cultured for 24 hours, and then the purified plasmid DNAs containing the genes (f1-4), (f1-33), and (f1-48) were transfected using the transfection reagent Lipofectamine2000 (product name, product of Invitrogen Corporation) according to the protocol attached to the product. The composition in each well was set as follows. The cancer cells containing the plasmid DNAs containing the genes (f1-4), (f1-33), and (f1-48) were referred to as the protein expression cancer cells (F1-2), (F1-27), and (F1-42), respectively.

(Composition Per Well)

| | |
|---|---|
| Culture medium | 3000 μL |
| Lipofectamine2000 | 10 μL |
| Opti-MEM (product of Invitrogen Corporation) | 250 μL |
| Plasmid DNA | 2.5 μg |

(4) Measurement of Fluorescence Activity by FACS Analysis

After the transfection, the wells in the well were cultured at 37° C. under 5% $CO_2$ for 24 hours. Then, the hygromycin B solution (product of Wako) was added to the plate so that the concentration in each cell was 500 μg/mL, and the resultant was cultured another 14 days. After the culture, about $2 \times 10^5$ to $1 \times 10^6$ fluorescence signal positive cells were sorted from the cells in each well using the FACSaria III (product of BD Biosciences), and the sorted cells were cultured at 37° C. under 5% $CO_2$ another 5 days. Then, the cultured cells were subjected to a fluorescence activated cell sorting (FACS) analysis under the following conditions. As the control, the analysis was conducted in the same manner as described above except that the expression vectors were not transfected.

(FACS Analysis Conditions)

Measurement apparatus FACSaria III (product of BD Biosciences)

Figure 5:
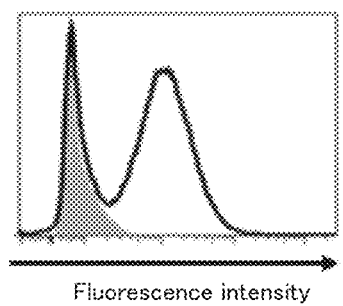
FIG. 5 shows graphs each showing the fluorescence intensity of each protein expression cancer cell in Example 5.
Figure 5:
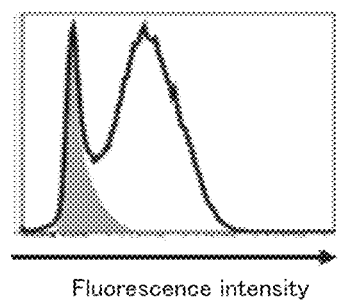
Figure 5:
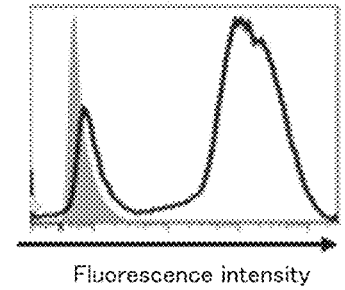
Figure 5:
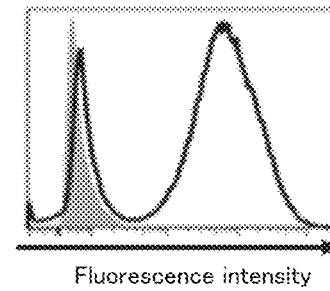

Filter Setting 488 nm blue laser; 502 nm LP mirror with a 530/30 nm band pass filter 405 nm violet laser; 502 nm LP mirror with a 530/30 nm band pass filter The results are shown in FIG. 5. FIG. 5 shows graphs showing the fluorescence activity of each protein expression cancer cell obtained with each filter. In FIG. 5, the vertical axis shows the number of cells, the horizontal axis shows the fluorescence intensity, the histogram indicated by the solid line shows the result of each protein expression cancer cell, and the histogram indicated by a gray line shows the result of the control. As shown in FIG. 5, the control did not show the peak showing the fluorescence activity, whereas the protein expression cancer cells (F1-27) and (F1-42) analyzed with the V500 filter and the protein expression cancer cells (F1-2) and (F1-42) analyzed with the FITC filter each showed the peak showing the fluorescence activity. These results showed that the novel fluorescent protein of the present invention has a fluorescence activity.

The results obtained by calculating the mean fluorescence intensity (MFI) of the fluorescence intensity of the protein expression cancer cells (F1-27) and (F1-42) analyzed with the V500 filter and the protein expression cancer cells (F1-2) and (F1-42) analyzed with the FITC filter are shown in the following table 11. As shown in table 11, the protein expression cancer cells (F1-27) and (F1-42) analyzed with the V500 filter and the protein expression cancer cells (F1-2) and (F1-42) analyzed with the FITC filter each showed a high MFI. These results showed that the novel fluorescent protein of the present invention has a superior fluorescence activity.

TABLE 11

|        | MFI(V500) | MFI(FITC) |
|--------|-----------|-----------|
| (F1-2) | —         | 21400     |
| (F1-27)| 1538      | —         |
| (F1-42)| 1004      | 10700     |

The invention of the present application was described above with reference to the embodiments and examples. However, the invention of the present application is not limited to the above-described embodiments and examples. Various changes that can be understood by those skilled in the art can be made in the configurations and details of the invention of the present application within the scope of the invention of the present application.

INDUSTRIAL APPLICABILITY

According to the present invention, a novel fluorescent protein can be provided. Thus, the present invention is a technique which can be significantly useful in a life science field, a medical field, an agricultural field, and the like.

SEQUENCE LISTING

TF15036WO_ST25.txt

---

The invention claimed is:

1. A novel protein including the following protein (F1) or (F3):

(F1) a protein consisting of an amino acid sequence of SEQ ID NO: 1, wherein
in the amino acid sequence of SEQ ID NO: 1,
the $Xaa_{52}$ is C, F, H, K, M, or T,
the $Xaa_{133}$ is L, Q, S, or T, and
the $Xaa_{154}$ is A, H, I, K, L, Q, V, or Y, and (F3) a protein comprising an amino acid sequence having at least 90% identity to the protein (F1) in which the $Xaa_{52}$, the $Xaa_{133}$, and the $Xaa_{154}$ are preserved and having a fluorescence activity.

2. The novel protein according to claim 1, wherein the combination of the Xaa.52, the $Xaa_{133}$, and the $Xaa_{154}$ is one of the following combinations,
the $Xaa_{52}$ is T, the $Xaa_{133}$ is S, and the $Xaa_{154}$ is Y,
the $Xaa_{52}$ is H, the $Xaa_{133}$ is T, and the $Xaa_{154}$ is K,
the $Xaa_{52}$ is C, the $Xaa_{133}$ is L, and the $Xaa_{154}$ is L,
the $Xaa_{52}$ is C, the $Xaa_{133}$ is S, and the $Xaa_{154}$ is H,
the $Xaa_{52}$ is T, the $Xaa_{133}$ is S, and the $Xaa_{154}$ is H,
the $Xaa_{52}$ is M, the $Xaa_{133}$ is L, and the $Xaa_{154}$ is V,
the $Xaa_{52}$ is F, the $Xaa_{133}$ is S, and the $Xaa_{154}$ is Q,
the $Xaa_{52}$ is K, the $Xaa_{133}$ is T, and the $Xaa_{154}$ is A,
the $Xaa_{52}$ is C, the $Xaa_{133}$ is Q, and the $Xaa_{154}$ is L,
the $Xaa_{52}$ is T, the $Xaa_{133}$ is T, and the $Xaa_{154}$ is I,
the $Xaa_{52}$ is K, the $Xaa_{133}$ is S, and the $Xaa_{154}$ is Q, and
the $Xaa_{52}$ is M, the $Xaa_{133}$ is L, and the $Xaa_{154}$ is A.

3. The novel protein according to claim 1, wherein a 205th amino acid $Xaa_{205}$ is substituted with I.

4. The novel protein according to claim 1, wherein a 198th amino acid $Xaa_{198}$ is substituted with L.

5. The novel protein according to claim 1 wherein the protein (F1) is a protein consisting of at least one amino acid sequence selected from the group consisting of SEQ ID NOs: 2 to 13, 34 to 66, and 67.

6. The novel protein according to claim 1, wherein the combination of the $Xaa_{52}$, the $Xaa_{133}$, and the $Xaa_{154}$ is one of the following combinations,
the $Xaa_{52}$ is T, the $Xaa_{133}$ is S, and the $Xaa_{154}$ is Y,
the $Xaa_{52}$ is H, the $Xaa_{133}$ is T, and the $Xaa_{154}$ is K,
the $Xaa_{52}$ is C, the $Xaa_{133}$ is L, and the $Xaa_{154}$ is L,
the $Xaa_{52}$ is C, the $Xaa_{133}$ is S, and the $Xaa_{154}$ is H,
the $Xaa_{52}$ is T, the $Xaa_{133}$ is S, and the $Xaa_{154}$ is H,
the $Xaa_{52}$ is M, the $Xaa_{133}$ is L, and the $Xaa_{154}$ is V,
the $Xaa_{52}$ is C, the $Xaa_{133}$ is Q, and the $Xaa_{154}$ is L,
the $Xaa_{52}$ is T, the $Xaa_{133}$ is T, and the $Xaa_{154}$ is I, and
the $Xaa_{52}$ is M, the $Xaa_{133}$ is L, and the $Xaa_{154}$ is A.

* * * * *

SEQUENCE LISTING

```
<160> NUMBER OF SEQ ID NOS: 106

<210> SEQ ID NO 1
<211> LENGTH: 219
<212> TYPE: PRT
<213> ORGANISM: Artificial Sequence
<220> FEATURE:
<223> OTHER INFORMATION: Synthetic fluorescent protein
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid

<400> SEQUENCE: 1

Met Thr Thr Phe Lys Ile Glu Ser Arg Ile His Gly Asn Leu Asn Gly
1               5                   10                  15

Glu Lys Phe Glu Leu Val Gly Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Xaa Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
```

```
                100                 105                 110
Glu Cys Ile Gly His Gly Phe Pro Ser Gln Ser Pro Ile Phe Lys Asp
            115                 120                 125

Thr Ile Val Lys Xaa Cys Pro Thr Val Asp Leu Met Leu Pro Met Ser
            130                 135                 140

Gly Asn Ile Ile Ala Ser Ser Tyr Ala Xaa Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
            195                 200                 205

Gln Gln Val Phe Asn Ser Ala Pro Arg Asp Met
            210                 215

<210> SEQ ID NO 2
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 2

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Ser Thr Cys Met Gly Tyr Gly Phe Tyr His Phe Ala Ser Phe
        50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
            130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
            195                 200                 205

Gln Gln Val Phe Asn Ser Ala Pro Arg Asp Met
            210                 215

<210> SEQ ID NO 3
<211> LENGTH: 219
<212> TYPE: PRT
```

<213> ORGANISM: Artificial Sequence
<220> FEATURE:
<223> OTHER INFORMATION: Synthetic fluorescent protein

<400> SEQUENCE: 3

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser His Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Thr Cys Pro Thr Val Asp Leu Met Leu Pro Met Ser
130                 135                 140

Gly Asn Ile Ile Ala Ser Ser Tyr Ala Lys Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
            195                 200                 205

Gln Gln Val Phe Asn Ser Ala Pro Arg Asp Met
            210                 215
```

<210> SEQ ID NO 4
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 4

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Ile Leu Glu
                85                  90                  95

Val Asn Phe Arg Tyr Thr Tyr Glu Phe Asn Lys Ile Ile Gly Asp Val
                100                 105                 110
```

```
Glu Cys Ile Gly His Gly Phe Pro Ser Gln Ser Pro Ile Phe Lys Asp
            115                 120                 125

Thr Ile Val Lys Leu Cys Pro Thr Val Asp Leu Met Leu Pro Met Ser
            130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
            195                 200                 205

Gln Gln Val Phe Asn Ser Ala Pro Arg Asp Met
            210                 215
```

<210> SEQ ID NO 5
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 5

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
            130                 135                 140

Gly Asn Ile Ile Ala Ser Ser Tyr Ala His Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
            195                 200                 205

Gln Gln Val Phe Asn Ser Ala Pro Arg Asp Met
            210                 215
```

<210> SEQ ID NO 6
<211> LENGTH: 219
<212> TYPE: PRT
<213> ORGANISM: Artificial Sequence
<220> FEATURE:

<223> OTHER INFORMATION: Synthetic fluorescent protein

<400> SEQUENCE: 6

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
        35                  40                  45

Leu Leu Ser Thr Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
        130                 135                 140

Gly Asn Ile Ile Ala Ser Ser Tyr Ala His Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 7
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 7

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
        35                  40                  45

Leu Leu Ser Met Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

```
Thr Ile Val Lys Leu Cys Pro Thr Val Asp Leu Met Leu Pro Met Ser
        130                 135                 140

Gly Asn Ile Ile Ala Ser Ser Tyr Ala Val Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215
```

<210> SEQ ID NO 8
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 8

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
                20                  25                  30

Glu Ile Glu Met Lys Thr Lys Asp Lys Pro Leu Ala Phe Ser Pro Phe
            35                  40                  45

Leu Leu Ser Phe Cys Met Gly Tyr Gly Phe Tyr His Phe Ala Ser Phe
50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
        130                 135                 140

Gly Asn Ile Ile Ala Ser Ser Tyr Ala Gln Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215
```

<210> SEQ ID NO 9
<211> LENGTH: 219
<212> TYPE: PRT
<213> ORGANISM: Artificial Sequence
<220> FEATURE:
<223> OTHER INFORMATION: Synthetic fluorescent protein

```
<400> SEQUENCE: 9

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser Lys Cys Met Gly Tyr Gly Phe Tyr His Phe Ala Ser Phe
        50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Thr Cys Pro Thr Val Asp Leu Met Leu Pro Met Ser
    130                 135                 140

Gly Asn Ile Ile Ala Ser Ser Tyr Ala Ala Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
                180                 185                 190

Arg Val Glu Glu Thr His Thr Lys Glu Asn Leu Ala Met Val Glu Tyr
            195                 200                 205

Gln Gln Val Phe Asn Ser Ala Pro Arg Asp Met
        210                 215

<210> SEQ ID NO 10
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 10

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
        50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Gln Cys Pro Thr Val Asp Leu Met Leu Pro Met Ser
```

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 11
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 11

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser Thr Cys Met Gly Tyr Gly Phe Tyr His Phe Ala Ser Phe
50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Thr Cys Pro Thr Val Asp Leu Met Leu Pro Met Ser
130                 135                 140

Gly Asn Ile Ile Ala Ser Ser Tyr Ala Ile Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 12
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 12

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Ser Lys Cys Met Gly Tyr Gly Phe Tyr His Phe Ala Ser Phe
        50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
        130                 135                 140

Gly Asn Ile Ile Ala Ser Ser Tyr Ala Gln Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
            195                 200                 205

Gln Gln Val Phe Asn Ser Ala Pro Arg Asp Met
        210                 215
```

<210> SEQ ID NO 13
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 13

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Ser Met Cys Met Gly Tyr Gly Phe Tyr His Phe Ala Ser Phe
        50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Leu Cys Pro Thr Val Asp Leu Met Leu Pro Met Ser
        130                 135                 140
```

```
Gly Asn Ile Ile Ala Ser Ser Tyr Ala Ala Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215
```

```
<210> SEQ ID NO 14
<211> LENGTH: 660
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (154)..(156)
<223> OTHER INFORMATION: n is a, c, g, or t
<220> FEATURE:
<221> NAME/KEY: misc_feature
<222> LOCATION: (397)..(399)
<223> OTHER INFORMATION: n is a, c, g, or t
<220> FEATURE:
<221> NAME/KEY: misc_feature
<222> LOCATION: (460)..(462)
<223> OTHER INFORMATION: n is a, c, g, or t

<400> SEQUENCE: 14
atgacaacct tcaaaatcga gtcccggatc catggcaacc tcaacgggga gaagttcgag      60
ttggttggag gtggagtagg tgaggagggt cgcctcgaga ttgagatgaa gactaaagat     120
aaaccactgg cattctctcc cttcctgctg tccnnntgca tgggttacgg gttctaccac     180
ttcgccagct tcccaaaggg gactaagaac atctatcttc atgctgcaac aaacggaggt     240
tacaccaaca ccaggaagga gatctatgaa gacggcggca tcttggaggt caacttccgt     300
tacacttacg agttcaacaa gatcatcggt gacgtcgagt gcattggaca tggattccca     360
agtcagagtc cgatcttcaa ggacacgatc gtgaagnnnt gtcccacggt ggacctgatg     420
ttgccgatgt ccgggaacat catcgccagc tcctacgctn nngccttcca actgaaggac     480 ggctcttttct acacggcaga agtcaagaac aacatagact tcaagaatcc aatccacgag     540
tccttctcga gtcggggcc atgttcacc acagacgtg tcgaggagac tcacaccaag        600
gagaaccttg ccatggtgga gtaccagcag gttttcaaca gcgccccaag agacatgtag     660
```

```
<210> SEQ ID NO 15
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 15
atgacaacct tcaaaatcga gtcccggatc catggcaacc tcaacgggga gaagttcgag      60
ttggttggag gtggagtagg tgaggagggt cgcctcgaga ttgagatgaa gactaaagat     120
aaaccactgg cattctctcc cttcctgctg tccacatgca tgggttacgg gttctaccac     180
ttcgccagct tcccaaaggg gactaagaac atctatcttc atgctgcaac aaacggaggt     240
tacaccaaca ccaggaagga gatctatgaa gacggcggca tcttggaggt caacttccgt     300
```
tacacttacg agttcaacaa gatcatcggt gacgtcgagt gcattggaca tggattccca    360
agtcagagtc cgatcttcaa ggacacgatc gtgaagtctt gtcccacggt ggacctgatg    420
ttgccgatgt ccgggaacat catcgccagc tcctacgctt acgccttcca actgaaggac    480
ggctctttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660

<210> SEQ ID NO 16
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 16
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tccacctgca tgggttacgg gttctaccac    180
ttcgccagct cccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagct gtcccacggt ggacctgatg    420
ttgccgatgt ccgggaacat catcgccagc tcctacgctt atgccttcca actgaaggac    480
ggctctttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660

<210> SEQ ID NO 17
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 17
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tccacttgca tgggttacgg gttctaccac    180
ttcgccagct cccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagtt gtcccacggt ggacctgatg    420
ttgccgatgt ccgggaacat catcgccagc tcctacgctt acgccttcca actgaaggac    480
ggctctttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660

<210> SEQ ID NO 18
<211> LENGTH: 660

<212> TYPE: DNA
<213> ORGANISM: Artificial Sequence
<220> FEATURE:
<223> OTHER INFORMATION: Synthetic oligonucleotide

<400> SEQUENCE: 18

| | | | | | | |
|---|---|---|---|---|---|---|
| atgacaacct | tcaaaatcga | gtcccggatc | catggcaacc | tcaacgggga | gaagttcgag | 60 |
| ttggttggag | gtggagtagg | tgaggagggt | cgcctcgaga | ttgagatgaa | gactaaagat | 120 |
| aaaccactgg | cattctctcc | cttcctgctg | tcccactgca | tgggttacgg | gttctaccac | 180 |
| ttcgccagct | tcccaaaggg | gactaagaac | atctatcttc | atgctgcaac | aaacggaggt | 240 |
| tacaccaaca | ccaggaagga | gatctatgaa | gacggcggca | tcttggaggt | caacttccgt | 300 |
| tacacttacg | agttcaacaa | gatcatcggt | gacgtcgagt | gcattggaca | tggattccca | 360 |
| agtcagagtc | cgatcttcaa | ggacacgatc | gtgaagactt | gtcccacggt | ggacctgatg | 420 |
| ttgccgatgt | ccgggaacat | catcgccagc | tcctacgcta | aggccttcca | actgaaggac | 480 |
| ggctctttct | acacggcaga | agtcaagaac | aacatagact | caagaatcc | aatccacgag | 540 |
| tccttctcga | gtcggggcc | catgttcacc | cacagacgtg | tcgaggagac | tcacaccaag | 600 |
| gagaaccttg | ccatggtgga | gtaccagcag | gttttcaaca | gcgccccaag | agacatgtag | 660 |

<210> SEQ ID NO 19
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 19

| | | | | | | |
|---|---|---|---|---|---|---|
| atgacaacct | tcaaaatcga | gtcccggatc | catggcaacc | tcaacgggga | gaagttcgag | 60 |
| ttggttggag | gtggagtagg | tgaggagggt | cgcctcgaga | ttgagatgaa | gactaaagat | 120 |
| aaaccactgg | cattctctcc | cttcctgctg | tcccactgca | tgggttacgg | gttctaccac | 180 |
| ttcgccagct | tcccaaaggg | gactaagaac | atctatcttc | atgctgcaac | aaacggaggt | 240 |
| tacaccaaca | ccaggaagga | gatctatgaa | gacggcggca | tcttggaggt | caacttccgt | 300 |
| tacacttacg | agttcaacaa | gatcatcggt | gacgtcgagt | gcattggaca | tggattccca | 360 |
| agtcagagtc | cgatcttcaa | ggacacgatc | gtgaagacat | gtcccacggt | ggacctgatg | 420 |
| ttgccgatgt | ccgggaacat | catcgccagc | tcctacgcta | aggccttcca | actgaaggac | 480 |
| ggctctttct | acacggcaga | agtcaagaac | aacatagact | caagaatcc | aatccacgag | 540 |
| tccttctcga | gtcggggcc | catgttcacc | cacagacgtg | tcgaggagac | tcacaccaag | 600 |
| gagaaccttg | ccatggtgga | gtaccagcag | gttttcaaca | gcgccccaag | agacatgtag | 660 |

<210> SEQ ID NO 20
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 20

| | | | | | | |
|---|---|---|---|---|---|---|
| atgacaacct | tcaaaatcga | gtcccggatc | catggcaacc | tcaacgggga | gaagttcgag | 60 |
| ttggttggag | gtggagtagg | tgaggagggt | cgcctcgaga | ttgagatgaa | gactaaagat | 120 |
| aaaccactgg | cattctctcc | cttcctgctg | tcctgctgca | tgggttacgg | gttctaccac | 180 |
| ttcgccagct | tcccaaaggg | gactaagaac | atctatcttc | atgctgcaac | aaacggaggt | 240 |

```
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagttat gtcccacggt ggacctgatg    420
ttgccgatgt ccgggaacat catcgccagc tcctacgctc ttgccttcca actgaaggac    480
ggctctttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660
```

\<210\> SEQ ID NO 21
\<211\> LENGTH: 660
\<212\> TYPE: DNA
\<213\> ORGANISM: Artificial Sequence
\<220\> FEATURE:
\<223\> OTHER INFORMATION: Synthetic oligonucleotide

\<400\> SEQUENCE: 21

```
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tcctgctgca tgggttacgg gttctaccac    180
ttcgccagct tcccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagct gtcccacggt ggacctgatg    420
ttgccgatgt ccgggaacat catcgccagc tcctacgctc atgccttcca actgaaggac    480
ggctctttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660
```

\<210\> SEQ ID NO 22
\<211\> LENGTH: 660
\<212\> TYPE: DNA
\<213\> ORGANISM: Artificial Sequence
\<220\> FEATURE:
\<223\> OTHER INFORMATION: Synthetic oligonucleotide

\<400\> SEQUENCE: 22

```
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tcctgttgca tgggttacgg gttctaccac    180
ttcgccagct tcccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagct gtcccacggt ggacctgatg    420
ttgccgatgt ccgggaacat catcgccagc tcctacgctc acgccttcca actgaaggac    480
ggctctttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660
```

<210> SEQ ID NO 23
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 23

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
aaaccactgg cattctctcc cttcctgctg tccacgtgca tgggttacgg gttctaccac   180
ttcgccagct tcccaaaggg gactaagaac atctatcttc atgctgcaac aaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagagct gtcccacggt ggacctgatg   420
ttgccgatgt ccgggaacat catcgccagc tcctacgctc acgccttcca actgaaggac   480
ggctcttcct acacggcaga agtcaagaac aacatagact tcaagaatcc aatccacgag   540
tccttctcga gtcggggcc catgttcacc cacagacgtg tcgaggagac tcacaccaag   600
gagaaccttg ccatggtgga gtaccagcag gttttcaaca gcgccccaag agacatgtag   660
```

<210> SEQ ID NO 24
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 24

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
aaaccactgg cattctctcc cttcctgctg tccatgtgca tgggttacgg gttctaccac   180
ttcgccagct tcccaaaggg gactaagaac atctatcttc atgctgcaac aaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagctgt gtcccacggt ggacctgatg   420
ttgccgatgt ccgggaacat catcgccagc tcctacgctg tagccttcca actgaaggac   480
ggctcttcct acacggcaga agtcaagaac aacatagact tcaagaatcc aatccacgag   540
tccttctcga gtcggggcc catgttcacc cacagacgtg tcgaggagac tcacaccaag   600
gagaaccttg ccatggtgga gtaccagcag gttttcaaca gcgccccaag agacatgtag   660
```

<210> SEQ ID NO 25
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 25

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
aaaccactgg cattctctcc cttcctgctg tccatgtgca tgggttacgg gttctaccac   180
```

```
ttcgccagct tcccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagctct gtcccacggt ggacctgatg    420
ttgccgatgt ccgggaacat catcgccagc tcctacgctg tggccttcca actgaaggac    480 ggctcttttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660
```

<210> SEQ ID NO 26
<211> LENGTH: 660
<212> TYPE: DNA
<213> ORGANISM: Artificial Sequence
<220> FEATURE:
<223> OTHER INFORMATION: Synthetic oligonucleotide
<400> SEQUENCE: 26

```
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tccaaatgca tgggttacgg gttctaccac    180
ttcgccagct cccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagct gtcccacggt ggacctgatg    420
ttgccgatgt ccgggaacat catcgccagc tcctacgctc aagccttcca actgaaggac    480 ggctcttttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660
```

<210> SEQ ID NO 27
<211> LENGTH: 660
<212> TYPE: DNA
<213> ORGANISM: Artificial Sequence
<220> FEATURE:
<223> OTHER INFORMATION: Synthetic oligonucleotide
<400> SEQUENCE: 27

```
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tccaaatgca tgggttacgg gttctaccac    180
ttcgccagct cccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagactt gtcccacggt ggacctgatg    420
ttgccgatgt ccgggaacat catcgccagc tcctacgctg ctgccttcca actgaaggac    480 ggctcttttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatggtgga gtaccagcag gttttcaaca gcgccccaag agacatgtag    660
```

<210> SEQ ID NO 28
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 28

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
aaaccactgg cattctctcc cttcctgctg tcctgttgca tgggttacgg gttctaccac   180
ttcgccagct cccaaaggg gactaagaac atctatcttc atgctgcaac aaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagcaat gtcccacggt ggacctgatg   420
ttgccgatgt ccgggaacat catcgccagc tcctacgctc ttgccttcca actgaaggac   480
ggctctttct acacggcaga agtcaagaac aacatagact tcaagaatcc aatccacgag   540
tccttctcga gtcggggcc catgttcacc cacagacgtg tcgaggagac tcacaccaag   600
gagaaccttg ccatggtgga gtaccagcag gttttcaaca gcgccccaag agacatgtag   660
```

<210> SEQ ID NO 29
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 29

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
aaaccactgg cattctctcc cttcctgctg tcctgctgca tgggttacgg gttctaccac   180
ttcgccagct cccaaaggg gactaagaac atctatcttc atgctgcaac aaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagcaat gtcccacggt ggacctgatg   420
ttgccgatgt ccgggaacat catcgccagc tcctacgctt tggccttcca actgaaggac   480
ggctctttct acacggcaga agtcaagaac aacatagact tcaagaatcc aatccacgag   540
tccttctcga gtcggggcc catgttcacc cacagacgtg tcgaggagac tcacaccaag   600
gagaaccttg ccatggtgga gtaccagcag gttttcaaca gcgccccaag agacatgtag   660
```

<210> SEQ ID NO 30
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 30

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
```

```
aaaccactgg cattctctcc cttcctgctg tccacttgca tgggttacgg gttctaccac    180
ttcgccagct tcccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagacat gtcccacggt ggacctgatg    420
ttgccgatgt ccgggaacat catcgccagc tcctacgcta ttgccttcca actgaaggac    480 ggctcttttct acacggcaga agtcaagaac aacatagact tcaagaatcc aatccacgag    540
tccttctcga gtcggggcc catgttcacc cacagacgtg tcgaggagac tcacaccaag    600
gagaaccttg ccatggtgga gtaccagcag gttttcaaca gcgcccccaag agacatgtag    660
```

<210> SEQ ID NO 31
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 31

```
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tccaaatgca tgggttacgg gttctaccac    180
ttcgccagct tcccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagct gtcccacggt ggacctgatg    420
ttgccgatgt ccgggaacat catcgccagc tcctacgctc aagccttcca actgaaggac    480 ggctcttttct acacggcaga agtcaagaac aacatagact tcaagaatcc aatccacgag    540
tccttctcga gtcggggcc catgttcacc cacagacgtg tcgaggagac tcacaccaag    600
gagaaccttg ccatggtgga gtaccagcag gttttcaaca gcgcccccaag agacatgtag    660
```

<210> SEQ ID NO 32
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 32

```
atgacaacct tcaaaatcga gtcccggatc catggcaacc tcaacgggga gaagttcgag     60
ttggttggag gtggagtagg tgaggagggt cgcctcgaga ttgagatgaa gactaaagat    120
aaaccactgg cattctctcc cttcctgctg tccatgtgca tgggttacgg gttctaccac    180
ttcgccagct tcccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagctct gtcccacggt ggacctgatg    420
ttgccgatgt ccgggaacat catcgccagc tcctacgctg ccgccttcca actgaaggac    480 ggctcttttct acacggcaga agtcaagaac aacatagact tcaagaatcc aatccacgag    540
tccttctcga gtcggggcc catgttcacc cacagacgtg tcgaggagac tcacaccaag    600
```
gagaaccttg ccatggtgga gtaccagcag gttttcaaca gcgccccaag agacatgtag    660

<210> SEQ ID NO 33
<211> LENGTH: 672
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (161)..(163)
<223> OTHER INFORMATION: n is a, c, g, or t
<220> FEATURE:
<221> NAME/KEY: misc_feature
<222> LOCATION: (404)..(406)
<223> OTHER INFORMATION: n is a, c, g, or t
<220> FEATURE:
<221> NAME/KEY: misc_feature
<222> LOCATION: (467)..(469)
<223> OTHER INFORMATION: n is a, c, g, or t

<400> SEQUENCE: 33
aagcttgatg acaaccttca aaatcgagtc ccggatccat ggcaacctca acggggagaa     60
gttcgagttg gttggaggtg gagtaggtga ggagggtcgc ctcgagattg agatgaagac    120
taaagataaa ccactggcat tctctccctt cctgctgtcc nnntgcatgg gttacgggtt    180
ctaccacttc gccagcttcc caaagggac taagaacatc tatcttcatg ctgcaacaaa    240
cggaggttac accaacacca ggaaggagat ctatgaagac ggcggcatct tggaggtcaa    300
cttccgttac acttacgagt tcaacaagat catcggtgac gtcgagtgca ttggacatgg    360
attcccaagt cagagtccga tcttcaagga cacgatcgtg aagnnntgtc ccacggtgga    420
cctgatgttg ccgatgtccg ggaacatcat cgccagctcc tacgctnnng ccttccaact    480
gaaggacggc tctttctaca cggcagaagt caagaacaac atagacttca gaatccaat    540 ccacgagtcc ttctcgaagt cggggcccat gttcacccac agacgtgtcg aggagactca    600
caccaaggag aaccttgcca tggtggagta ccagcaggtt tcaacagcg ccccaagaga    660 catgtagaat tc    672

<210> SEQ ID NO 34
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 34

Met Thr Thr Phe Lys Ile Glu Ser Arg Ile His Gly Asn Leu Asn Gly
1               5                   10                  15

Glu Lys Phe Glu Leu Val Gly Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Thr Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
                180                 185                 190

Arg Val Glu Glu Thr His Thr Lys Glu Asn Leu Ala Ile Val Glu Tyr
                195                 200                 205

Gln Gln Val Phe Asn Ser Ala Pro Arg Asp Met
    210                 215

<210> SEQ ID NO 35
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 35

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Thr Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
                180                 185                 190

Arg Val Glu Glu Thr Leu Thr Lys Glu Asn Leu Ala Ile Val Glu Tyr
                195                 200                 205

Gln Gln Val Phe Asn Ser Ala Pro Arg Asp Met
    210                 215

<210> SEQ ID NO 36
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 36

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Thr Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Tyr Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Leu Lys Ser Gly Pro Met Phe Thr His Arg
            180                 185                 190

Arg Val Glu Glu Thr Leu Thr Lys Glu Asn Leu Ala Ile Val Glu Tyr
        195                 200                 205

Gln Gln Val Phe Asn Ser Ala Pro Arg Asp Met
    210                 215

<210> SEQ ID NO 37
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 37

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Thr Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp

```
                    115                 120                 125
Thr Ile Val Lys Ser Cys Pro Thr Val Asp Leu Met Leu Pro Met Pro
    130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                    165                 170                 175

Pro Ile His Glu Ser Phe Ser Lys Ser Gly Pro Met Phe Thr His Arg
                180                 185                 190

Arg Val Glu Glu Thr Leu Thr Lys Glu Asn Leu Ala Ile Val Glu Tyr
                    195                 200                 205

Gln Gln Val Phe Asn Ser Ala Pro Arg Asp Met
    210                 215

<210> SEQ ID NO 38
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 38

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
                20                  25                  30

Glu Ile Glu Met Lys Thr Lys Asp Lys Pro Leu Ala Phe Ser Pro Phe
            35                  40                  45

Leu Leu Ser Thr Cys Met Gly Tyr Gly Phe Tyr His Phe Ala Ser Phe
50                  55                  60

Pro Lys Gly Ile Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                    165                 170                 175

Pro Ile His Glu Ser Phe Ser Lys Ser Gly Pro Met Phe Thr His Arg
                180                 185                 190

Arg Val Glu Glu Thr Leu Thr Lys Glu Asn Leu Ala Ile Val Glu Tyr
                    195                 200                 205

Gln Gln Val Phe Asn Ser Ala Pro Arg Asp Met
    210                 215

<210> SEQ ID NO 39
<211> LENGTH: 219
<212> TYPE: PRT
<213> ORGANISM: Artificial Sequence
<220> FEATURE:
<223> OTHER INFORMATION: Synthetic fluorescent protein
```

<400> SEQUENCE: 39

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Thr Thr Cys Met Gly Tyr Gly Phe Tyr His Phe Ala Ser Phe
50                      55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Leu Thr Lys Glu Asn Leu Ala Ile Val Glu Tyr
            195                 200                 205

Gln Gln Val Phe Asn Ser Ala Pro Arg Asp Met
            210                 215

<210> SEQ ID NO 40
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 40

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Ser Thr Cys Met Gly Tyr Gly Phe Tyr His Phe Ala Ser Phe
50                      55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

```
Thr Ile Val Lys Ser Cys Pro Thr Val Asp Leu Met Leu Pro Met Ser
            130                 135                 140
Gly Asn Ile Ile Val Ser Ser Tyr Ala Tyr Ala Phe Gln Leu Lys Asp
145                 150                 155                 160
Gly Ser Phe Tyr Thr Ala Glu Val Lys Asn Asn Ile Asp Phe Lys Asn
                165                 170                 175
Pro Ile His Glu Ser Phe Ser Lys Ser Gly Pro Met Phe Thr His Arg
            180                 185                 190
Arg Val Glu Glu Thr Leu Thr Lys Glu Asn Leu Ala Ile Val Glu Tyr
                195                 200                 205
Gln Gln Val Phe Asn Ser Ala Pro Arg Asp Met
            210                 215
```

<210> SEQ ID NO 41
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 41

```
Met Thr Thr Phe Lys Ile Glu Ser Arg Ile His Gly Asn Leu Asn Gly
1               5                   10                  15
Glu Lys Phe Glu Leu Val Gly Gly Val Gly Glu Gly Arg Leu
                20                  25                  30
Glu Ile Glu Met Lys Thr Lys Asp Lys Pro Leu Ala Phe Ser Pro Phe
            35                  40                  45
Leu Leu Ser Thr Cys Met Gly Tyr Gly Phe Tyr His Phe Ala Ser Phe
50                  55                  60
Pro Lys Gly Thr Lys Asn Ile Tyr Leu His Ala Ala Thr Asn Gly Gly
65                  70                  75                  80
Tyr Thr Asn Thr Arg Lys Glu Ile Tyr Glu Asp Gly Gly Ile Leu Glu
                85                  90                  95
Val Asn Phe Arg Tyr Thr Tyr Glu Phe Asn Lys Ile Ile Gly Asp Val
                100                 105                 110
Glu Cys Ile Gly His Gly Phe Pro Ser Gln Ser Pro Ile Phe Lys Asp
            115                 120                 125
Thr Ile Val Lys Ser Cys Pro Thr Val Asp Leu Met Leu Pro Met Thr
            130                 135                 140
Gly Asn Ile Ile Thr Ser Ser Tyr Ala Tyr Ala Phe Gln Leu Lys Asp
145                 150                 155                 160
Gly Ser Phe Tyr Thr Ala Glu Val Lys Asn Asn Ile Asp Phe Lys Asn
                165                 170                 175
Pro Ile His Glu Ser Phe Ser Lys Ser Gly Pro Met Phe Thr His Arg
            180                 185                 190
Arg Val Glu Glu Thr Leu Thr Lys Glu Asn Leu Ala Ile Val Glu Tyr
                195                 200                 205
Gln Gln Val Phe Asn Ser Ala Pro Arg Asp Met
            210                 215
```

<210> SEQ ID NO 42
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 42

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
                20                  25                  30

Glu Ile Glu Met Arg Thr Lys Asp Lys Pro Leu Ala Phe Ser Pro Phe
            35                  40                  45

Leu Leu Ser Thr Cys Met Gly Tyr Gly Phe Tyr His Phe Ala Ser Phe
        50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
        130                 135                 140

Gly Asn Ile Ile Val Ser Ser Tyr Ala Tyr Ala Phe Gln Leu Lys Asp
145                 150                 155                 160

Gly Thr Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Leu Thr Lys Glu Asn Leu Ala Ile Val Glu Tyr
                195                 200                 205

Gln Gln Val Phe Asn Ser Ala Pro Arg Asp Met
210                 215

<210> SEQ ID NO 43
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 43

Met Thr Thr Phe Lys Ile Glu Ser Arg Ile His Gly Asn Leu Asn Gly
1               5                   10                  15

Glu Glu Phe Glu Leu Val Gly Gly Val Gly Glu Glu Gly Arg Leu
                20                  25                  30

Glu Ile Glu Met Lys Thr Lys Asp Lys Pro Leu Ala Phe Ser Pro Phe
            35                  40                  45

Leu Leu Ser Thr Cys Met Gly Tyr Gly Phe Tyr His Phe Ala Ser Phe
        50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Pro
        130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Leu Thr Lys Glu Asn Leu Ala Ile Val Glu Tyr
        195                 200                 205

Gln Gln Val Phe Asn Ser Ala Pro Arg Asp Met
    210                 215

<210> SEQ ID NO 44
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 44

Met Thr Thr Phe Lys Ile Glu Ser Arg Ile His Gly Asn Leu Asn Gly
1               5                   10                  15

Glu Glu Phe Glu Leu Val Gly Gly Val Gly Glu Gly Arg Leu
                20                  25                  30

Glu Ile Glu Met Lys Thr Lys Asp Lys Pro Leu Ala Phe Ser Pro Phe
            35                  40                  45

Leu Leu Ser Thr Cys Met Gly Tyr Gly Phe Tyr His Phe Ala Ser Phe
        50                  55                  60

Pro Lys Gly Ile Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Ser Cys Pro Thr Val Asp Leu Met Leu Pro Met Ser
130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Arg Asn
                165                 170                 175

Pro Ile His Glu Ser Phe Ser Lys Ser Gly Pro Met Phe Thr His Arg
            180                 185                 190

Arg Val Glu Glu Thr Leu Thr Lys Glu Asn Leu Ala Ile Val Glu Tyr
        195                 200                 205

Gln Gln Val Phe Asn Ser Ala Pro Arg Asp Met
    210                 215

<210> SEQ ID NO 45
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 45

Met Thr Thr Phe Lys Ile Glu Ser Arg Ile His Gly Asn Leu Asn Gly

```
            1               5                  10                 15
          Glu Lys Phe Glu Leu Val Gly Gly Gly Val Gly Glu Glu Gly Arg Leu
                       20                  25                  30

Glu Ile Glu Met Lys Thr Lys Asp Lys Pro Leu Ala Phe Ser Pro Phe
                       35                  40                  45

Leu Leu Ser Thr Cys Met Gly Tyr Gly Phe Tyr His Phe Ala Ser Phe
                       50                  55                  60

Pro Lys Gly Ile Lys Asn Ile Tyr Leu His Ala Ala Thr Asn Gly Gly
           65                  70                  75                  80

Tyr Thr Asn Thr Arg Lys Glu Ile Tyr Glu Asp Gly Gly Val Leu Glu
                               85                  90                  95

Val Asn Phe Arg Tyr Thr Tyr Glu Phe Asp Lys Ile Ile Gly Asp Val
                      100                 105                 110

Glu Cys Ile Gly His Gly Phe Pro Ser Gln Ser Pro Ile Phe Lys Asp
                      115                 120                 125

Thr Ile Val Lys Ser Cys Pro Thr Val Asp Leu Met Leu Pro Met Ser
                130                 135                 140

Gly Asn Ile Ile Ala Ser Ser Tyr Ala Tyr Ala Phe Gln Leu Lys Asp
          145                 150                 155                 160

Gly Ser Phe Tyr Thr Ala Glu Val Lys Asn Asn Ile Asp Phe Lys Asn
                              165                 170                 175

Pro Ile His Glu Ser Phe Ser Lys Ser Gly Pro Met Phe Thr His Arg
                              180                 185                 190

Arg Val Glu Glu Thr Leu Thr Lys Glu Asn Leu Ala Ile Val Glu Tyr
                              195                 200                 205

Gln Gln Val Phe Asn Ser Ala Pro Arg Asp Met
                      210                 215

<210> SEQ ID NO 46
          <211> LENGTH: 219
          <212> TYPE: PRT
          <213> ORGANISM: Artificial Sequence
          <220> FEATURE:
          <223> OTHER INFORMATION: Synthetic fluorescent protein

<400> SEQUENCE: 46

Met Thr Thr Phe Lys Ile Glu Ser Arg Ile His Gly Asn Leu Asn Gly
           1               5                  10                 15

Glu Lys Phe Glu Leu Val Gly Gly Gly Val Gly Glu Glu Gly Arg Leu
                       20                  25                  30

Glu Ile Glu Met Lys Thr Lys Asp Lys Pro Leu Ala Phe Ser Pro Phe
                       35                  40                  45

Leu Leu Ser Thr Cys Met Gly Tyr Gly Phe Tyr His Phe Ala Ser Phe
                       50                  55                  60

Pro Lys Gly Thr Lys Asn Ile Tyr Leu His Ala Ala Thr Asn Gly Gly
           65                  70                  75                  80

Tyr Thr Asn Thr Arg Lys Glu Ile Tyr Glu Asp Gly Gly Ile Leu Glu
                               85                  90                  95

Val Asn Phe Arg Tyr Thr Tyr Glu Phe Asp Lys Ile Ile Gly Asp Val
                      100                 105                 110

Glu Cys Ile Gly His Gly Phe Pro Ser Gln Ser Pro Ile Phe Lys Asp
                      115                 120                 125

Thr Ile Val Lys Ser Cys Pro Thr Val Asp Leu Met Leu Pro Met Ser
                130                 135                 140

Gly Asn Ile Ile Ala Ser Ser Tyr Ala Tyr Ala Phe Gln Leu Lys Asp
```

```
                145                 150                 155                 160
Gly Ser Phe Tyr Thr Ala Glu Val Lys Asn Asn Ile Asp Phe Lys Asn
                    165                 170                 175

Pro Ile His Glu Ser Phe Leu Lys Ser Gly Pro Met Phe Thr His Arg
                    180                 185                 190

Arg Val Glu Glu Thr Leu Thr Lys Glu Asn Leu Ala Ile Val Glu Tyr
                    195                 200                 205

Gln Gln Val Phe Asn Ser Ala Pro Arg Asp Met
                    210                 215

<210> SEQ ID NO 47
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 47

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
                20                  25                  30

Glu Ile Glu Met Lys Thr Lys Asp Lys Pro Leu Ala Phe Ser Pro Phe
                35                  40                  45

Leu Leu Ser Thr Ser Met Gly Tyr Gly Phe Tyr His Phe Ala Ser Phe
            50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                    85                  90                  95

Val Asn Phe Arg Tyr Thr Tyr Glu Phe Asn Lys Ile Ile Gly Asp Val
                    100                 105                 110

Glu Cys Ile Gly His Gly Phe Pro Ser Gln Ser Pro Ile Phe Lys Asp
                    115                 120                 125

Thr Ile Val Lys Ser Cys Pro Thr Val Asp Leu Met Leu Pro Met Ser
130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Asp Val Lys Asn Asn Ile Asp Phe Lys Asn
                    165                 170                 175

Pro Ile His Glu Ser Phe Ser Lys Ser Gly Pro Met Phe Thr His Arg
                    180                 185                 190

Arg Val Glu Glu Thr Leu Thr Lys Glu Asn Leu Ala Ile Val Glu Tyr
                    195                 200                 205

Gln Gln Val Phe Asn Ser Ala Pro Arg Asp Met
                    210                 215

<210> SEQ ID NO 48
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 48

Met Thr Thr Phe Lys Ile Glu Ser Arg Ile His Gly Asn Leu Asn Gly
1               5                   10                  15
```

```
Glu Lys Phe Glu Leu Val Gly Gly Val Gly Glu Glu Gly Arg Leu
             20                  25                  30

Glu Ile Glu Met Lys Thr Lys Asp Lys Pro Leu Ala Phe Ser Pro Phe
             35                  40                  45

Leu Leu Thr Thr Cys Met Gly Tyr Gly Phe Tyr His Phe Ala Ser Phe
 50                      55                  60

Pro Lys Gly Ile Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Ser Cys Pro Thr Val Asp Leu Met Leu Pro Met Ser
            130                 135                 140

Gly Asn Ile Ile Ala Ser Ser Tyr Ala Tyr Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
                180                 185                 190

Arg Val Glu Glu Thr Leu Thr Lys Glu Asn Leu Ala Ile Val Glu Tyr
            195                 200                 205

Gln Gln Val Phe Asn Ser Ala Pro Arg Asp Met
210                 215

<210> SEQ ID NO 49
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 49

Met Thr Thr Phe Lys Ile Glu Ser Arg Ile His Gly Asn Leu Asn Gly
 1               5                  10                  15

Glu Lys Phe Glu Leu Val Gly Gly Val Gly Glu Glu Gly Arg Leu
             20                  25                  30

Glu Ile Glu Met Lys Thr Lys Asp Lys Pro Leu Ala Phe Ser Pro Phe
             35                  40                  45

Leu Leu Ser Cys Cys Met Gly Tyr Gly Phe Tyr His Phe Ala Ser Phe
 50                      55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Gln Cys Pro Thr Val Asp Leu Met Leu Pro Met Ser
            130                 135                 140

Gly Asn Ile Ile Ala Ser Ser Tyr Ala Leu Ala Phe Gln Leu Lys Asp
145                 150                 155                 160
```

```
Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
        195                 200                 205

Gln Gln Val Phe Asn Ser Ala Pro Arg Asp Met
    210                 215

<210> SEQ ID NO 50
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 50

Met Thr Thr Phe Lys Ile Glu Ser Arg Ile Arg Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Leu Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Gln Cys Pro Thr Val Asp Leu Met Leu Pro Met Ser
    130                 135                 140

Gly Asn Ile Ile Ala Ser Ser Tyr Ala Leu Ala Phe Arg Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
        195                 200                 205

Gln Gln Val Phe Asn Ser Ala Pro Arg Asp Met
    210                 215

<210> SEQ ID NO 51
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 51

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30
```

Glu Ile Glu Met Lys Thr Lys Asp Lys Pro Leu Ala Phe Ser Pro Phe
              35                  40                  45

Leu Leu Ser Cys Cys Met Gly Tyr Gly Phe Tyr His Phe Ala Ser Phe
 50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Gln Cys Pro Thr Val Asp Leu Met Leu Pro Met Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr Tyr Arg
            180                 185                 190

Arg Val Glu Glu Thr Tyr Thr Lys Glu Asn Leu Ala Met Val Glu Tyr
            195                 200                 205

Gln Gln Val Phe Asn Ser Ala Pro Arg Asp Met
210                 215

<210> SEQ ID NO 52
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 52

Met Thr Thr Phe Lys Ile Glu Ser Arg Ile His Gly Asn Leu Asn Gly
 1               5                  10                  15

Glu Lys Phe Glu Leu Val Gly Gly Val Gly Glu Gly Arg Leu
             20                  25                  30

Glu Ile Glu Met Lys Thr Lys Asp Lys Pro Leu Ala Phe Ser Pro Phe
              35                  40                  45

Leu Leu Ser Cys Cys Met Gly Tyr Gly Phe Tyr His Phe Ala Ser Phe
 50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Gln Cys Pro Thr Val Asp Leu Met Leu Pro Val Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
        195                 200                 205

Gln Gln Val Phe Asn Ser Ala Pro Arg Asp Met
    210                 215

<210> SEQ ID NO 53
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 53

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Cys Cys Met Gly Tyr Gly Phe Tyr His Phe Ala Ser Phe
    50                  55                  60

Pro Lys Gly Thr Glu Asn Ile Tyr Leu His Ala Ala Thr His Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Arg Gln Cys Pro Thr Val Asp Leu Met Leu Pro Val Ser
    130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
        195                 200                 205

Gln Gln Val Phe Asn Ser Ala Pro Arg Asp Met
    210                 215

<210> SEQ ID NO 54
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 54

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe

-continued

```
                35                  40                  45
Leu Leu Ser Cys Cys Met Gly Tyr Gly Phe Tyr His Phe Ala Ser Phe
 50                  55                  60

Pro Lys Gly Ala Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Gln Cys Pro Thr Val Asp Leu Met Leu Pro Met Ser
                130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
                180                 185                 190

Arg Val Glu Glu Thr His Thr Lys Glu Asn Leu Ala Ile Val Glu Tyr
                195                 200                 205

Gln Gln Val Phe Asn Ser Ala Pro Arg Asp Met
                210                 215
```

<210> SEQ ID NO 55
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 55

```
Met Thr Thr Phe Lys Ile Glu Ser Arg Ile His Gly Asn Leu Asn Gly
  1               5                  10                  15

Glu Lys Phe Glu Leu Val Gly Gly Gly Val Gly Glu Glu Gly Arg Leu
                 20                  25                  30

Glu Ile Glu Met Lys Thr Lys Asp Lys Pro Leu Ala Phe Ser Pro Phe
                 35                  40                  45

Leu Leu Ser Cys Cys Met Gly Tyr Gly Phe Tyr His Phe Ala Ser Phe
 50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Gln Cys Pro Thr Val Asp Leu Met Leu Pro Met Ser
                130                 135                 140

Gly Asn Ile Ile Ala Ser Ser Tyr Ala Leu Ala Phe Gln Leu Arg Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
```

180                 185                 190

Arg Val Glu Glu Thr Tyr Thr Lys Glu Asn Leu Ala Met Val Glu Tyr
        195                 200                 205

Gln Gln Val Phe Asn Ser Ala Pro Arg Asp Met
        210                 215

<210> SEQ ID NO 56
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 56

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
        35                  40                  45

Leu Leu Ser Cys Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Gln Cys Pro Thr Val Asp Leu Met Leu Pro Val Ser
    130                 135                 140

Arg Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
        195                 200                 205

Gln Gln Val Phe Asn Ser Ala Pro Arg Asp Met
        210                 215

<210> SEQ ID NO 57
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 57

Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
        35                  40                  45

```
Leu Leu Ser Cys Cys Met Gly Tyr Gly Phe Tyr His Phe Ala Ser Phe
 50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Gln Cys Pro Thr Val Asp Leu Met Leu Pro Met Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
                180                 185                 190

Arg Val Glu Glu Thr Tyr Thr Lys Glu Asn Leu Ala Met Val Glu Tyr
                195                 200                 205

Gln Gln Val Phe Asn Ser Ala Pro Arg Asp Val
210                 215

<210> SEQ ID NO 58
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 58

Met Thr Thr Phe Lys Ile Glu Ser Arg Ile His Gly Asn Leu Asn Gly
 1               5                  10                  15

Glu Lys Phe Glu Leu Val Gly Gly Val Gly Glu Gly Arg Leu
                 20                  25                  30

Glu Ile Glu Met Lys Thr Lys Asp Lys Pro Leu Ala Phe Ser Pro Phe
                 35                  40                  45

Leu Leu Ser Cys Cys Met Gly Tyr Gly Phe Tyr His Phe Ala Ser Phe
 50                  55                  60

Pro Lys Gly Thr Glu Asn Ile Tyr Leu His Ala Ala Thr His Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
                115                 120                 125

Thr Ile Val Lys Gln Cys Pro Thr Val Asp Leu Met Leu Pro Met Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
                180                 185                 190
```

```
Arg Val Glu Glu Thr Tyr Thr Lys Glu Asn Leu Ala Met Val Glu Tyr
            195                 200                 205

Gln Gln Val Phe Asn Ser Ala Pro Arg Asp Met
        210                 215

<210> SEQ ID NO 59
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 59

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Cys Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Gln Tyr Pro Thr Val Asp Leu Met Leu Pro Met Ser
        130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Ile Val Glu Tyr
        195                 200                 205

Gln Gln Val Phe Asn Ser Ala Pro Arg Asp Met
    210                 215

<210> SEQ ID NO 60
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 60

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Cys Cys Met Gly Tyr Gly Phe Tyr His Phe Ala Ser Phe
    50                  55                  60
```

Pro Lys Gly Thr Glu Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Gln Cys Pro Thr Val Asp Leu Met Leu Pro Met Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
            165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
            195                 200                 205

Gln Gln Val Phe Asn Ser Ala Pro Arg Asp Met
210                 215

<210> SEQ ID NO 61
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 61

Met Thr Thr Phe Lys Ile Glu Ser Arg Ile Gln Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
50                  55                  60

Pro Lys Gly Thr Glu Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Gln Cys Pro Thr Val Asp Leu Met Leu Pro Met Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
            165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
            195                 200                 205

```
Gln Gln Val Phe Asn Ser Ala Pro Arg Asp Met
    210                 215
```

<210> SEQ ID NO 62
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 62

```
Met Thr Thr Phe Lys Ile Glu Ser Arg Ile Gln Gly Asn Leu Asn Gly
1               5                   10                  15

Glu Lys Phe Glu Leu Val Gly Gly Val Gly Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
    50                  55                  60

Pro Lys Gly Thr Glu Asn Ile Tyr Leu His Ala Ala Thr Asn Gly Gly
65                  70                  75                  80

Tyr Thr Asn Thr Arg Lys Glu Ile Tyr Glu Asp Gly Ile Leu Glu
                85                  90                  95

Val Asn Phe Arg Tyr Thr Tyr Glu Phe Asn Lys Ile Ile Gly Asp Val
                100                 105                 110

Glu Cys Ile Gly His Gly Phe Pro Ser Gln Ser Pro Ile Phe Lys Asp
            115                 120                 125

Thr Ile Val Lys Gln Cys Pro Thr Val Asp Leu Met Leu Pro Met Ser
    130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Ile Val Glu Tyr
        195                 200                 205

Gln Gln Val Phe Asn Ser Ala Pro Arg Asp Ile
    210                 215
```

<210> SEQ ID NO 63
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 63

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
    50                  55                  60

Pro Lys Gly Thr Glu Asn Ile Tyr Leu His Ala Ala Thr Asn Gly Gly
```

```
              65                  70                  75                  80
Tyr Thr Asn Thr Arg Lys Glu Ile Tyr Glu Asp Gly Gly Ile Leu Glu
                    85                  90                  95

Val Asn Phe Arg Tyr Thr Tyr Glu Phe Asn Lys Ile Ile Gly Asp Val
                    100                 105                 110

Glu Cys Ile Gly His Gly Phe Pro Ser Gln Ser Pro Ile Phe Lys Asp
                    115                 120                 125

Thr Ile Val Lys Gln Trp Pro Thr Val Asp Leu Met Leu Pro Met Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                    165                 170                 175

Pro Ile His Glu Ser Phe Ser Lys Ser Gly Pro Met Phe Thr His Arg
                    180                 185                 190

Arg Val Glu Glu Thr His Thr Lys Glu Asn Leu Ala Ile Val Glu Tyr
                    195                 200                 205

Gln Gln Val Phe Asn Ser Ala Pro Arg Asp Met
    210                 215
```

<210> SEQ ID NO 64
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 64

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Gly Arg Leu
                    20                  25                  30

Glu Ile Glu Met Lys Thr Lys Asp Lys Pro Leu Ala Phe Ser Pro Phe
                35                  40                  45

Leu Leu Ser Cys Cys Met Gly Tyr Gly Phe Tyr His Phe Ala Ser Phe
50                  55                  60

Pro Lys Gly Thr Glu Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                    85                  90                  95

Val Asn Phe Arg Tyr Thr Tyr Glu Phe Asn Lys Ile Ile Gly Asp Val
                    100                 105                 110

Glu Cys Ile Gly His Gly Phe Pro Ser Gln Ser Pro Ile Phe Lys Asp
                    115                 120                 125

Thr Ile Val Lys Gln Trp Pro Thr Val Asp Leu Met Leu Pro Met Ser
130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                    165                 170                 175

Pro Ile His Glu Ser Phe Ser Lys Ser Gly Pro Met Phe Thr His Arg
                    180                 185                 190

Arg Val Glu Glu Thr His Thr Lys Glu Asn Leu Ala Met Val Glu Tyr
                    195                 200                 205

Gln Gln Val Phe Asn Ser Ala Pro Arg Asp Met
```

```
                210                 215

<210> SEQ ID NO 65
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 65

Met Thr Thr Phe Lys Ile Glu Ser Arg Ile Gln Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Cys Cys Met Gly Tyr Gly Phe Tyr His Phe Ala Ser Phe
    50                  55                  60

Pro Lys Gly Thr Glu Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Lys
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Gln Cys Pro Thr Val Asp Leu Met Leu Pro Met Ser
    130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
        195                 200                 205

Gln Gln Val Phe Asn Ser Ala Pro Arg Asp Met
    210                 215

<210> SEQ ID NO 66
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 66

Met Thr Thr Phe Lys Ile Glu Ser Arg Ile Gln Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Cys Cys Met Gly Tyr Gly Phe Tyr His Phe Ala Ser Phe
    50                  55                  60

Pro Lys Gly Thr Glu Asn Ile Tyr Leu His Ala Ala Thr Asn Gly Gly
65                  70                  75                  80
```

```
Tyr Thr Asn Thr Arg Lys Glu Ile Tyr Glu Asp Gly Gly Ile Leu Glu
            85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Gln Cys Pro Thr Val Asp Leu Met Leu Pro Met Ser
            130                 135                 140

Gly Asn Ile Ile Ala Ser Ser Tyr Ala Leu Ala Phe Gln Leu Glu Asp
145                 150                 155                 160

Gly Ser Phe Tyr Thr Ala Glu Val Lys Asn Asn Ile Asp Phe Lys Asn
            165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
            195                 200                 205

Gln Gln Val Phe Asn Ser Ala Pro Arg Asp Met
            210                 215

<210> SEQ ID NO 67
<211> LENGTH: 219
<212> TYPE: PRT
<213> ORGANISM: Artificial Sequence
<220> FEATURE:
<223> OTHER INFORMATION: Synthetic fluorescent protein

<400> SEQUENCE: 67

Met Thr Thr Phe Lys Ile Glu Ser Arg Ile Arg Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
            35                  40                  45

Leu Leu Ser Cys Cys Met Gly Tyr Gly Phe Tyr His Phe Ala Ser Phe
50                  55                  60

Pro Lys Gly Thr Glu Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
            85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
            115                 120                 125

Thr Ile Val Lys Gln Cys Pro Thr Val Asp Leu Met Leu Pro Met Ser
            130                 135                 140

Gly Asn Ile Ile Ala Ser Ser Tyr Ala Leu Ala Phe Gln Leu Lys Asp
145                 150                 155                 160

Gly Ser Phe Tyr Thr Ala Glu Val Lys Asn Asn Ile Asp Phe Lys Asn
            165                 170                 175

Pro Ile His Glu Ser Phe Ser Lys Ser Gly Pro Met Phe Thr His Arg
            180                 185                 190

Arg Val Glu Glu Thr Tyr Thr Lys Glu Asn Leu Ala Met Val Glu Tyr
            195                 200                 205

Gln Gln Val Phe Asn Ser Ala Pro Arg Asp Met
            210                 215
```

<210> SEQ ID NO 68
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 68

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
aaaccactgg cattctctcc cttcctgctg tccacttgca tgggttacgg gttctaccac   180
ttcgccagct cccaaaggg gactaagaac atctatcttc atgctgcaac aaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagagtt gtcccacggt ggacctgatg   420
ttgccgatgt ccgggaacat catcgccagc tcctacgctt acgccttcca actgaaggac   480
ggctcttct  acacggcaga agtcaagaac aacatagact caagaatcc aatccacgag   540
tccttctcga agtcggggcc catgttcacc cacagacgtg tcgaggagac tcacaccaag   600
gagaaccttg ccatagtgga gtaccagcag gttttcaaca gcgccccaag agacatgtag   660
```

<210> SEQ ID NO 69
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 69

```
atgacaacct tcaaaatcga gtcccggatc cacggcaacc tcaacgggga gaagttcgag    60
ttggttggag gtggagtagg tgaggagggt cgcctcgaga ttgagatgaa gactaaagat   120
aaaccactgg cattctctcc cttcctgctg tccacttgca tgggttacgg gttctaccac   180
ttcgccagct cccaaaggg gactaagaac atctatcttc atgctgcaac gaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagagtt gtcccacggt ggacctgatg   420
ttgccgatgt ccgggaacat catcgccagc tcctacgctt acgccttcca actgaaggac   480
ggctcttct  acacggcaga agtcaagaac aacatagact caagaatcc aatccacgag   540
tccttctcga agtcggggcc catgttcacc cacagacgtg tcgaggagac tctcaccaag   600
gagaaccttg ccatagtgga gtaccagcag gttttcaaca gcgccccaag agacatgtag   660
```

<210> SEQ ID NO 70
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 70

```
atgacaacct tcaaaatcga gtcccggatc cacggcaacc tcaacgggga gaagttcgag    60
ttggttggag gtggagtagg tgaggagggt cgcctcgaga ttgagatgaa gactaaagat   120
aaaccactgg cattctctcc cttcctgctg tccacttgca tgggttacgg gttctaccac   180
```

```
ttcgccagct tcccaaaggg gactaagaac atctatcttc atgctgcaac gaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagtt gtcccacggt ggacctgatg    420
ttgccgatgt ccgggaacat catcgccagc tcctacgctt acgccttcca actgaaggac    480 ggctcttttct acacggcaga agtcaagaac aacatagact tcaagaatcc aatccacgag    540
tccttcttga agtcggggcc catgttcacc cacagacgtg tcgaggagac tctcaccaag    600
gagaaccttg ccatagtgga gtaccagcag gttttcaaca gcgccccaag agacatgtag    660
```

<210> SEQ ID NO 71
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 71

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
aaaccactgg cattctctcc cttcctgctg tccacttgca tgggttacgg gttctaccac    180
ttcgccagct tcccaaaggg gactaagaac atctatcttc atgctgcaac gaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagtt gtcccacggt ggacctgatg    420
ttgccgatgc ccgggaacat catcgccagc tcctacgctt acgccttcca actgaaggac    480 ggctcttttct acacggcaga agtcaagaac aacatagact tcaagaatcc aatccacgag    540
tccttctcga agtcggggcc catgttcacc cacagacgtg tcgaggagac tctcaccaag    600
gagaaccttg ccatagtgga gtaccagcag gttttcaaca gcgccccaag agacatgtag    660
```

<210> SEQ ID NO 72
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 72

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
aaaccactgg cattctctcc cttcctgctg tccacttgca tgggttacgg gttctaccac    180
ttcgccagct tcccaaaggg gattaagaac atctatcttc atgctgcaac gaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagtt gtcccacggt ggacctgatg    420
ttgccaatgt ccgggaacat catcgccagc tcctacgctt acgccttcca actgaaggac    480 ggctcttttct acacggcaga agtcaagaac aacatagact tcaagaatcc aatccacgag    540
tccttctcga agtcagggcc catgttcacc cacagacgtg tcgaggagac tctcaccaag    600
```

```
gagaaccttg ccatagtgga gtaccagcag gttttcaaca gcgccccaag agacatgtag    660
```

<210> SEQ ID NO 73
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 73

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
aaaccactgg cattctctcc cttcctgctg accacttgca tgggttacgg gttctaccac    180
ttcgccagct cccaaaggg gactaagaac atctatcttc atgctgcaac gaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagtt gtcccacggt ggacctgatg    420
ttgccgatgt ccgggaacat catcgccagc tcctacgctt acgccttcca actgaaggac    480
ggctcttttct acacggcaga agtcaagaac aacatagact tcaagaatcc aatccacgag    540
tccttctcga gtcggggcc catgttcacc cacagacgtg tcgaggagac tctcaccaag    600
gagaaccttg ccatagtgga gtaccagcag gttttcaaca gcgccccaag agacatgtag    660
```

<210> SEQ ID NO 74
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 74

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
aaaccactgg cattctctcc cttcctgctg tccacttgca tgggttacgg gttctaccac    180
ttcgccagct cccaaagggg gactaagaac atctatcttc atgctgcaac gaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagagtt gtcccacggt ggacctgatg    420
ttgccgatgt ccgggaacat catcgtcagc tcctacgctt acgccttcca actgaaggac    480
ggctcttttct acacggcaga agtcaagaac aacatagact tcaagaatcc aatccacgag    540
tccttctcga gtcggggcc catgttcacc cacagacgtg tcgaggagac tctcaccaag    600
gagaaccttg ccatagtgga gtaccagcag gttttcaaca gcgccccaag agacatgtag    660
```

<210> SEQ ID NO 75
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 75

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
```

```
aaaccactgg cattctctcc cttcctgctg tccacttgca tgggttacgg gttctaccac      180
ttcgccagct tcccaaaggg gactaagaac atctatcttc atgctgcaac gaacggaggt      240
tacaccaaca cccggaagga gatctatgaa gacggcggca tcttggaggt caacttccgt      300
tacacttacg agttcaacaa gatcatcggt gacgtcgagt gcattggaca tggattcccg      360
agtcagagtc cgatcttcaa ggacacgatc gtgaagagtt gtcccacggt ggacctgatg      420
ttgccgatga ccgggaacat catcaccagc tcctacgctt acgccttcca actgaaggac      480
ggctctttct acacggcgga agtcaagaac aacatagact tcaagaatcc aatccacgag      540
tccttctcga gtcggggcc  catgttcacc cacagacgtg tcgaggagac tctcaccaag      600
gagaaccttg ccatagtgga gtaccagcag gttttcaaca gcgccccaag agacatgtag      660
```

<210> SEQ ID NO 76
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 76

```
atgacaacct tcaaaatcga gtcccggatc cacggcaacc tcaacgggga gaagttcgag       60
ttggttggag gtggagtagg tgaggagggt cgcctcgaga ttgagatgag gactaaagat      120
aaaccactgg cattctctcc cttcctgctg tccacttgca tgggttacgg gttctaccac      180
ttcgccagct tcccaaaggg gactaagaac atctatcttc atgctgcaac gaacggaggt      240
tacaccaaca ccaggaagga gatctatgaa gacggcggca tcttggaggt caacttccgt      300
tacacttacg agttcaacaa gatcatcggt gacgtcgagt gcattggaca tggattccca      360
agtcagagtc cgatcttcaa ggacacgatc gtgaagagtt gtcccacggt ggacctgatg      420
ttgccgatgt ccgggaacat catcgtcagc tcctacgctt acgccttcca actgaaggac      480
ggcactttct acacggcaga agtcaagaac aacatagact tcaagaatcc aatccacgag      540
tccttctcga gtcggggcc  catgttcacc cacagacgtg tcgaggagac tctcaccaag      600
gagaaccttg ccatagtgga gtaccagcag gttttcaaca gcgccccaag agacatgtag      660
```

<210> SEQ ID NO 77
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 77

```
atgacaacct tcaaaatcga gtcccggatc cacggcaacc tcaacgggga ggagttcgag       60
ttggttggag gtggagtagg tgaggagggt cgcctcgaga ttgagatgaa gactaaagat      120
aaaccactgg cattctctcc cttcctgctg tccacttgca tgggttacgg gttctaccac      180
ttcgccagct tcccaaaggg gactaagaac atctatcttc atgctgcaac gaacggaggt      240
tacaccaaca ccaggaagga gatctatgaa gacggcggca tcttggaggt caacttccgt      300
tacacttacg agttcaacaa gatcatcggt gacgtcgagt gcattggaca tggattccca      360
agtcagagtc cgatcttcaa ggacacgatc gtgaagagtt gtcccacggt ggacctgatg      420
ttgccgatgc ccgggaacat catcgccagc tcctacgctt acgccttcca actgaaggac      480
ggctctttct acacggcaga agtcaagaac aacatagact tcaagaatcc aatccacgag      540
```

| | |
|---|---|
| tccttctcga agtcggggcc catgttcacc cacagacgtg tcgaggagac tctcaccaag | 600 |
| gagaaccttg ccatagtgga gtaccagcag gttttcaaca gcgccccaag agacatgtag | 660 |

<210> SEQ ID NO 78
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 78

| | |
|---|---|
| atgacaacct tcaaaatcga gtcccggatc cacggcaacc tcaacgggga ggagttcgag | 60 |
| ttggttggag gtggagtagg tgaggagggt cgcctcgaga ttgagatgaa gactaaagat | 120 |
| aaaccactgg cattctctcc cttcctgctg tccacttgca tgggttacgg gttctaccac | 180 |
| ttcgccagct tcccaaaggg gattaagaac atctatcttc atgctgcaac gaacggaggt | 240 |
| tacaccaaca ccaggaagga gatctatgaa gacggcggca tcttggaggt caacttccgt | 300 |
| tacacttacg agttcaacaa gatcatcggt gacgtcgagt gcattggaca tggattccca | 360 |
| agtcagagtc cgatcttcaa ggacacaatc gtgaagagtt gtcccacggt ggacctgatg | 420 |
| ttgccgatgt ccgggaacat catcgccagc tcctacgctt acgccttcca actgaaggac | 480 |
| ggctcttttct acacggcaga agtcaagaac aacatagact tcaggaatcc aatccacgag | 540 |
| tccttctcga agtcggggcc catgttcacc cacagacgtg tcgaggagac tctcaccaag | 600 |
| gagaaccttg ccatagtgga gtaccagcag gttttcaaca gcgccccaag agacatgtag | 660 |

<210> SEQ ID NO 79
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 79

| | |
|---|---|
| atgacaacct tcaaaatcga gtcccggatc cacggcaacc tcaacgggga gaagttcgag | 60 |
| ttggttggag gtggagtagg tgaggagggt cgcctcgaga ttgagatgaa gactaaagat | 120 |
| aaaccactgg cattctctcc cttcctgctg tccacttgca tgggttacgg gttctaccac | 180 |
| ttcgccagct tcccaaaggg gattaagaac atctatcttc atgctgcaac gaacggaggt | 240 |
| tacaccaaca ccaggaagga gatctatgaa gacggcggcg tcttggaggt caacttccgt | 300 |
| tacacttacg agttcgacaa gatcatcggt gacgtcgagt gcattggaca tggattccca | 360 |
| agtcagagtc cgatcttcaa ggacacgatc gtgaagagtt gtcccacggt ggacctgatg | 420 |
| ttgccgatgt ccgggaacat catcgccagc tcctacgctt acgccttcca actgaaggac | 480 |
| ggctcttttct acacggcaga agtcaagaac aacatagact tcaagaatcc aatccacgag | 540 |
| tccttctcga agtcggggcc catgttcacc cacagacgtg tcgaggagac tctcaccaag | 600 |
| gagaaccttg ccatagtgga gtaccagcag gttttcaaca gcgccccaag ggacatgtag | 660 |

<210> SEQ ID NO 80
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 80

| | |
|---|---|
| atgacaacct tcaaaatcga gtcccggatc cacggcaacc tcaacgggga gaagttcgag | 60 |

```
ttggttggag gtggagtagg tgaggagggt cgcctcgaga ttgagatgaa gactaaagat      120
aaaccactgg cattctctcc cttcctgctg tccacttgca tgggttacgg gttctaccac      180
ttcgccagct tcccaaaggg gactaagaac atctatcttc atgctgcaac gaacggaggt      240
tacaccaaca ccaggaagga gatctatgaa gacggcggca tcttggaggt caacttccgt      300
tacacttacg agttcgacaa gatcatcggt gacgtcgagt gcattggaca tggattccca      360
agtcagagtc cgatcttcaa ggacacgatc gtgaagagtt gtcccacggt ggacctgatg      420
ttgccgatgt ccgggaacat catcgccagc tcctacgctt acgccttcca actgaaggac      480 ggctcttttct acacggcaga gtcaagaac aacatagact tcaagaatcc aatccacgag      540
tccttcttga agtcggggcc catgttcacc cacagacgtg tcgaggagac tctcaccaag      600
gagaaccttg ccatagtgga gtaccagcag gttttcaaca gcgccccaag agacatgtag      660
```

<210> SEQ ID NO 81
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 81

```
atgacaacct tcaaaatcga gtcccggatc cacggcaacc tcaacgggga gaagttcgag       60
ttggttggag gtggagtagg tgaggagggt cgcctcgaga tagagatgaa gactaaagat      120
aaaccactgg cattctctcc cttcctgttg tccactagca tgggttacgg gttctaccac      180
ttcgccagct tcccaaaggg gactaagaac atctatcttc atgctgcaac gaacggaggt      240
tacaccaaca ccaggaagga gatctatgaa gacggcggca tcttggaggt caacttccgt      300
tacacttacg agttcaacaa gatcatcggt gatgtcgagt gcattggaca tggattccca      360
agtcagagtc cgatcttcaa ggacacgatc gtgaagagtt gtcccacggt ggacctgatg      420
ttgccgatgt ccgggaacat catcgccagc tcctacgctt acgccttcca actgaaggac      480 ggctcttttct acacggcaga tgtcaagaac aacatagact tcaagaatcc aatccacgag      540
tccttctcga agtcggggcc catgttcacc cacagacgtg tcgaggagac tctcaccaag      600
gagaaccttg ccatagtgga gtaccagcag gttttcaaca gcgccccaag agacatgtag      660
```

<210> SEQ ID NO 82
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 82

```
atgacaacct tcaaaatcga gtcccggatc cacggcaacc tcaacgggga gaagttcgag       60
ttggttggag gtggagtagg tgaggagggt cgcctcgaga ttgagatgaa gactaaagat      120
aaaccactgg cattctctcc cttcctgctg accacttgca tgggttacgg gttctaccac      180
ttcgccagct tcccaaaggg gattaagaac atctatcttc atgctgcaac gaacggaggt      240
tacaccaaca ccaggaagga gatctatgaa gacggcggca tcttggaggt caacttccgt      300
tacacttacg agttcaacaa gatcatcggt gacgtcgagt gcattggaca tggattccca      360
agtcagagtc cgatcttcaa ggacacgatc gtgaagagtt gtcccacggt ggacctgatg      420
ttgccaatgt ccgggaacat catcgccagc tcctacgctt acgccttcca actgaaggac      480
```

```
ggctctttct acacggcaga agtcaagaac aacatagact tcaagaatcc aatccacgag    540
tccttctcga gtcagggcc catgttcacc cacagacgtg tcgaggagac tctcaccaag     600
gagaaccttg ccatagtgga gtaccagcag gttttcaaca gcgccccaag agacatgtag   660
```

<210> SEQ ID NO 83
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 83

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
aaaccactgg cattctctcc cttcctgctg tcctgctgca tgggttacgg gttctaccac    180
ttcgccagct cccaaaggg gactaagaac atctatcttc atgctgcaac aaacggaggt     240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagcaat gtcccacggt ggacctgatg    420
ttgccgatgt ccgggaacat catcgccagc tcctacgctt tggccttcca actgaaggac    480
ggctctttct acacggcaga agtcaagaac aacatagact tcaagaatcc aatccacgag    540
tccttctcga gtcggggcc catgttcacc cacagacgtg tcgaggagac ttacaccaag     600
gagaaccttg ccatggtgga gtaccagcag gttttcaaca gcgccccaag agacatgtag   660
```

<210> SEQ ID NO 84
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 84

```
atgacaacct tcaaaatcga gtcccggatc cgtggcaacc tcaacgggga gaagttcgag     60
ttggttggag gtggagtagg tgaggagggt cgcctcgaga ttgagatgaa gactaaagat    120
aaaccactgg cattctctcc cttcctgctg tcctgctgca tgggttacgg gttctaccac    180
ttcgccagct cccaaaggg gactaagaac atctatcttc atgctgcaac aaacggaggt     240
tacaccaaca ccaggaagga gatctatgaa gacggcggca tcttggaggt caacttccgt    300
tacacttacg agctcaacaa gatcatcggt gacgtcgagt gcattggaca tggattccca    360
agtcagagtc cgatcttcaa ggacacgatc gtgaagcaat gtcccacggt ggacctgatg    420
ttgccgatgt ccgggaacat catcgccagc tcctacgctt tggccttccg actgaaggac    480
ggctctttct acacggcaga agtcaagaac aacatagact tcaagaatcc aatccacgag    540
tccttctcga gtcggggcc catgttcacc cacagacgtg tcgaggagac ttacaccaag     600
gagaaccttg ccatggtgga gtaccagcag gttttcaaca gcgccccaag agacatgtag   660
```

<210> SEQ ID NO 85
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 85

```
atgacaacct tcaaaatcga gtcccggatc cacggcaacc tcaacgggga gaagttcgag    60
ttggttggag gtggagtagg tgaggagggt cgcctcgaga ttgagatgaa gactaaagat    120
aaaccactgg cattctctcc cttcctgctg tcctgctgca tgggttacgg gttctaccac   180
ttcgccagct tcccaaaggg gactaagaac atctatcttc atgctgcaac aaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagcaat gtcccacggt ggacctgatg   420
ttgccgatgt ccgggaacat catcgccagc tcctacgctt tggccttcca actgaaggac   480
ggctctttct acacggcaga agtcaagaac aacatagact tcaagaatcc aatccacgag   540
tccttctcga gtcggggcc catgttcacc tacagacgtg tcgaggagac ttacaccaag    600
gagaaccttg ccatggtgga gtaccagcag gttttcaaca gcgccccaag agacatgtag   660
```

<210> SEQ ID NO 86
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 86

```
atgacaacct tcaaaatcga gtcccggatc catggcaacc tcaacgggga gaagttcgag    60
ttggttggag gtggagtagg tgaggagggt cgcctcgaga ttgagatgaa gactaaagat   120
aaaccactgg cattctctcc cttcctgctg tcctgctgca tgggttacgg gttctaccac   180
ttcgccagct tcccaaaggg gactaagaac atctatcttc atgctgcaac aaacggaggt   240
tacactaaca ccaggaagga gatctatgaa gacggcggca tcttggaggt caacttccgt   300
tacacttacg agttcaacaa gatcatcggt gacgtcgagt gcattgggca tggattccca   360
agtcagagtc cgatcttcaa ggacacgatc gtgaagcaat gtcccacggt ggacctgatg   420
ttgccggtgt ccgggaacat catcgccagc tcctacgctt tggccttcca actgaaggac   480
ggctctttct acacggcaga agtcaagaac aacatagact tcaagaatcc aatccacgag   540
tccttctcga gtcggggcc catgttcacc cacagacgtg tcgaggagac ttacaccaag    600
gagaaccttg ccatggtgga gtaccagcag gttttcaaca gcgccccaag agacatgtag   660
```

<210> SEQ ID NO 87
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 87

```
atgacaacct tcaaaatcga gtcccggatc cacggcaacc tcaacgggga gaagttcgag    60
ttggttggag gtggagtagg tgaggagggt cgcctcgaga ttgagatgaa gactaaagat   120
aaaccactgg cattctctcc cttcctgctg tcctgctgca tgggttacgg gttctaccac   180
ttcgccagct tcccaaaggg gactgagaac atctatcttc atgctgcaac acacggaggt   240
tacaccaaca ccaggaagga gatctatgaa gacggcggca tcttggaggt caacttccgt   300
tacacttacg agttcaacaa gatcatcggt gacgtcgagt gcattgggca tggattccca   360
agtcagagtc cgatcttcaa ggacacgatc gtgaggcaat gtcccacggt ggacctgatg   420
```

```
ttgccggtgt ccgggaacat catcgccagc tcctacgctt tggccttcca actgaaggac    480
ggctctttct acacggcaga agtcaagaac aacatagact tcaagaatcc aatccacgag    540
tccttctcga agtcggggcc catgttcacc cacagacgtg tcgaggagac ttacaccaag    600
gagaaccttg ccatggtgga gtaccagcag gtcttcaaca gcgccccaag agacatgtag    660
```

<210> SEQ ID NO 88
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 88

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
aaaccactgg cattctctcc cttcctgctg tcctgctgca tgggttacgg gttctaccac    180
ttcgccagct tcccaaaggg ggctaagaac atctatctcc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagcaat gtcccacggt ggacctgatg    420
ttgccgatgt ccgggaacat catcgccagc tcctacgctt tggccttcca actgaaggac    480
ggctctttct acacggcaga agtcaagaac aacatagact tcaagaatcc aatccacgag    540
tccttctcga agtcggggcc catgttcacc cacagacgtg tcgaggagac tcacaccaag    600
gagaaccttg ccatagtgga gtaccagcag gttttcaaca gcgccccaag agacatgtag    660
```

<210> SEQ ID NO 89
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 89

```
atgacaacct tcaaaatcga gtcccggatc cacggcaacc tcaacgggga gaagttcgag     60
ttggttggag gtggagtagg tgaggagggt cgcctcgaga ttgagatgaa gactaaagat    120
aaaccactgg cattctctcc cttcctgctg tcctgctgca tgggttacgg gttctaccac    180
ttcgccagct tcccaaaggg gactaagaac atctatcttc atgctgcaac aaacggaggt    240
tacaccaaca ccaggaagga gatctatgaa gacggcggca tcttggaggt caacttccgt    300
tacacttacg agttcaacaa gatcatcggt gacgtcgagt gcattggaca tggattccca    360
agtcagagtc cgatcttcaa ggacacgatc gtgaagcaat gtcccacggt ggacctgatg    420
ttgccgatgt ccgggaacat catcgccagc tcctacgctt tggccttcca actgagggac    480
ggctctttct acacggcaga agtcaagaac aacatagact tcaagaatcc aatccacgag    540
tccttctcga agtcggggcc catgttcacc cacagacgtg tcgaggagac ttacaccaag    600
gagaaccttg ccatggtgga gtaccagcag gttttcaaca gcgccccaag agacatgtag    660
```

<210> SEQ ID NO 90
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 90

```
atgacaacct tcaaaatcga gtcccggatc cacggcaacc tcaacgggga gaagttcgag      60
ttggttggag gtggagtagg tgaggagggt cgcctcgaga ttgagatgaa gactaaagat     120
aaaccactgg cattctctcc cttcctgctg tcctgctgca tgggttacgg gttctaccac     180
ttcgccagct tcccaaaggg gactaagaac atctatcttc atgctgcaac aaacggaggt     240
tacaccaaca ccaggaagga gatctatgaa gacggcggca tcttggaggt caacttccgt     300
tacacttacg agttcaacaa gatcatcggt gacgtcgagt gcattggaca tggattccca     360
agtcagagtc cgatcttcaa ggacacgatc gtgaagcaat gtccacggt ggacctgatg      420
ttgccggtgt ccaggaacat catcgccagc tcctacgctt tggccttcca actgaaggac     480
ggctcttttct acacggcaga agtcaagaac aacatagact tcaagaatcc aatccacgag    540
tccttctcga gtcggggcc catgttcacc cacagacgtg tcgaggagac ttacaccaag      600
gagaaccttg ccatggtgga gtaccagcag gttttcaaca gcgccccaag agacatgtag     660
```

<210> SEQ ID NO 91
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 91

```
atgacaacct tcaaaatcga gtcccggatc cacggcaacc tcaacgggga gaagttcgag      60
ttggttggag gtggagtagg tgaggagggt cgcctcgaga ttgagatgaa gactaaagat     120
aaaccactgg cattctctcc cttcctgctg tcctgctgca tgggttacgg gttctaccac     180
ttcgccagct tcccaaaggg gactaagaac atctatcttc atgctgcaac aaacggaggt     240
tacaccaaca ccaggaagga gatctatgaa gacggcggca tcttggaggt caacttccgt     300
tacacttacg agttcaacaa gatcatcggt gacgtcgagt gcattggaca tggattccca     360
agtcagagtc cgatcttcaa ggacacgatc gtgaagcaat gtccacggt ggacctgatg      420
ttgccgatgt ccgggaacat catcgccagc tcctacgctt tggccttcca actgaaggac     480
ggctcttttct acacggcaga agtcaagaac aacatagact tcaagaatcc aatccacgag    540
tccttctcga gtcggggcc catgttcacc cacagacgtg tcgaggagac ttacaccaag      600
gagaaccttg ccatggtgga gtaccagcag gttttcaaca gcgccccaag agacgtgtag     660
```

<210> SEQ ID NO 92
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 92

```
atgacaacct tcaaaatcga gtcccggatc catggcaacc tcaacgggga gaagttcgag      60
ttggttggag gtggagtagg tgaggagggt cgcctcgaga ttgagatgaa gactaaagat     120
aaaccactgg cattctctcc cttcctgctg tcctgctgca tgggttacgg gttctaccac     180
ttcgccagct tcccaaaggg gactgagaac atctatcttc atgctgcaac acacggaggt     240
tacactaaca ccaggaagga gatctatgaa gacggcggca tcttggaggt caacttccgt     300
tacacttacg agttcaacaa gatcatcggt gacgtcgagt gcattggaca tggattccca     360
```

| agtcagagtc cgatcttcaa ggacacgatc gtgaagcaat gtcccacggt ggacctgatg | 420 |
| ttgccgatgt ccgggaacat catcgccagc tcctacgctt tggccttcca actgaaggac | 480 |
| ggctctttct acacggcaga agtcaagaac aacatagact tcaagaatcc aatccacgag | 540 |
| tccttctcga agtcggggcc catgttcacc cacagacgtg tcgaggagac ttacaccaag | 600 |
| gagaaccttg ccatggtgga gtaccagcag gttttcaaca gcgccccaag agacatgtag | 660 |

<210> SEQ ID NO 93
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 93

| atgacaacct tcaaaatcga gtcccggatc cacggcaacc tcaacgggga gaagttcgag | 60 |
| ttggttggag gtggagtagg tgaggagggt cgcctcgaga ttgagatgaa gactaaagat | 120 |
| aaaccactgg cattctctcc cttcctgctg tcctgctgca tgggttacgg gttctaccac | 180 |
| ttcgccagct tcccaaaggg gactaagaac atctatcttc atgctgcaac aaacggaggt | 240 |
| tacaccaaca ccaggaagga gatctatgaa gacggcggca tcttggaggt caacttccgt | 300 |
| tacacttacg agttcaacaa gatcatcggt gacgtcgagt gcattggaca tggattccca | 360 |
| agtcagagtc cgatcttcaa ggacacgatc gtgaagcaat atcccacggt ggacctgatg | 420 |
| ttgccgatgt ccgggaacat catcgccagc tcctacgctt tggccttcca actgaaggac | 480 |
| ggctctttct acacggcaga agtcaagaac aacatagact tcaagaatcc aatccacgag | 540 |
| tccttctcga agtcggggcc catgttcacc cacagacgtg tcgaggagac tcacaccaag | 600 |
| gagaaccttg ccatagtgga gtaccagcag gttttcaaca gcgccccaag agacatgtag | 660 |

<210> SEQ ID NO 94
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 94

| atgacaacct tcaaaatcga gtcccggatc cacggcaacc tcaacgggga gaagttcgag | 60 |
| ttggttggag gtggagtagg tgaggagggt cgcctcgaga ttgagatgaa gactaaagat | 120 |
| aaaccactgg cattctctcc cttcctgctg tcctgctgca tgggttacgg gttctaccac | 180 |
| ttcgccagct tcccaaaggg gactgagaac atctatcttc atgctgcaac aaacggaggt | 240 |
| tacaccaaca ccaggaagga gatctatgaa gacggcggca tcttggaggt caacttccgt | 300 |
| tacacttacg agttcaacaa gatcatcggt gacgtcgagt gcattggaca tggattccca | 360 |
| agtcagagtc cgatcttcaa ggacacgatc gtgaagcaat gtcccacggt ggacctgatg | 420 |
| ttgccgatgt ccgggaacat catcgccagc tcctacgctt tggccttcca actgaaggac | 480 |
| ggctctttct acacggcaga agtcaagaac aacatagact tcaagaatcc aatccacgag | 540 |
| tccttctcga agtcggggcc catgttcacc cacagacgtg tcgaggagac ttacaccaag | 600 |
| gagaaccttg ccatggtgga gtaccagcag gttttcaaca gcgccccaag agacatgtag | 660 |

<210> SEQ ID NO 95
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 95

```
atgacaacct tcaaaatcga gtcccggatc caaggcaacc tcaacgggga gaagttcgag    60
ttggttggag gtggagtagg tgaggagggt cgcctcgaga ttgagatgaa gactaaagat   120
aaaccactgg cattctctcc cttcctgctg tcctgctgca tgggttacgg gttctaccac   180
ttcgccagct tcccaaaggg gactgagaac atctatcttc atgctgcaac aaacggaggt   240
tacaccaaca ccaggaagga gatctatgaa gacggcggca tcttggaggt caacttccgt   300
tacacttacg agttcaacaa gatcatcggt gacgtcgagt gcattggaca tggattccca   360
agtcagagtc cgatcttcaa ggacacgatc gtgaagcaat gtcccacggt ggacctgatg   420
ttgccgatgt ccgggaacat catcgccagc tcctacgctt tggccttcca actgaaggac   480
ggctcttttct acacggcaga agtcaagaac aacatagact tcaagaatcc aatccacgag   540
tccttctcga gtcggggcc catgttcacc cacagacgtg tcgaggagac ttacaccaag   600
gagaaccttg ccatggtgga gtaccagcag gttttcaaca gcgccccaag agacatgtag   660
```

<210> SEQ ID NO 96
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 96

```
atgacaacct tcaaaatcga gtcccggatc caaggcaacc tcaacgggga gaagttcgag    60
ttggttggag gtggagtagg tgaggagggt cgcctcgaga ttgagatgaa gactaaagat   120
aaaccactgg cattctctcc cttcctgctg tcctgctgca tgggttacgg gttctaccac   180
ttcgccagct tcccaaaggg gactgagaac atctatcttc atgctgcaac aaacggaggt   240
tacaccaaca ccaggaagga gatctatgaa gacggcggca tcttggaggt taacttccgt   300
tacacttacg agttcaacaa gatcatcggt gacgtcgagt gcattggaca tggattccca   360
agtcagagtc cgatcttcaa ggacacgatc gtgaagcaat gtcccacggt ggacctgatg   420
ttgccgatgt ccgggaacat catcgccagc tcctacgctt tggccttcca actgaaggac   480
ggctcttttct acacggcaga agtcaagaac aacatagact tcaagaatcc aatccacgag   540
tccttctcga gtcggggcc catgttcacc cacagacgtg tcgaggagac tcacaccaag   600
gagaaccttg ccatagtgga gtaccagcag gttttcaaca gcgccccaag agacatatag   660
```

<210> SEQ ID NO 97
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 97

```
atgacaacct tcaaaatcga gtcccggatc cacggcaacc tcaacgggga gaagttcgag    60
ttggttggag gtggagtagg tgaggagggt cgcctcgaga ttgagatgaa gactaaagat   120
aaaccactgg cattctctcc cttcctgctg tcctgctgca tgggttacgg gttctaccac   180
ttcgccagct tcccaaaggg gactgagaac atctatcttc atgctgcaac aaacggaggt   240
tacaccaaca ccaggaagga gatctatgaa gacggcggca tcttggaggt caacttccgt   300
```

```
tacacttacg agttcaacaa gatcatcggt gacgtcgagt gcattggaca tggattccca      360
agtcagagtc cgatcttcaa ggacacgatc gtgaagcaat ggcccacggt ggacctgatg      420
ttgccgatgt ccgggaacat catcgccagt cctacgctt tggccttcca actgaaggac       480
ggctctttct acacggcaga ggtcaagaac aacatagact caagaatcc aatccacgag       540 tccttctcga agtcggggcc catgttcacc cacagacgtg tcgaggagac tcacaccaag      600
gagaaccttg ccatagtgga gtaccagcag gttttcaaca gcgccccaag agacatgtag      660
```

<210> SEQ ID NO 98
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 98

```
atgacaacct tcaaaatcga gtcccggatc cacggcaacc tcaacgggga gaagttcgag       60
ttggttggag gtggagtagg tgaggagggt cgcctcgaga ttgagatgaa gactaaagat      120
aaaccactgg cattctctcc cttcctgctg tcctgctgca tgggttacgg gttctaccac      180
ttcgccagct tcccaaaggg gactgagaac atctatcttc atgctgcaac aaacggaggt      240
tacaccaaca ccaggaagga gatctatgaa gacggcggca tcttggaggt caacttccgt      300
tacacttacg agttcaacaa gatcatcggt gacgtcgagt gcattggaca tggattccca      360
agtcagagtc cgatcttcaa ggacacgatc gtgaagcaat ggcccacggt ggacctgatg      420
ttgccgatgt ccgggaacat catcgccagt cctacgctt tggccttcca actgaaggac       480
ggctctttct acacggcaga ggtcaagaac aacatagact caagaatcc aatccacgag       540 tccttctcga agtcggggcc catgttcacc cacagacgtg tcgaggagac tcacaccaag      600
gagaaccttg ccatggtgga gtaccagcag gttttcaaca gcgccccaag agacatgtag      660
```

<210> SEQ ID NO 99
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 99

```
atgacaacct tcaaaatcga gtcccggatc caaggcaacc tcaacgggga gaagttcgag       60
ttggttggag gtggagtagg tgaggagggt cgcctcgaga ttgagatgaa gaccaaagat      120
aaaccactgg cattctctcc cttcctgctg tcctgctgca tgggttacgg gttctaccac      180
ttcgccagct tcccaaaggg gactgagaac atctatcttc atgctgcaac aaacggaggt      240
tacaccaaca ccaggaagga gatctatgaa gacggcggca tcttgaaggt caacttccgt      300
tacacttacg agttcaacaa gatcatcggt gacgtcgagt gcattggaca tggattccca      360
agtcagagtc cgatcttcaa ggacacgatc gtgaagcaat gtcccacggt ggacctgatg      420
ttgccgatgt ccgggaacat catcgccagc cctacgctt tggccttcca actgaaggac       480
ggctctttct acacggcaga agtcaagaac aacatagact caagaatcc aatccacgag       540 tccttctcga agtcggggcc catgttcacc cacagacgtg tcgaggagac ttacaccaag      600
gagaaccttg ccatggtgga gtaccagcag gttttcaaca gcgccccaag agacatgtag      660
```

<210> SEQ ID NO 100
<211> LENGTH: 660

<212> TYPE: DNA
<213> ORGANISM: Artificial Sequence
<220> FEATURE:
<223> OTHER INFORMATION: Synthetic oligonucleotide

<400> SEQUENCE: 100

```
atgacaacct tcaaaatcga gtcccggatc caaggcaacc tcaacgggga gaagttcgag      60
ttggttggag gtggagtagg tgaggagggt cgcctcgaga ttgagatgaa gactaaagat     120
aaaccactgg cattctctcc cttcctgctg tcctgctgca tgggttacgg gttctaccac     180
ttcgccagct tcccaaaggg gactgagaac atctatcttc atgctgcaac aaacggaggt     240
tacaccaaca ccaggaagga gatctatgaa gacggcggca tcttggaggt caacttccgt     300
tacacttacg agttcaacaa gatcatcggt gacgtcgagt gcattggaca tggattccca     360
agtcagagtc cgatcttcaa ggacacgatc gtgaagcaat gtcccacggt ggacctgatg     420
ttgccgatgt ccgggaacat catcgccagc tcctacgctt tggccttcca actggaggac     480
ggctctttct acacggcaga agtcaagaac aacatagact tcaagaatcc aatccacgag     540
tccttctcga gtcggggcc catgttcacc cacagacgtg tcgaggagac ttacaccaag     600
gagaaccttg ccatggtgga gtaccagcag gttttcaaca gcgccccaag agacatgtag     660
```

<210> SEQ ID NO 101
<211> LENGTH: 660
<212> TYPE: DNA
<213> ORGANISM: Artificial Sequence
<220> FEATURE:
<223> OTHER INFORMATION: Synthetic oligonucleotide

<400> SEQUENCE: 101

```
atgacaacct tcaaaatcga gtcccggatc cgtggcaacc tcaacgggga gaagttcgag      60
ttggttggag gtggagtagg tgaggagggt cgcctcgaga ttgagatgaa gactaaagat     120
aaaccactgg cattctctcc cttcctgctg tcctgctgca tgggttacgg gttctaccac     180
ttcgccagct tcccaaaggg gactgagaac atctatcttc atgctgcaac aaacggaggt     240
tacaccaaca ccaggaagga gatctatgaa gacggcggca tcttggaggt caacttccgt     300
tacacttacg agttcaacaa gatcatcggt gacgtcgagt gcattggaca tggattccca     360
agtcagagtc cgatcttcaa ggacacgatc gtgaagcaat gtcccacggt ggacctgatg     420
ttgccgatgt ccgggaacat catcgccagc tcctacgctt tggccttcca actgaaggac     480
ggctctttct acacggcaga agtcaagaac aacatagact tcaagaatcc aatccacgag     540
tccttctcga gtcggggcc catgttcacc cacagacgtg tcgaggagac ttacaccaag     600
gagaaccttg ccatggtgga gtaccagcag gttttcaaca gcgccccaag agacatgtag     660
```

<210> SEQ ID NO 102
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 102

```
atgcttccgg ctcgtatgtt g                                                21
```

<210> SEQ ID NO 103
<211> LENGTH: 20
<212> TYPE: DNA
<213> ORGANISM: Artificial Sequence
<220> FEATURE:

<223> OTHER INFORMATION: Synthetic oligonucleotide primer

<400> SEQUENCE: 103

| gtacggccga ctagtaggcc | 20 |

<210> SEQ ID NO 104
<211> LENGTH: 729
<212> TYPE: DNA
<213> ORGANISM: Artificial Sequence
<220> FEATURE:
<223> OTHER INFORMATION: Synthetic oligonucleotide

<400> SEQUENCE: 104

| tctagatgca tcatcatcat catcatggcg gcagcatgac aaccttcaaa atcgagtccc | 60 |
| ggatccatgg caacctcaac ggggagaagt tcgagttggt tggaggtgga gtaggtgagg | 120 |
| agggtcgcct cgagattgag atgaagacta aagataaacc actggcattc tctcccttcc | 180 |
| tgctgtccca ctgcatgggt tacgggttct accacttcgc cagcttccca aaggggacta | 240 |
| agaacatcta tcttcatgct gcaacaaacg gaggttacac caacaccagg aaggagatct | 300 |
| atgaagacgg cggcatcttg gaggtcaact tccgttacac ttacgagttc aacaagatca | 360 |
| tcggtgacgt cgagtgcatt ggacatggat cccaagtca gagtccgatc ttcaaggaca | 420 |
| cgatcgtgaa gacttgtccc acggtggacc tgatgttgcc gatgtccggg aacatcatcg | 480 |
| ccagctccta cgctaaggcc ttccaactga aggacggctc tttctacacg gcagaagtca | 540 |
| agaacaacat agacttcaag aatccaatcc acgagtcctt ctcgaagtcg gggcccatgt | 600 |
| tcacccacag acgtgtcgag gagactcaca ccaaggagaa ccttgccatg gtggagtacc | 660 |
| agcaggtttt caacagcgcc ccaagagaca tgtagaattc tgcagatatc cagcacagtg | 720 |
| gcgaagctt | 729 |

<210> SEQ ID NO 105
<211> LENGTH: 729
<212> TYPE: DNA
<213> ORGANISM: Artificial Sequence
<220> FEATURE:
<223> OTHER INFORMATION: Synthetic oligonucleotide

<400> SEQUENCE: 105

| tctagatgca tcatcatcat catcatggcg gcagcatgac aaccttcaaa atcgagtccc | 60 |
| ggatccacgg caacctcaac ggggagaagt tcgagttggt tggaggtgga gtaggtgagg | 120 |
| agggtcgcct cgagattgag atgaagacta aagataaacc actggcattc tctcccttcc | 180 |
| tgctgaccac ttgcatgggt tacgggttct accacttcgc cagcttccca aaggggatta | 240 |
| agaacatcta tcttcatgct gcaacgaacg gaggttacac caacaccagg aaggagatct | 300 |
| atgaagacgg cggcatcttg gaggtcaact tccgttacac ttacgagttc aacaagatca | 360 |
| tcggtgacgt cgagtgcatt ggacatggat cccaagtca gagtccgatc ttcaaggaca | 420 |
| cgatcgtgaa gagttgtccc acggtggacc tgatgttgcc aatgtccggg aacatcatcg | 480 |
| ccagctccta cgcttacgcc ttccaactga aggacggctc tttctacacg gcagaagtca | 540 |
| agaacaacat agacttcaag aatccaatcc acgagtcctt ctcgaagtca gggcccatgt | 600 |
| tcacccacag acgtgtcgag gagactctca ccaaggagaa ccttgccata gtggagtacc | 660 |
| agcaggtttt caacagcgcc ccaagagaca tgtagaattc tgcagatatc cagcacagtg | 720 |
| gcgaagctt | 729 |

<210> SEQ ID NO 106
<211> LENGTH: 729
<212> TYPE: DNA
<213> ORGANISM: Artificial Sequence
<220> FEATURE:
<223> OTHER INFORMATION: Synthetic oligonucleotide

<400> SEQUENCE: 106

```
tctagatgca tcatcatcat catcatggcg gcagcatgac aaccttcaaa atcgagtccc      60
ggatccacgg caacctcaac ggggagaagt tcgagttggt tggaggtgga gtaggtgagg     120
agggtcgcct cgagattgag atgaagacta aagataaacc actggcattc tctcccttcc     180
tgctgtcctg ctgcatgggt tacgggttct accacttcgc cagcttccca aaggggactg     240
agaacatcta tcttcatgct gcaacaaacg gaggttacac caacaccagg aaggagatct     300
atgaagacgg cggcatcttg gaggtcaact tccgttacac ttacgagttc aacaagatca     360
tcggtgacgt cgagtgcatt ggacatggat tcccaagtca gagtccgatc ttcaaggaca     420
cgatcgtgaa gcaatggccc acggtggacc tgatgttgcc gatgtccggg aacatcatcg     480
ccagttccta cgctttggcc ttccaactga aggacggctc tttctacacg gcagaggtca     540
agaacaacat agacttcaag aatccaatcc acgagtcctt ctcgaagtcg ggcccatgt      600
tcacccacag acgtgtcgag gagactcaca ccaaggagaa ccttgccata gtggagtacc     660
agcaggtttt caacagcgcc ccaagagaca tgtagaattc tgcagatatc cagcacagtg     720
gcgaagctt                                                            729
```

UNITED STATES PATENT AND TRADEMARK OFFICE
CERTIFICATE OF CORRECTION

PATENT NO. : 10,900,045 B2
APPLICATION NO. : 15/737517
DATED : January 26, 2021
INVENTOR(S) : Ikuo Shiratori et al.

It is certified that error appears in the above-identified patent and that said Letters Patent is hereby corrected as shown below:

On the Title Page

(54) and in the Specification, Column 1, Lines 1-5:

Delete "PROTEIN, NOVEL GENE, EXPRESSION VECTOR, TRANSFORMANT, METHOD FOR PRODUCING TRANSFORMANT, AND METHOD FOR SCREENING FOR NOVEL FLUORESCENT PROTEIN"

Insert --NOVEL PROTEIN, NOVEL GENE, EXPRESSION VECTOR, TRANSFORMANT, METHOD FOR PRODUCING TRANSFORMANT, AND METHOD FOR SCREENING FOR NOVEL FLUORESCENT PROTEIN--

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*